US012181390B2

(12) United States Patent
Lee et al.

(10) Patent No.: US 12,181,390 B2
(45) Date of Patent: *Dec. 31, 2024

(54) SUBSTANCE LABELING PATCH, METHOD AND APPARATUS FOR TISSUE DIAGNOSIS USING THE SAME

(71) Applicant: NOUL CO., LTD., Yongin-si (KR)

(72) Inventors: Dong Young Lee, Yongin-si (KR); Chan Yang Lim, Seongnam-si (KR); Kyung Hwan Kim, Yongin-si (KR)

(73) Assignee: NOUL CO., LTD., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/364,392

(22) Filed: Aug. 2, 2023

(65) Prior Publication Data

US 2023/0393039 A1 Dec. 7, 2023

Related U.S. Application Data

(63) Continuation of application No. 16/079,236, filed as application No. PCT/KR2017/002029 on Feb. 23, 2017, now abandoned.

(Continued)

(30) Foreign Application Priority Data

| Jun. 4, 2016 | (KR) | 10-2016-0069936 |
| Jun. 4, 2016 | (KR) | 10-2016-0069937 |
| Jun. 4, 2016 | (KR) | 10-2016-0069938 |
| Jul. 27, 2016 | (KR) | 10-2016-0095739 |
| Sep. 13, 2016 | (KR) | 10-2016-0118462 |
| Nov. 1, 2016 | (KR) | 10-2016-0144551 |
| Feb. 23, 2017 | (KR) | 10-2017-0024390 |

(51) Int. Cl.

| G01N 1/31 | (2006.01) |
| B01L 3/00 | (2006.01) |
| C07K 16/30 | (2006.01) |
| C12Q 1/6844 | (2018.01) |
| C12Q 1/6848 | (2018.01) |
| C12Q 1/686 | (2018.01) |
| C12Q 1/70 | (2006.01) |
| G01N 1/30 | (2006.01) |
| G01N 15/06 | (2006.01) |
| G01N 15/14 | (2006.01) |
| G01N 21/77 | (2006.01) |
| G01N 33/483 | (2006.01) |
| G01N 33/49 | (2006.01) |
| G01N 33/50 | (2006.01) |
| G01N 33/52 | (2006.01) |
| G01N 33/53 | (2006.01) |
| G01N 33/533 | (2006.01) |

(Continued)

(52) U.S. Cl.
CPC ............... *G01N 1/312* (2013.01); *B01L 3/00* (2013.01); *C07K 16/3061* (2013.01); *C12Q 1/6844* (2013.01); *C12Q 1/6848* (2013.01); *C12Q 1/686* (2013.01); *C12Q 1/701* (2013.01); *G01N 1/30* (2013.01); *G01N 1/31* (2013.01); *G01N 15/06* (2013.01); *G01N 15/14* (2013.01); *G01N 21/77* (2013.01); *G01N 33/4833* (2013.01); *G01N 33/49* (2013.01); *G01N 33/5082* (2013.01); *G01N 33/52* (2013.01); *G01N 33/5304* (2013.01); *G01N 33/533* (2013.01); *G01N 33/558* (2013.01); *G01N 33/574* (2013.01); *G01N 33/60* (2013.01); *G06T 7/0012* (2013.01); *G06T 7/0014* (2013.01); *B01L 3/505* (2013.01); *B01L 7/52* (2013.01); *G01N 2001/302* (2013.01); *G01N 15/01* (2024.01); *G01N 15/075* (2024.01); *G01N 2021/7723* (2013.01); *G01N 2021/7786* (2013.01)

(58) Field of Classification Search
None
See application file for complete search history.

(56) References Cited

U.S. PATENT DOCUMENTS

| 555,270 A | 2/1896 | Taylor |
| 3,870,146 A | 3/1975 | Greenfield et al. |

(Continued)

FOREIGN PATENT DOCUMENTS

| CN | 1034617 A | 8/1989 |
| CN | 1207171 A | 2/1999 |

(Continued)

OTHER PUBLICATIONS

Markowitz, M. A. et al. "Diffusion and transfer of antibody proteins from a sugar-based hydrogel." *Applied biochemistry and biotechnology*, vol. 68, 1-2 (1997): pp. 57-68. doi:10.1007/BF02785980.

(Continued)

*Primary Examiner* — Ann Montgomery
(74) *Attorney, Agent, or Firm* — Kilpatrick Townsend & Stockton LLP

(57) ABSTRACT

The present disclosure relates to a tissue diagnosis device including a plate supporter configured to support a plate on which a reaction region is placed and a sample is placed in the reaction region, a patch controller configured to support the patch which contains a labeling substance that specifically labels the target substance, and control a position of the patch relative to the reaction region so that the patch provides the labeling substance to the reaction region, and a target substance detector configured to detect the labeling substance and detect the target substance included in the tissue sample.

13 Claims, 63 Drawing Sheets

Related U.S. Application Data

(60) Provisional application No. 62/298,959, filed on Feb. 23, 2016.

(51) Int. Cl.

| | | |
|---|---|---|
| *G01N 33/558* | (2006.01) | |
| *G01N 33/574* | (2006.01) | |
| *G01N 33/60* | (2006.01) | |
| *G06T 7/00* | (2017.01) | |
| *B01L 7/00* | (2006.01) | |
| *G01N 15/01* | (2024.01) | |
| *G01N 15/075* | (2024.01) | |

(56) References Cited

U.S. PATENT DOCUMENTS

| | | |
|---|---|---|
| 4,250,257 A | 2/1981 | Lee et al. |
| 4,839,297 A | 6/1989 | Freitag et al. |
| 4,938,593 A | 7/1990 | Morris et al. |
| 5,143,714 A | 9/1992 | Cosgrove et al. |
| 5,552,270 A | 9/1996 | Khrapko et al. |
| 5,552,279 A | 9/1996 | Weisburg et al. |
| 5,776,684 A * | 7/1998 | Chirikjian ............ C12Q 1/6816 435/6.15 |
| 5,779,982 A | 7/1998 | Aota et al. |
| 5,928,879 A | 7/1999 | Dumler et al. |
| 6,063,029 A | 5/2000 | Saita et al. |
| 6,174,683 B1 | 1/2001 | Hahn et al. |
| 7,261,800 B1 | 8/2007 | Nakazato |
| 7,522,757 B2 | 4/2009 | Tsipouras et al. |
| 7,767,414 B1 | 8/2010 | Smith et al. |
| 8,293,487 B1 | 10/2012 | Zhang |
| 8,305,579 B2 | 11/2012 | Treynor et al. |
| 8,409,849 B2 | 4/2013 | Yamasaki |
| 8,597,574 B2 | 12/2013 | Gumbrecht et al. |
| 8,628,787 B2 | 1/2014 | Soldani et al. |
| 8,809,027 B1 | 8/2014 | Lynch et al. |
| 8,936,912 B2 | 1/2015 | Mitra et al. |
| 10,234,447 B2 | 3/2019 | Manaresi et al. |
| 10,254,286 B2 | 4/2019 | Pirie-Shepherd et al. |
| 10,345,204 B2 * | 7/2019 | Lee ............ G01N 1/31 |
| 10,371,610 B2 * | 8/2019 | Lee ............ G01N 1/30 |
| 11,041,842 B2 | 6/2021 | Lee et al. |
| 11,360,005 B2 * | 6/2022 | Lee ............ G01N 1/312 |
| 11,366,043 B2 * | 6/2022 | Lee ............ G01N 1/31 |
| 11,740,162 B2 * | 8/2023 | Lee ............ G01N 1/30 436/518 |
| 2002/0055126 A1 | 5/2002 | Schaffler et al. |
| 2003/0083294 A1 | 5/2003 | Sullenger et al. |
| 2003/0086927 A1 | 5/2003 | Gordon et al. |
| 2003/0124619 A1 | 7/2003 | Weigl et al. |
| 2003/0211507 A1 | 11/2003 | Hatch et al. |
| 2004/0038306 A1 | 2/2004 | Agnew et al. |
| 2004/0126826 A1 | 7/2004 | Yusuf et al. |
| 2004/0175710 A1 | 9/2004 | Haushalter |
| 2005/0139511 A1 | 6/2005 | Burns et al. |
| 2005/0175987 A1 | 8/2005 | Jansen et al. |
| 2005/0175997 A1 | 8/2005 | Ono et al. |
| 2005/0202567 A1 | 9/2005 | Zanzucchi et al. |
| 2005/0244976 A1 | 11/2005 | Gee et al. |
| 2006/0088847 A1 | 4/2006 | Gu |
| 2006/0111331 A1 | 5/2006 | Eishingdrelo et al. |
| 2006/0115905 A1 | 6/2006 | Hatch et al. |
| 2006/0121474 A1 | 6/2006 | Kim et al. |
| 2006/0172278 A1 | 8/2006 | Bonner et al. |
| 2007/0051630 A1 | 3/2007 | Larsson et al. |
| 2007/0087362 A1 | 4/2007 | Church et al. |
| 2007/0117177 A1 | 5/2007 | Luo et al. |
| 2007/0128073 A1 | 6/2007 | Tappen |
| 2007/0224701 A1 | 9/2007 | Rosenstein |
| 2008/0090267 A1 | 4/2008 | Komatsu et al. |
| 2008/0138842 A1 | 6/2008 | Boehringer et al. |
| 2008/0182287 A1 | 7/2008 | Smith et al. |
| 2008/0241890 A1 | 10/2008 | Gumbrecht et al. |
| 2009/0098165 A1 | 4/2009 | Arulanandam et al. |
| 2009/0220968 A1 | 9/2009 | Issadore et al. |
| 2009/0226911 A1 | 9/2009 | Mauk et al. |
| 2010/0047790 A1 | 2/2010 | Southern et al. |
| 2010/0168390 A1 | 7/2010 | Brix et al. |
| 2011/0041978 A1 | 2/2011 | Wallace |
| 2011/0070606 A1 | 3/2011 | Winkelman et al. |
| 2011/0257666 A1 | 10/2011 | Ladet et al. |
| 2012/0040397 A1 | 2/2012 | Luo et al. |
| 2012/0064041 A1 | 3/2012 | Alexanian |
| 2012/0171290 A1 | 7/2012 | Coursaget et al. |
| 2013/0213811 A1* | 8/2013 | Kennedy .......... G01N 27/44739 204/601 |
| 2013/0288273 A1 | 10/2013 | Takagi et al. |
| 2013/0296761 A1 | 11/2013 | Goto et al. |
| 2013/0338016 A1 | 12/2013 | McDonough et al. |
| 2014/0004527 A1 | 1/2014 | Oka et al. |
| 2014/0038230 A1 | 2/2014 | Beck et al. |
| 2014/0073063 A1 | 3/2014 | Lieber et al. |
| 2014/0242607 A1 | 8/2014 | Sogabe et al. |
| 2014/0273088 A1 | 9/2014 | Winther |
| 2015/0080252 A1 | 3/2015 | Godwin et al. |
| 2015/0139511 A1 | 5/2015 | Yoon et al. |
| 2015/0167073 A1 | 6/2015 | Romanov et al. |
| 2016/0265028 A1 | 9/2016 | Kim et al. |
| 2019/0025281 A1 | 1/2019 | Lee et al. |
| 2019/0048395 A1 | 2/2019 | Lee et al. |
| 2019/0049349 A1 | 2/2019 | Lee et al. |
| 2019/0049426 A1 | 2/2019 | Lee et al. |
| 2019/0056296 A1 | 2/2019 | Lee et al. |
| 2019/0056298 A1 | 2/2019 | Lee et al. |
| 2019/0316695 A1 | 10/2019 | Feith et al. |
| 2019/0316995 A1 | 10/2019 | Lee et al. |
| 2020/0011772 A1 | 1/2020 | Lee et al. |
| 2020/0240882 A1 | 7/2020 | Lee et al. |
| 2020/0249134 A1 | 8/2020 | Lee et al. |

FOREIGN PATENT DOCUMENTS

| | | |
|---|---|---|
| CN | 1363006 A | 8/2002 |
| CN | 1409110 A | 4/2003 |
| CN | 1561202 A | 1/2005 |
| CN | 1747703 A | 3/2006 |
| CN | 1971276 A | 5/2007 |
| CN | 101004377 A | 7/2007 |
| CN | 101225430 A | 7/2008 |
| CN | 101464237 A | 6/2009 |
| CN | 101598731 A | 12/2009 |
| CN | 101610847 A | 12/2009 |
| CN | 102245305 A | 11/2011 |
| CN | 102245755 A | 11/2011 |
| CN | 102272595 A | 12/2011 |
| CN | 102665917 A | 9/2012 |
| CN | 103038639 A | 4/2013 |
| CN | 103261872 A | 8/2013 |
| CN | 103328651 A | 9/2013 |
| CN | 103800040 A | 5/2014 |
| CN | 103808551 A | 5/2014 |
| CN | 104271191 A | 1/2015 |
| CN | 104349769 A | 2/2015 |
| CN | 104651473 A | 5/2015 |
| CN | 105122034 A | 12/2015 |
| CN | 105136795 A | 12/2015 |
| CN | 105259095 A | 1/2016 |
| EP | 2072993 A2 | 6/2009 |
| EP | 2206462 A1 | 7/2010 |
| EP | 2072993 A3 | 11/2010 |
| EP | 2940474 A1 | 11/2015 |
| JP | 5289375 A | 7/1977 |
| JP | 63281050 A | 11/1988 |
| JP | 08271390 A | 10/1996 |
| JP | 2003344394 A | 12/2003 |
| JP | 2004077387 A | 3/2004 |
| JP | 2008518662 A | 6/2008 |
| JP | 2008164520 A | 7/2008 |
| JP | 2009518651 A | 5/2009 |
| JP | 2012515931 A | 7/2012 |
| JP | 5198399 B2 | 5/2013 |
| JP | 2013515235 A | 5/2013 |
| JP | 2013515955 A | 5/2013 |

(56) References Cited

FOREIGN PATENT DOCUMENTS

| | | | |
|---|---|---|---|
| KR | 100601831 | B1 | 7/2006 |
| KR | 20060112258 | A | 10/2006 |
| KR | 20110084636 | A | 7/2011 |
| KR | 20110136782 | A | 12/2011 |
| KR | 20130138153 | A | 12/2013 |
| KR | 20140082757 | A | 7/2014 |
| KR | 20140100580 | A | 8/2014 |
| KR | 20140103350 | A | 8/2014 |
| KR | 101453796 | B1 | 10/2014 |
| KR | 20150048964 | A | 5/2015 |
| KR | 101540845 | B1 | 7/2015 |
| WO | 0077293 | A1 | 12/2000 |
| WO | 02072081 | A1 | 9/2002 |
| WO | 02072262 | A1 | 9/2002 |
| WO | 2004024955 | A1 | 3/2004 |
| WO | 2004071469 | A2 | 8/2004 |
| WO | 2004071469 | A3 | 12/2004 |
| WO | 2006050032 | A2 | 5/2006 |
| WO | 2006053770 | A1 | 5/2006 |
| WO | 2006050032 | A3 | 9/2006 |
| WO | 2006108087 | A2 | 10/2006 |
| WO | 2007067847 | A2 | 6/2007 |
| WO | 2007067847 | A3 | 11/2007 |
| WO | 2008075086 | A1 | 6/2008 |
| WO | 2006108087 | A3 | 6/2009 |
| WO | 2010039627 | A2 | 4/2010 |
| WO | 2010041088 | A1 | 4/2010 |
| WO | 2010052543 | A1 | 5/2010 |
| WO | 2010039627 | A3 | 6/2010 |
| WO | 2010082820 | A2 | 7/2010 |
| WO | 2010082820 | A3 | 12/2010 |
| WO | 2010052543 | A8 | 3/2011 |
| WO | 2011066449 | A1 | 6/2011 |
| WO | 2011076705 | A1 | 6/2011 |
| WO | 2011080539 | A1 | 7/2011 |
| WO | 2011143075 | A2 | 11/2011 |
| WO | 2011143075 | A3 | 12/2011 |
| WO | 2012003579 | A1 | 1/2012 |
| WO | 2012030313 | A1 | 3/2012 |
| WO | 2012048154 | A1 | 4/2012 |
| WO | 2012072980 | A1 | 6/2012 |
| WO | 2012137506 | A1 | 10/2012 |
| WO | 2013086015 | A1 | 6/2013 |
| WO | 2013095896 | A1 | 6/2013 |
| WO | 2013103712 | A1 | 7/2013 |
| WO | 2013111054 | A1 | 8/2013 |
| WO | 2013169924 | A1 | 11/2013 |
| WO | 2014041093 | A1 | 3/2014 |
| WO | 2014146062 | A2 | 9/2014 |
| WO | 2014146062 | A3 | 12/2014 |
| WO | 2015137595 | A1 | 9/2015 |
| WO | 2017048871 | A1 | 3/2017 |

OTHER PUBLICATIONS

Extended European Search Report mailed Aug. 11, 2023 in European Patent Application No. 23172630.8, 9 pages.
"Bd™ Emb Agar (Eosin Methylene Blue Agar), Modified Intended Use", Becton, Dickinson and Company, Available Online at: https://www.bd.com/resource.aspx?idx=8973, 2013, pp. 1-3.
"Histology vol. II: Laboratory Products for Your Histology Needs", Cardinal Health, Available Online at: https://www.henryschein.com/assets/medical/2883001.pdf, 2013, 95 pages.
"Mesh", Available Online at: https://www.dictionary.com/browse/mesh?s=t, Sep. 7, 2022, 5 pages.
Beck et al., "On-Chip Sample Preparation by Controlled Release of Antibodies for Simple CD4 Counting", Lab on a Chip, vol. 12, No. 1, Nov. 3, 2011, pp. 167-173.
Deiss et al., "Antimicrobial Susceptibility Assays in Paper-Based Portable Culture Devices", Lab on a Chip, vol. 14, No. 1, Jan. 2014, pp. 167-171.
Geckil et al., "Engineering Hydrogels as Extracellular Matrix Mimics", Nanomedicine (Lond), vol. 5, No. 2, Apr. 2010, pp. 469-484.
Horibata et al., "Utilization of the Soft Agar Colony Formation Assay to Identify Inhibitors of Tumorigenicity in Breast Cancer Cells", Journal of Visualized Experiments, vol. 99, May 20, 2015, pp. 1-7.
Hudzicki , "Kirby-Bauer Disk Diffusion Susceptibility Test Protocol", Available Online at: https://asm.org/getattachment/2594ce26-bd44-47f6-8287-0657aa9185ad/Kirby-Bauer-Disk-Diffusion-Susceptibility-Test-Protocol-pdf.pdf, Dec. 8, 2009, 23 pages.
Liu et al., "Aptamer-Nanoparticle Strip Biosensor for Sensitive Detection of Cancer Cells", Analytical Chemistry, vol. 81, No. 24, Dec. 15, 2009, 13 pages.
Man et al., "Currently Used Markers for CTC Isolation—Advantages, Limitations and Impact on Cancer Prognosis", Journal of Clinical & Experimental Pathology, vol. 1, No. 1, 2011, 7 pages.
Massart et al., "Striatal GPR88 Expression is Confined to the Whole Projection Neuron Population and is Regulated by Dopaminergic and Glutamatergic Afferents", European Journal of Neuroscience, vol. 30, No. 3, Aug. 2009, pp. 397-414.
Matsuo et al., "A Simple Method for Classification of Cell Death by Use of Thin Layer Collagen Gel for the Detection of Apoptosis and/or Necrosis After Cancer Chemotherapy", Japanese Journal of Cancer Research, vol. 92, No. 7, Jul. 2001, pp. 813-819.
Notodihardjo et al., "Gelatin Hydrogel Impregnated with Platelet-Rich Plasma Releasate Promotes Angiogenesis and Wound Healing in Murine Model", Journal of Artificial Organs, vol. 18, No. 1, Mar. 2015, pp. 64-71.
Oss-Ronen et al., "Polymer-Conjugated Albumin and Fibrinogen Composite Hydrogels as Cell Scaffolds Designed for Affinity-Based Drug Delivery", Acta Biomaterialia, vol. 7, No. 1, Jan. 2011, pp. 163-170.
Application No. PCT/KR2017/002026 , International Search Report and Written Opinion, Mailed on May 29, 2017, 15 pages.
Application No. PCT/KR2017/002027 , International Search Report and Written Opinion, Mailed on May 29, 2017, 16 pages.
Application No. PCT/KR2017/002028 , International Search Report and Written Opinion, Mailed on Jul. 6, 2017, 17 pages.
Application No. PCT/KR2017/002029 , International Search Report and Written Opinion, Mailed on May 29, 2017, 17 pages.
Application No. PCT/KR2017/002030 , International Search Report and Written Opinion, Mailed on May 29, 2017, 18 pages.
Application No. PCT/KR2017/002031 , International Search Report and Written Opinion, Mailed on May 29, 2017, 23 pages.
Application No. PCT/KR2017/002032 , International Search Report and Written Opinion, Mailed on May 29, 2017, 21 pages.
Punyani et al., "Sustained Release of Iodine from a Polymeric Hydrogel Device for Water Disinfection", Journal of Applied Polymer Science, vol. 103, No. 5, Dec. 19, 2006, pp. 3334-3340.
Rand , "Crystal Violet can be Used to Visualize DNA Bands During Gel Electrophoresis and to Improve Cloning Efficiency", Technical Tips Online, vol. 1, No. 1, Jan. 1996, pp. 23-24.
Romano et al., "Controlled Antiseptic/Eosin Release from Chitosan-Based Hydrogel Modified Fibrous Substrates", Carbohydrate Polymers, vol. 131, Oct. 20, 2015, 27 pages.
Wakayama et al., "Design of a Single-Step Immunoassay Principle Based on the Combination of an Enzyme-Labeled Antibody Release Coating and a Hydrogel Copolymerized with a Fluorescent Enzyme Substrate in a Microfluidic Capillary Device", Lab on a Chip, vol. 13, No. 22, Nov. 21, 2013, pp. 4304-4307.
Wu et al., "Disposable Reagentless Electrochemical Immunosensor Array Based on a Biopolymer/Sol-Gel Membrane for Simultaneous Measurement of Several Tumor Markers", Clinical Chemistry, vol. 54, No. 9, Sep. 2008, pp. 1481-1488.
Zhu et al., "Microbiology Experiment and Learning Guide—Experiment 6 In Vitro Antibacterial Test of Drug", Fourth Force Medical University Press, 2015, 11 pages.
Zustiak et al., "Solute Diffusion and Interactions in Cross-Linked Poly(Ethylene Glycol) Hydrogels Studied by Fluorescence Correlation Spectroscopy", Soft Matter, vol. 6, No. 15, Aug. 7, 2010, 24 pages.

* cited by examiner

SUBSTANCE LABELING PATCH, METHOD AND APPARATUS FOR TISSUE DIAGNOSIS USING THE SAME

This application is a continuation of U.S. patent application Ser. No. 16/079,236, filed on Aug. 23, 2018, which is a 371 National phase filing of PCT/KR2017/002029, filed Feb. 23, 2017, which is based on and claims priority to U.S. Provisional Patent Application No. 62/298,959, filed on Feb. 23, 2016, and Patent Application No. 10-2017-0024390 filed on Feb. 23, 2017, Patent Application No. 10-2016-0144551 filed on Nov. 1, 2016, Patent Application No. 10-2016-0118462 filed on Sep. 13, 2016, Patent Application No. 10-2016-0095739 filed on Jul. 27, 2016, Patent Application No. 10-2016-0069938 filed on Jun. 4, 2016, Patent Application No. 10-2016-0069937 filed on Jun. 4, 2016, and Patent Application No. 10-2016-0069936 filed on Jun. 4, 2016, all in the Republic of Korea Intellectual Property Office, the disclosures of which are incorporated by reference herein in their entirety for all purposes.

TECHNICAL FIELD

The present disclosure relates to a substance labeling patch, a method of and apparatus for tissue diagnosis using the same, and mate particularly, to a patch that contains a labeling substance and a method and apparatus capable of performing prompt and accurate diagnosis on a tissue sample by using the patch and labeling a portion of the tissue sample.

BACKGROUND ART

Due to a rapidly aging society and increasing need for quality of life, the diagnostic market which aims at early diagnosis and early treatment is growing every year in the world, including South Korea, and quick and easy diagonals is becoming an important issue. In particular, forma of diagnosis are bring transitioned into forms in which diagnosis can be performed without using large diagnostic equipment, such as in-vitro diagnosis (IVD) or paint-of-care testing (POCT) which is immediately performed next to a patient. Immunochemical diagnosis, which is one specific diagnostic field for performing IVD, is one diagnostic method that accounts for a large portion in the IVD field and is widely used.

Histological diagnosis is a concept that encompasses pathological diagnoses performed with a tissue, which is a cellular organizational level intermediate between cells and a complete organ and is an ensemble of similar cells, as a sample. Particularly, diagnoses performed with a tissue as a sample are mostly used in cancer diagnosis. When development of cancer is suspected through clinical or image diagnosis, a portion of a tissue which is suspected as cancer is collected from a patient by using a method such as fine needle aspiration. The collected tissue is used in diagnosis after a tissue processing process. In this case, diagnosis may be performed by observing the morphology of cells that constitute the tissue or determining a presence of a specific protein.

In a conventional tissue diagnosis method, in a process in which a sample is stained or gone through the fluorescence process, a washing process in which a large amount of washing solution is poured on a plate or the like to rinse it in order to remove staining reagent or fluorescent substances which are not bound to a substance to be detected is necessarily required. In this case, there is a disadvantage in that the large amount of washing solution is required. Also, the conventional tissue diagnosis shod has a problem in that, when the above-described washing is not perforated properly, the remaining stains or remaining fluorescent substances interfere with detection, and it becomes difficult to perform accurate diagnosis.

Accordingly, a means for effectively removing factors that interfere with detection while minimizing an amount of specimen required for diagnosis is needed.

SUMMARY

An aspect of the present disclosure is to provide a patch capable of storing a substance.

An aspect of the present disclosure is to provide a patch capable of providing a reaction space for a substance.

An aspect of the present disclosure is to provide a patch capable of providing a substance.

An aspect of the present disclosure is to provide a patch capable of absorbing a substance.

An aspect of the present disclosure is to provide a patch capable of providing an environment.

An aspect of the present disclosure is to provide a patch that contains a labeling substance.

An aspect of the prevent disclosure is to provide a tissue diagnosis method using a patch.

According to an aspect of the present disclosure, there is provided a tissue diagnosis device for detecting a target substance from a tissue sample by using a patch which includes a mesh structural body forming micro-cavities and is configured to contain a substance in the micro-cavities, the tissue diagnosis device including a plate supporter configured to support a plate on which a reaction region is placed and a sample is placed in the reaction region, a patch controller configured to support the patch which contains a labeling substance that specifically labels the target substance, and control a position of the patch relative to the reaction region so that the patch comes into contact with the reaction region and provides the labeling substance to the reaction region, and a target substance detector configured to detect the labeling substance and detect the target substance included in the tissue sample.

The target substance detector may include an imaging module configured to acquire an image of the reaction region in which the tissue sample is placed. The target substance detector may include a measurement module configured to measure an amount of the target substance included in the tissue sample.

According to another aspect of the present disclosure, there is provided a tissue diagnosis method for detecting a target substance form a tissues sample by using a patch which includes a mesh structural body forming micro-cavities and is configured to contain a substance in the micro-cavities, the tissue diagnosis method including placing the tissue samples in a reaction region, providing a fluorescence labeling substance for specifically labeling the target substance to the tissue sample by using a patch that contains the fluorescence labeling substance, and detecting the fluorescence-labeled target substance front due tissue sample.

The fluorescence labeling substance may be a fluorescence labeling complex that includes a reaction derivative that reacts specifically with the target substance and a fluorescence marker for detecting the target substance.

The detecting of the fluorescence-labeled target substance may be performed by obtaining a fluorescence image of the tissue sample. The detecting of the fluorescence-labeled target substance may be performed by measuring an amount of fluorescence emitted from the target substance included in the tissue sample. The detecting of the fluorescence-labeled target substance may include obtaining information on distribution of the target substance in the tissue sample.

The target substance may be a target base sequence included in the tissue sample, the fluorescence labeling substance may include a fluorescence-labeled nucleic acid probe, and the nucleic acid probe may bind complementarily to the target base impart. Alternatively, the target substance may be a target protein included in the tissue sample, the fluorescence labeling substance may include a fluorescence-labeled antibody, and the antibody may bind specifically to the target protein.

The providing of the fluorescence labeling substance to the tissue sample may include contacting the patch containing the fluorescence labeling assistance with the tissue sample, and when the patch is in contact with the tissue sample, the fluorescence labeling substance may be allowed to move to the reaction region.

The providing of the fluorescence labeling substance to the tissue sample may include separating the patch containing the fluorescence labeling substance from the tissue sample, and when the patch is separated from the tissue sample, a residual fluorescence labeling substance that has not bound to the target substance of the fluorescence labeling substance may be removed from the reaction region.

According to still another aspect of the present disclosure, there is provided a tissue diagnosis method for detecting a target substance from a tissue sample by using a patch which includes a mesh structural body forming micro-cavities and is configured to contain a substance in the micro-cavities, the tissue diagnosis method including placing the tissue sample in a reaction region, providing staining substance to the tissue sample by using a patch that contains color labeling substance for assigning color to the target substance, and detecting the color-assigned target substance.

The color labeling substance may be a color labeling complex that includes a reaction derivative that reacts specifically with the target substance and a color marker for detecting the target substance.

The detecting of the color-assigned target substance may be performed by acquiring an image of the tissue sample. The detecting of the color-labeled target substance may include obtaining an amount of the color-labeled target substance in the tissue sample. The detecting of the color-labeled target substance may include obtaining a distribution of color-labeled regions in the tissue sample.

The target substance may be a target base sequence included in the tissue sample, the odor labeling substance may include a nucleic acid probe that binds complementarily to the target base sequence. The target substance may be a target protein included in the tissue sample, the color labeling substance may include an antibody to which a marker for inducing color labeling is attached, and the antibody may bind specifically to the target protein.

The providing of the color labeling substance to the tissue sample may include contacting the patch containing the color labeling substance with the tissue sample, and when the patch is in contact with the tissue sample, the color labeling substance may be allowed to move to the reaction region.

The providing of the color labeling substance to the tissue sample may include separating the patch containing the color labeling substance from the tissue sample, and when the patch is separated front the tissue sample, a residual color labeling substance that has not bound to the target substance of the color labeling substance may be removed rem the reaction region.

According to yet another aspect of the present disclosure, there is provided a tissue diagnosis method for detecting a target substance from a tissue sample by using a patch which includes a mesh structural body forming micro-cavities and is configured to contain a substance in the micro-cavities, the tissue diagnosis method including placing the tissue sample in a reaction region, providing a first fluorescence labeling substance for specifically labeling a first target substance to the tissue sample by using a patch that contains the first fluorescence labeling substance, and providing a second fluorescence labeling substance for specifically labeling a second target substance to the tissue sample by using a patch that contains the second fluorescence labeling substance.

A wavelength band from which fluorescence emitted from the first fluorescence labeling substance is detected and a wavelength band from which fluorescence emitted from the second fluorescence labeling substance is detected may be different from each other, and the tissue diagnosis method may further include, after the providing of the second fluorescence labeling substance to the tissue sample, detecting the first target substance and the second target substance included in the tissue sample.

The tissue diagnosis method may further include, after the providing of the first fluorescence labeling substance to the tissue sample, detecting the first target substance included in the tissue sample by detecting fluorescence emitted from the first fluorescence labeling substance, and may further include, after the providing of de second fluorescence labeling substance to the tissue sample, detecting the second target substance included in the tissue sample by detecting fluorescence emitted firm the second fluorescence labeling substance.

The wavelength band from which the fluorescence emitted from the first fluorescence labeling substance is detected and the wavelength band from which the fluorescence is emitted from the second fluorescence labeling substance is detected may at least partially overlap each ether, and the detecting of the fluorescence emitted from the second fluorescence labeling substance may be performed by comparing fluorescence detected from the tissue sample after the second fluorescence labeling substance is provided to the tissue sample and fluorescence detected from the tissue sample before the second fluorescence labeling substance is provided to the tissue sample.

According to yet another aspect of the present disclosure, there is provided a substance labeling patch including a labeling substance that binds to a target substance included in a tissue sample to label the target substance, and a mesh structural body having a mesh structure forming micro-cavities in which the labeling substance is contained that is configured to come into contact with the tissue sample and provide the labeling substance to a reaction region in which the target substance is placed. The target substance may be DNA included in the tissue sample.

The labeling substance may be a fluorescence labeling substance.

The fluorescence labeling substance may include a fluorescence-labeled antibody, and the target substance may be a target protein included in the tissue sample. The fluorescence labeling substance may include a fluorescence-labeled nucleic acid probe, and the target substance may be a target base substance included in the tissue sample.

The labeling substance may be a color labeling substance.

The color labeling substance may include an enzyme-attached antibody, and the target substance may be a target protein included in the sample. The color labeling substance may include hematoxylin, and the target substance may be a nucleus included in the sample.

Solutions for solving the technical problems of the present disclosure are not limited to the above-described solutions, and other unmentioned solution should be clearly understood by those of ordinary skill in the art to which the present disclosure pertains from the present specification and the accompanying drawings.

According to the present disclosure, containing, providing, and absorption of a substance can be easily performed.

According to the present disclosure, a reaction region for a substance can be provided or a predetermined environment can be provided to a target region.

According to the present disclosure, diagnosis performed with a tissue as a sample can be mare conveniently performed, and a diagnosis result can be promptly obtained.

According to the present disclosure, providing and absorption of a substance can be properly adjusted using a path, and an amount of a solution consumed for diagnosis can be significantly reduced.

According to the present disclosure, tissue diagnosis can be performed by simultaneously detecting a plurality of targets.

Advantageous effects of the present disclosure are not limited to those mentioned above, and unmentioned advantageous effects should be clearly understood by those of ordinary skill in the art to which the present disclosure pertains from the present specification and the accompanying drawings.

DETAILED DESCRIPTION

Figure 1:
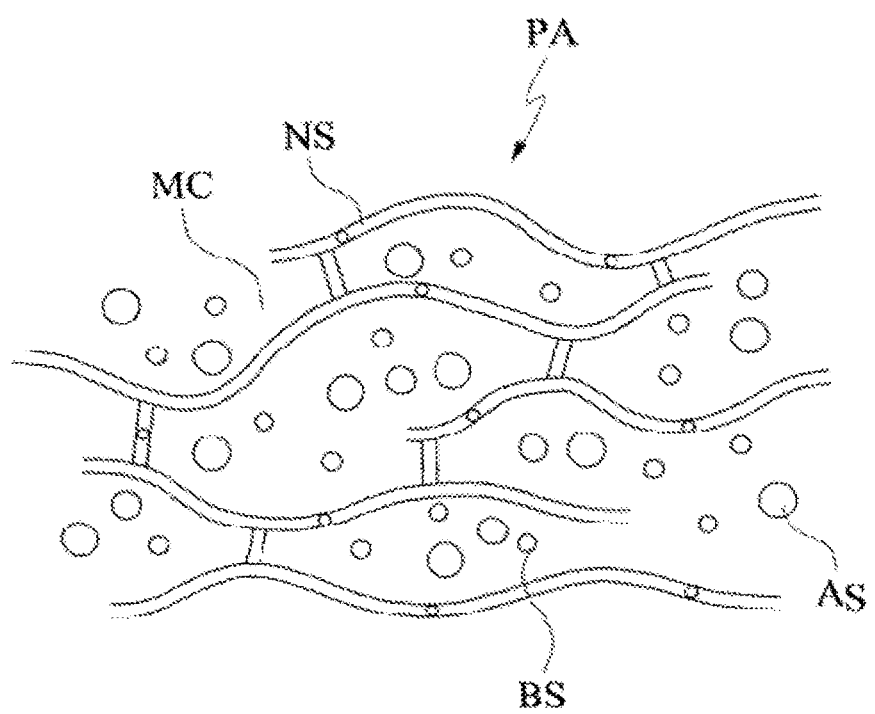
FIG. 1 illustrates an example of a patch in detail according to the present application.

Since embodiments described herein are for clearly describing the spirit of the present disclosure to those of ordinary skill in the art to which the present disclosure pertains, the present disclosure is not limited to the embodiments described herein, and the scope of the present disclosure should be construed as including revised examples or modified examples not departing from the spirit of the present disclosure.

General terms currently being used as widely as possible have been selected as terms used herein in consideration of functions in the present disclosure, but the terms may be changed according to intentions and practices of those of ordinary skill in the art to which the present disclosure pertains or the advent of new technologies, etc. However, instead, when a particular term is defined as a certain meaning and used, the meaning of the term will be separately described. Consequently, the terms used herein should be construed on the basis of substantial meanings of the terms and content throughout the present specification instead of simply on the basis of names of the terms.

The accompanying drawings herein are for easily describing the present disclosure. Since shapes illustrated in the drawings may have been exaggeratedly depicted as much as necessary to assist in understating the present disclosure, the present disclosure is not limited by the drawing.

When detailed description of a known configuration or function related to the present disclosure is deemed to obscure the gist of the present disclosure in the present specification, the detailed description related thereto will be omitted as necessary.

1. Patch 1.1 Meaning of Patch

In the present application, a patch for massaging a liquid substance is disclosed.

The liquid substance may mean a substance which is in a liquid state and can flow.

The liquid substance may be a substance formed of a single component hawing fluidity. Alternatively, the liquid substance may be a mixture that includes a substance formed of a plurality of components.

When the liquid substance is a substance formed of a single component, the liquid substance may be a substance formed of a single chemical element or a compound including a plurality of chemical elements.

When the liquid substance is a mixture, a portion of the substance formed of a plurality of components may serve as a solvent, and the other portion may serve as a solute. That is, the mixture may be a solution.

A plurality of component constituting the mixture which forms the substance may be uniformly distributed. Alternatively, the mixture including the substance formed of a plurality of components may be a uniformly mixed mixture.

The substance formed of a plurality of components may include a solvent and a substance that is not dissolved in the solvent and is uniformly distributed.

A portion of the substance formed of a plurality of components may be non-uniformly distributed. The non-uniformly distributed substance may include non-uniformly distributed particle components in the solvent. In this case, the non-uniformly distributed particle components may be in a solid phase.

For example, a substance that may be managed using the patch may be in a ire of 1) a liquid formed of a single component, 2) a solution, or 3) a colloid, or according to circumstances, may be in a state in which 4) solid particles are non-uniformly distributed within another liquid substance.

Hereinafter, the patch according to the present application will be described in more detail.

1.2 General Nature of Patch 1.2.1 Configuration

Figure 2:
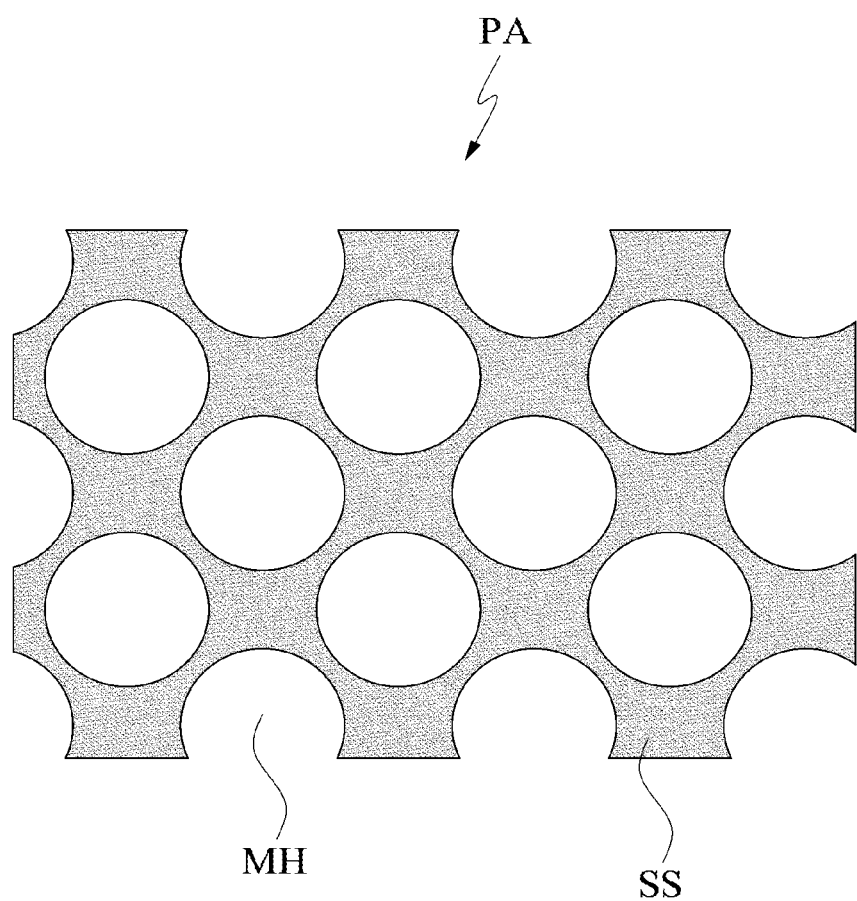
FIG. 2 illustrates an example of a patch in detail according to the present application.

FIGS. 1 and 2 are views illustrating an example of a patch according to the proem application. The patch according to the present application will be described below with reference to FIGS. 1 and 2.

Referring to FIG. 1, a patch PA according to the present application may include a mesh structural body NS and a liquid substance.

As the liquid substance, a base substance BS and an additive substance AS many be taken into consideration separately.

The patch PA may be in a gel state (gel type). The patch PA may be implemented as a gel-tape structural body in which colloidal molecules are bound and mesh tissues are formed.

The patch PA according to the present application is a structure for managing a liquid substance SB, and map include a three-dimensional mesh (net-like) structural body NS. The mesh structural body NS may be a continuously distributed sold structure. The mesh structural body NS may have a mesh structure in which a plurality of micro-threads are intertwined. However, the mesh structural body NS a not limited to the mesh form in which the plurality of micro-threads are intertwined, and may also be implemented in the form of an arbitrary three-dimensional matrix that is formed by connection of a plurality of micro-structures. For example, the mesh structural body NS may be a frame structural body that incudes a plurality of micro-cavities. In other words, the mesh structural body NS may form a plurality of micro-cavities MC.

FIG. 2 illustrates a stature of a patch according to an embodiment of the preset application. Referring to FIG. 2, the mesh structural body of the patch PA may have a sponge structure SS. The mesh structural body of the sponge structure SS may include a plurality of micro-holes MH. Hereinafter, the teams micro-holes MH and the micro-cavities MC may be used interchangeably, and unless particularly mentioned otherwise, the term micro-cavities MC is defined as encompassing the concept of the micro-holes MH.

The mesh structural body NS may have a regular or irregular pattern. Furthermore, the mesh structural body NS may include both a region having a regular pattern and a region having an irregular pattern.

A density of the mesh structural body NS may have a value within a predetermined range. Preferably, the predetermined range may be set within a limit in which the form of the liquid substance SB captured in the patch PA is maintained in a form that corresponds to the patch PA. The density may be defined as a degree to which the mesh structural body NS is dense or a mass ratio, a volume ratio, or the like that the mesh structural body NS occupies in the patch.

The patch according to the present application may manage the liquid substance SB by having a three-dimensional mesh structure.

The patch PA according to the present application may include the lipid substance SB, and the fluidity of the liquid substance SB included in the patch PA may be limited by the form of the mesh structural body NS of the patch PA.

The liquid substance SB may freely flow within the mesh structural body NS. In other words, the liquid substance SB is placed in the plurality of micro-cavities formed by the mesh structural body NS. An exchange of liquid substance SB may occur between neighboring micro-cavities. In this case, the liquid substance SB may be present in a state in which the lipid substance SB permeating into a frame structural body that forms the mesh tissues. In such a case, nano-sized pores into which the liquid substances SB may permeate may be formed in the frame structural body.

Further, whether to the liquid substance SB is filled in the frame structural body of the mesh structure may be determined depending on a molecular weight or a particle size of the liquid substance SB to be captured in the patch PA. A substance having a relatively large molecular weight may be captured in the micro-cavities, and a substance having a relatively small molecular weight may be captured by the frame structural body and filled in the micro-cavities and/or the frame structural body of the mesh structural body NS.

In the present specification, the term "capture" may be defined as a state in which the liquid substance SB is placed in the plurality of micro-cavities and/or nano-sized holes formed by the mesh structural body NS. As described above, the state in which the liquid substance SB is captured in the patch PA is defined as including a state in which the liquid substance SB may flow between the micro-cavities and/or the nano-sized holes.

As in the following, the base substance BS and the additive substance AS may be taken into consideration separately as the liquid substance SB.

The base substance BS may be a liquid substance SB having fluidity.

The additive substance AS may be a substance that is mixed with the base substance BS and has fluidly. In other words, the base substance BS may be a solvent. The additive substance AS may be a solute that is dissolved in the solvent or may be particles that are not melted in the solved.

The base substance BS may be a substance capable of flowing inside a matrix formed by the mesh structural body NS. The base substance BS may be uniformly distributed in the mesh structural body NS or may be distributed only in a partial region of the math structural body NS. The baste substance BS may be a liquid having a single component.

The additive substance AS may be a substance that is mixed with the base substance BS or dissolved in the base substance BS. For example, the additive substance AS may serve as a solute while the base substance BS is a solvent. The additive substance AS may be uniformly distributed in the base substance BS.

The additive substance AS may be fine particles that are not dissolved in the base substance BS. For example, the additive substance AS may include colloidal molecules and fine particles such as microorganisms.

The additive substance AS may include particles larger than the micro-cavities formed by the mesh structural body NS. When the size of the micro-cavities is smaller than the size of the particles included in the additive substance AS, fluidity of the additive substance AS may be limited.

According to an embodiment, the additive substance AS may include a component that is selectively included in the patch PA.

The additive substance AS does not necessarily refer to a substance that is lower in quantity or inferior in function in comparison to the above-described base substance BS.

Hereinafter, characteristic of the liquid substance SB captured in the patch PA may be presumed as characteristics of the patch PA. That is, the characteristics of the patch PA may depend an characteristics of a substance captured in the patch PA.

1.2.2 Characteristics

As described above, the patch PA according to the present application may include the mesh structural body NS. The patch PA may manage the liquid substance SB through the mesh structural body NS. The patch PA may allow the liquid substance SB captured in the patch PA to maintain at least some of its unique characteristics.

For example, diffusion of a substance may occur in a region of the patch PA in which the liquid substance SB is distributed, and a force such as surface tension may come into action.

The patch PA may pride a liquid environment in which diffusion of a target substance is caused due to thermal motion of a substance or a difference in density or concentration thereof. Generally, "diffusion" refers to a phenomenon in which particles that constitute a substance are spread from a side at which concentration is high to a side at which a concentration is low due to a difference in concentration. Such a diffusion phenomenon may be basically understood as a phenomenon that occurs due to motion of molecules (translational motion in a gas or liquid, vibrational motion in a solid, and the like). In the prevent application, in addition to referring to the phenomenon in which particles are spread from a side at which a concentration is high toward a side at which a concentration is low due to a difference in concentration density, "diffusion" also refers to a phenomenon in which particles move due to irregular motion of molecules that occurs even when a concentration is uniform. The expression "irregular motion" may also have the same meaning as "diffusion" unless particularly mentioned otherwise. The diffused substance may be a solute that is dissolved in the lipid substance SB, and the diffused substance may be provided in a solid, liquid, or gas state.

More specifically, a non-uniformly-distributed substance in the liquid substance SB captured by the patch PA may be diffused in a space provided by the patch PA. In other words, the additive substance AS may be diffused in a apace defined by the patch PA.

The non-distributed substance or the additive substance AS in the liquid substance SB managed by the patch PA may be diffused within the micro-cavities provided by the mesh structural body NS of the patch PA. A region in which the non-uniformly-distributed substance or the additive substance AS may be diffused may be changed by the patch PA being connected or coming into contact with another imbalance.

Even when, after the concentration of the substance or the additive substance AS has become uniform, as a result of diffusion of the non-uniformly-distributed substance or the additive substance AS within the patch PA or within an external region connected to the patch PA, the substance or the additive substance AS may continuously move due to irregular motion of molecules inside the patch PA and/or within the external region connected to the patch PA.

The patch PA may be implemented to exhibit a hydrophilic or hydrophobic property. In other words, the mesh structural body NS of the patch PA may have a hydrophilic or hydrophobic property.

When properties of the mesh structural body NS and the liquid substance SB are similar, the meth structural body NS may be able to manage the liquid substance SB more effectively.

The base substance BS may be a polar hydrophilic substance or a nonpolar hydrophobic substance. The additive substance AS may exhibit a hydrophilic or hydrophobic property.

The properties of the liquid substance SB may be related to the base substance BS and/or the additive substance AS. For example, when both the hose substance BS and the additive substance AS are hydrophilic, the liquid substance SB may be hydrophilic, and when both the base substance BS and the additive substance AS are hydrophobic, the liquid substance SB may be hydrophobic. When polarities of the base substance BS and the additive substance AS are different, the liquid substance SB may be hydrophilic or hydrophobic.

When polarities of both the mesh structural body NS and the liquid substance SB are hydrophilic or hydrophobic, an attractive force may come into action between the mesh structural body NS and the liquid substance SB. When polarities of the mesh structural body NS and the liquid substance SB are opposite, e.g., when the polarity of the mesh structural body NS is hydrophobic and the polarity of the liquid substance SB is hydrophilic, a repulsive force may act between the mesh structural body NS and the liquid substance SB.

On the basis of the above-described properties, the patch PA may be solely used, a plurality of patches PA may be used, or the patch PA may be used with another medium to induce a desired reaction. Hereinafter, functional aspects of the perch PA will be described.

However, hereinafter, for convenience of description, the patch PA is assumed as being a gel type that may include a hydrophilic solution. In other words, unless particularly mentioned otherwise, the mesh structural body NS of the patch PA is assumed to have a hydrophilic property.

However, the scope of the present application should not be interpreted as being limited to the gel-type patch PA having a hydrophilic property. In addition to a gel-type porch PA that includes a solution exhibiting a hydrophobic property, a gel-type patch PA from which a solvent is removed and even a sol-type patch PA, as long as it is capable of implementing functions according to the present application, may belong to the scope of the present application.

2. Functions of Patch

Due to the above-described characteristics, the patch according to the present application may have some useful functions. In other words, by capturing the liquid substance SB, the patch may become involved in behavior of the liquid substance SB.

Accordingly, hereinafter, in accordance with forms of behavior of the substance with respect to the patch PA, a reservoir function in which a state of the substance is defined in a predetermined region formed by the patch PA and a channeling function is which a state of the substance is defined in a region including an external region of the perch PA will be separately described.

2.1 Reservoir

2.1.1 Meaning

As described above, the patch PA according to the present application may capture the liquid substance SB. In other words, the patch PA may perform a function as a reservoir.

The patch PA may capture the liquid substance SB in the plurality of micro-cavities formed in the mesh structural body NS using the mesh structural body NS. The liquid substance SB may occupy at least a portion of the fine micro-cavities formed by the three-dimensional mesh structural body NS of the patch PA or be penetrated in the nano-sized pores formed in the mesh structural body NS.

The liquid substance SB placed in the patch PA does not lose properties of a liquid even when the liquid substance SB is distributed in the plurality of micro-cavities. That is, the liquid substance SB has fluidity even in the patch PA, and diffusion of a substance may occur in the liquid substance SB distributed in the patch PA, and an appropriate solute may be dissolved in the substance.

The reservoir function of the patch PA will be described below in more detail.

2.1.2 Containing

In the present application, the patch PA may capture a target substance due to the above-described characteristics. The patch PA may have resistance to a change in an external environment within a predetermined range. In this way, the patch PA may maintain a state in which the substance is captured therein. The liquid substance SB, which is a target to be captured, may occupy the three-dimensional mesh structural body NS.

Hereinafter, for convenience, the above-described function of the patch PA will be referred to as "containing."

However, "the patch PA containing the liquid substance" is defused to encompass a case in which the liquid substance is contained in a space formed by the mesh structure and/or a case in which the liquid substance is contained in the frame structural body constituting the mesh structural body NS.

The patch PA may contain the liquid substance SB. For example, the patch PA may contain the liquid substance SB, due to an attractive force that acts between the mesh structural body NS of the patch PA and the liquid substance SB. The liquid substance SB may be bound to the mesh structural body NS with an attractive force of a predetermined strength or higher and contained in the patch PA.

Properties of the liquid substance SB contained in the patch PA may be classified in accordance with properties of the patch PA. More specifically, when the patch PA exhibits a hydrophilic property, the patch PA may be bound to a hydrophilic liquid substance SB which is polar in general and contain the hydrophilic liquid instance SB in the three-dimensional micro-cavities. Alternatively, when the patch PA exhibits a hydrophobic property, the hydrophobic liquid substance SB may be contained in the micro-cavities of the three-dimensional mesh structural body NS.

The amount of substance that may be contained in the patch PA may be proportional to a volume of the patch PA. In other words, the amount of substance contained in the patch PA may be proportional to an amount of three-dimensional mesh structural body NS that serves as a support body that contributes to the form of the patch PA. However, there is no constant proportional factor between the amount of substance that may be contained in the patch PA and the volume of the patch PA, and thus the relationship between the amount of substance that may be contained in the patch PA and the volume of the patch PA may be changed in accordance with the design or manufacturing method of the mesh structure.

The amount of substance contained in the patch PA may be reduced due to evaporation, loss, etc. with time. The substance may be additionally injected into the patch PA to increase or maintain the content of the substance contained in the patch PA. For example, a moisture keeping agent for suppressing evaporation of moisture may be added to the patch PA.

The patch PA may be implemented in a form in which it is easy to store the liquid substance SB. This signifies that, when the substance is affected by environmental factors such as humidity level, amount of light, and temperature, the patch PA may be implemented to minimize denaturalization of the substance. For example, to prevent the patch PA from being denaturalized due to external factors such as bacteria, the patch PA may be treated with a bacteria inhibitor.

A liquid substance SB having a plurality of components may be contained in the patch PA. In this case, the substance formed at a plurality of components may be placed together in the patch PA before a reference time point, or a primarily-injected substance may be first contained in the patch PA and then a secondary substance may be contained in the patch PA after a predetermined amount of time. For example, when a liquid substance SB formed of two components is contained in the patch PA, the two components may be contained in the patch PA upon manufacturing the patch PA, only one component may be contained in the patch PA upon manufacturing the patch PA and the other component may be contained therein later, or the two components may be sequentially contained in the patch PA after the patch PA is manufactured.

As described above, the substance contained in the patch may exhibit fluidity and the substance may move irregularly or be diffused due to molecular motion in the patch PA.

2.1.3 Providing of Reaction Space

Figure 3:
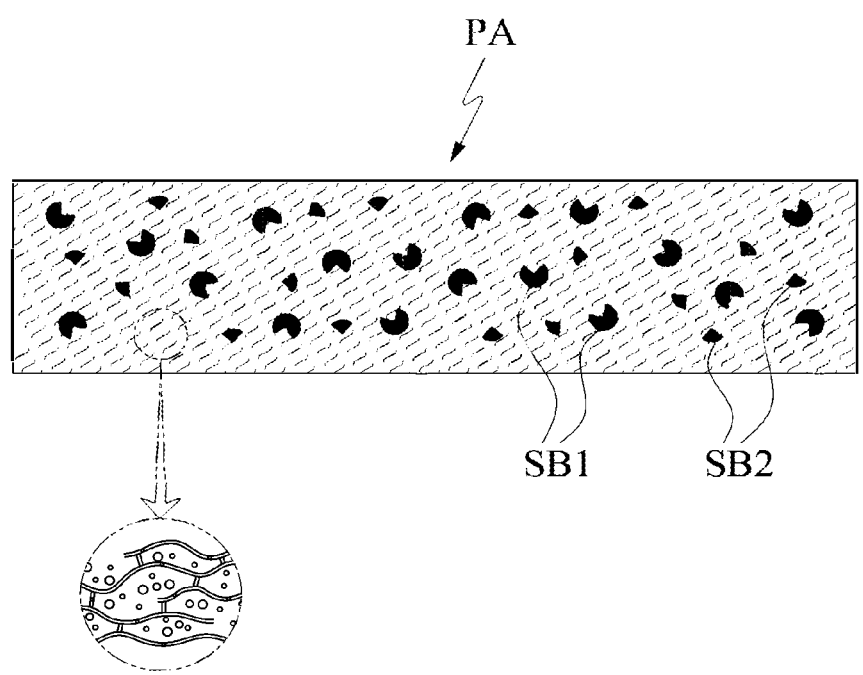
FIG. 3 illustrates provided of a reaction space as an example of a function of a patch according to the present application.
Figure 4:
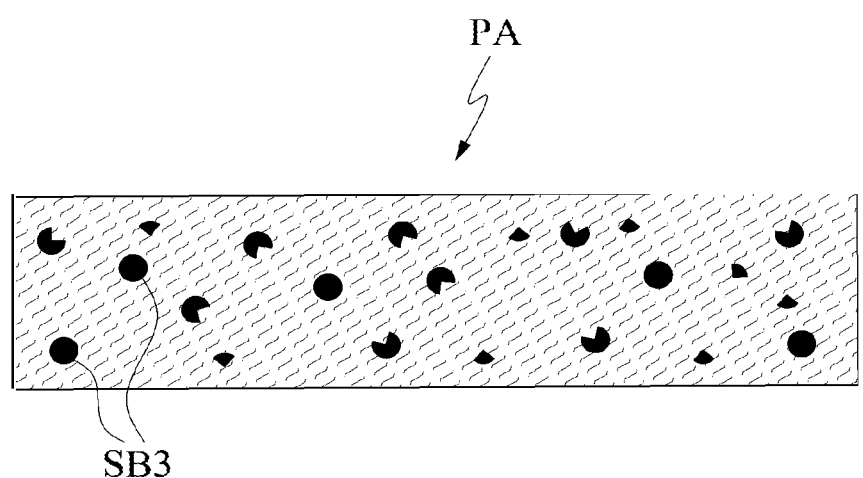
FIG. 4 illustrates providing of a reaction space as an example of a function of a patch according to the present application.

FIGS. 3 and 4 are views illustrating providing a reaction space as an example of a function of the patch according to the present application.

As illustrated in FIGS. 3 and 4, the patch PA according to the present application may perform a function of providing a space. In other words, the patch PA may provide a apace in which the liquid substance SB may move through a apace formed by the mesh structural body NS and/or a space constituting the mesh structural body NS.

The patch PA may provide a space for activity other than diffusion of particles and/or irregular motion of panicles (hereinafter referred to an activity other than diffusion). The activity other than diffusion may refer to a chemical reaction, but is not limited thereto, and may also refer to a physical state change. More specifically, the activity other than diffusion may include a chemical reaction in which a chemical composition of the substance changes after the activity, a specific binding reaction between components included in the substance, homogenization of solutes or particles included in the substance and non-uniformly distributed therein, condensation of some components included in the substance, or a biological activity of a portion of the substance.

When a plurality of substances become involved in the activity, the plurality of substances may be placed together in the patch PA before a reference time point. The plurality of substances may be sequentially inserted into the patch PA.

By changing environmental conditions of the patch PA, efficiency of the function of providing a space for activities other than diffusion in the patch PA may be enhanced. For example, the activity may be promoted or a start of the activity may be induced by changing a temperature condition of the patch PA or adding an electrical condition thereto.

According to FIGS. 3 and 4, a first substance SB1 and a second she SB2 placed in the patch PA may react inside the patch PA and be deformed into a third substance SB3 or generate the third substance SB3.

2.2 Channel
2.2.1 Meaning

Movement of a substance may occur between the patch PA and an external region. The substance may be moved from the patch PA to the external region of the patch PA or may be moved from the external region to the patch PA.

The patch PA may forma substance movement path or get involved in movement of the substance. More specifically, the patch PA may become involved in movement of the liquid substance SB captured in the patch PA or became involved in movement of an external substance through the liquid substance SB captured in the patch PA. The base substance BS or the additive substance AS may move out from the patch PA, or an external substance may be introduced from an external region to the patch PA.

The patch PA may provide a substance movement path. That is, the patch PA may become involved in movement of the substance and provide a substance movement channel. The patch PA may provide a substance movement channel based on unique properties of the liquid substance SB.

In accordance with whether the patch PA is connected to the external region, the patch PA may be in a state in which the liquid substance SB is movable between the patch PA and the external region or a state in which the liquid substance SB is immovable between the patch PA and the external region. When channeling between the patch PA and the external region begins, the patch PA may have unique functions.

Hereinafter, the state in which the substance is movable and the state in which the substance is immovable will be described first, and the unique functions of the patch PA will be described in detail in connection with whether the patch PA and the external region are connected.

Basically, irregular motion and/or diffusion of the substance are fundamental causes of movement of the liquid substance SB between the patch PA and the external region. However, controlling an external environmental factor (e.g., controlling a temperature condition, controlling an electrical condition, or the like) in order to control movement of a substance between the patch PA and the external region has already been described.

2.2.2 Movable State

In the state in which the substance is moveable, a flow may occur between the liquid substance SB captured in the patch PA and/or the substance placed in the external region. In the state in which the substance is movable, substance movement may occur between the liquid substance SB captured in the patch PA and the external region.

For example, in the state in which the substance is movable, the liquid substance SB or some components of the liquid substance SB may be diffused to the external region or moved due to irregular motion. Alternatively, in the state in which the substance is movable, an external substance placed in the external region or some components of the eternal substance may be diffused to the liquid substance SB in the patch PA or moved due to irregular motion.

The state in which the substance is movable may be caused by contact. The contact may refer to connection between the liquid substance SB captured in the patch PA and the external region. Contact may refer to at least a partial overlap between a flow region of the liquid substance SB and the external region. The contact may refer to the external substance being connected to at learnt a portion of the patch PA. It may be understood that the range in which the captured liquid substance SB may flow is expanded in the state in which the substance is movable. In other words, in the state in which the substance is movable, the range in which the liquid substance SB may flow may be expanded to include at least a portion of the external region of the captured liquid substance SB. For example, when the liquid substance SB is in contact with the external region, the range in which the captured liquid substance SB may flow may be expanded to include at least a portion of the external region in contact. More specifically, when the external region is an external plate, the region in which the liquid substance SB may flow may be expanded to include a region of the external plate in contact with the liquid substance SB.

2.2.3 Immovable State

In the state in which the substance is immovable, substance movement may not occur between the liquid substance SB captured in the patch PA and the external region. However, substance movement may respectively occur in the liquid substance SB captured in the patch PA and in external substance placed in the external region.

The state in which the same is immovable may be a state in which the contact is released. In other words, in the state in which contact between the patch PA and the external region is released, substance movement is not possible between the liquid substance SB remaining in the patch PA and the external region or the external substance.

More specifically, the state in which the contact is released may refer to a state in which the liquid substance SB captured in the patch PA is not connected to the external region. The state in which the contact is released may refer to a state in which the liquid substance SB is not connected to an external substance placed in the external region. For example, the state in which movement of the substance is impossible may be caused by separation between the patch PA and the external region.

In the present specification, although "movable state" has a meaning differentiated front that of "immovable state," a transition may occur between the states due to an elapse of time, an environmental change, and the like. In other words, the patch PA may be in the immovable state after being in the movable state, in the movable state after being in the immovable state, or may be in the movable state again, after being in the immovable able state after being in the movable state.

2.2.4 Differentiation of Functions
2.2.4.1 Delivery

In the present application, due to the above-described characteristics, the patch PA may deliver at least a portion of the liquid substance SB captured in the patch PA to a desired external region. The delivery of the substance may refer to separation of a portion of the liquid substance SB captured in the patch PA from the patch PA due to a predetermined condition being satisfied. The separation of the portion of the liquid substance SB may refer to the portion of the substance being extracted, emitted, or released form a region that it affected by the patch PA. This is a concept subordinate to the above-described channeling function of the patch PA, and may be understood as defining transfer (delivery) of the substance placed in the patch PA to the outside of the patch PA.

The desired external region may be another patch PA, a dried region, or a liquid region.

The redetermined condition for the delivery to occur may be set as an environmental condition such as a temperature change, a pressure change, a change in an electrical characteristic, and a change in a physical state. For example, when the patch PA is in contact with an object whose force of binding to the liquid substance SB is larger than a force of binding to the mesh structural body NS of the patch PA, the liquid substance SB may be chemically bound with the object in contact, and as a result, at least a portion of the liquid substance SB may be provided to the object.

Hereinafter, for convenience, the above-described function of the patch PA will be referred to as "delivery."

The delivery may occur between the patch PA and the external region, via the state in which the liquid substance SB is movable and the state in which the liquid substance SB is immovable between the patch PA and the external region.

More specifically, when the liquid substance SB is in the movable state, the liquid substance SB may be diffused between the patch PA and the external region or may be moved to the external region due to irregular motion. In other words, the base solution and/or the additive substance AS included in the liquid substance SB may be moved from the patch PA to the external region. In the state in which the liquid substance SB is immovable, the liquid substance SB is unable to move between the patch PA and the external region. In other words, due to a transition from the movable state to the immovable state, a portion of the substance that has moved from the patch PA tot the external region due to diffusion and/or irregular motion of the liquid substance SB become unable to nave back to the patch PA. Thus, a portion of the liquid substance SB may be provided to the external region.

The delivery may be performed due to a difference between an attractive force between the liquid substance SB and the mesh structural body NS and an attractive force between the liquid substance SB and the external region or the external substance. The attractive force may be caused by similarity between polarities or a specific binding relationship.

More specifically, when the liquid substance SB is hydrophilic and the external region or the external substance is mote hydrophilic than the mush structural body NS, at least a portion of the liquid substance SB captured in the patch PA may be provided to the external region via the movable state and the immovable state.

The delivery of the liquid substance SB may also be performed selectively. For example, when a specific binding relationship exists between some components included in the liquid substance SB and the animal substance, some of the ingredients may be selectively delivered via the state in which the substance is movable and the state in which the substance is immovable.

More specifically, when it is assumed that the patch PA provides a substance to an external plate PL, which is in a form of a flat plate, a substance that binds specifically to a portion of the liquid substance SB captured in the patch PA (e.g., a portion of a solute) may be applied on the external plate PL. In this case, the patch PA may selectively deliver a portion of the solute that binds specifically to the substance applied on the external plate PL from the patch PA to the plate PL via the movable state and the immovable state.

The delivery as a function of the patch PA will be described below according to a few examples of different regions to which the substance is moved. However, in giving the detailed description, the concepts of "release" of the liquid substance SB and "delivery" of the liquid substance SB may be interchangeably used.

Here, a case in which liquid substance SB is provided from the patch PA to a separate external plate PL will be described. For example, a case in which the substance is moved from the patch PA to a plate PL, such as a slide glass, may be taken into consideration.

As the patch PA and the plate PL come into contact, at least a portion of the liquid substance SB captured in the patch PA is diffused to the plate PL or moved due to irregular motion. When the contact between the patch PA and the plate PL is released, the portion of the substance that has been moved from the patch PA to the plate PL (that is, the portion of the liquid substance SB) become unable to move back to the patch PA. As a result, the portion of the substance may be provided from the patch PA to the plate PL. In this case, the portion of the substance being provided may be the additive substance AS. For a substance in the patch PA to be "provided" by the contact and separation an attractive force and/or binding force that acts between the substance and the plate PL should be present, and the attractive force and/or the binding force should be larger than the attractive force acting between the substance and the patch PA. Therefore if the above-described "delivery condition" is not satisfied, delivery of a substance may not occur between the PA and the plate PL.

The delivery of a substance may be controlled by providing a temperature condition or an electrical condition to the patch PA.

The movement of a substance from the patch PA to the plate PL may depend on an extent of a contact area between the patch PA and the plate PL. For example, the substance movement efficiency between the patch PA and the plate PL may be increased or decreased in accordance with an extent of an area in which the patch PA and the plate PL come into contact.

When the patch PA includes a plurality of components, only some of the components may be selectively moved to the external plate PL. More specifically, a substance that binds specifically to some of the plurality of components may be fixed to the external plate PL. In this care, the substance fixed to the external plate PL may be in a liquid or solid state, or may be fixed to a different region. In this case, a portion of the substance of the plurality of components moves to the plate PL and binds specifically to the plate PL due to contact between the patch PA and the different region, and when the patch PA is separated from the plate PL, only some of the components may be selectively released to the plate PL.

Figure 5:
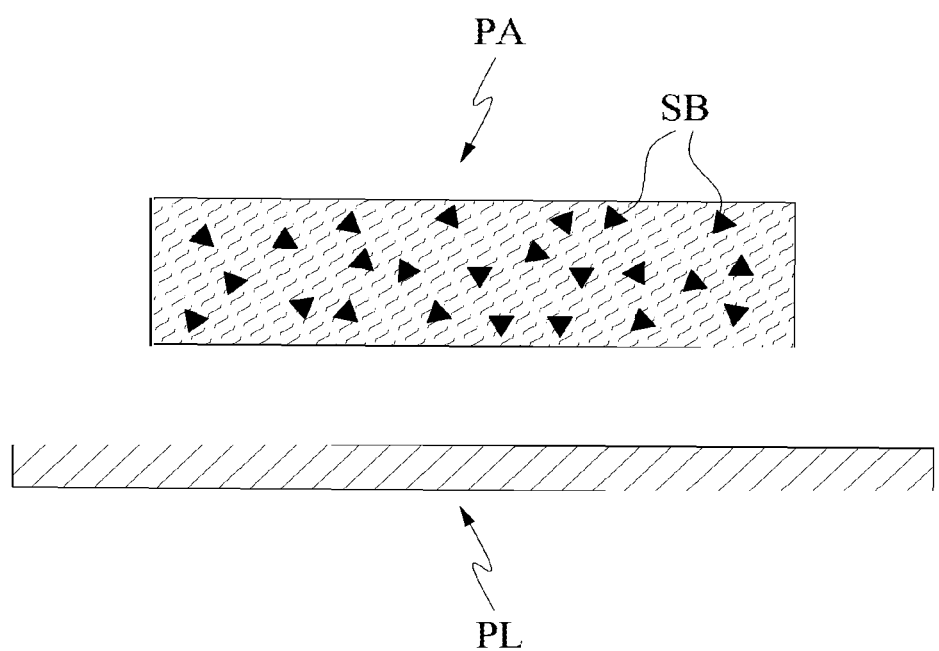
FIG. 5 illustrates providing of a substance as an example of a function of a patch according to the present application.
Figure 6:
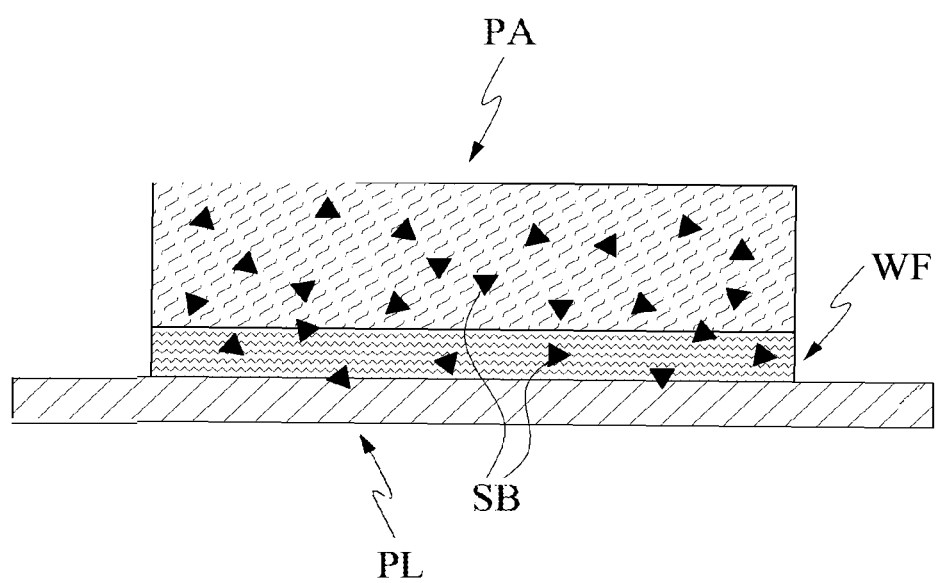
FIG. 6 illustrates providing of a substance as an example of a function of a patch according to the present application.
Figure 7:
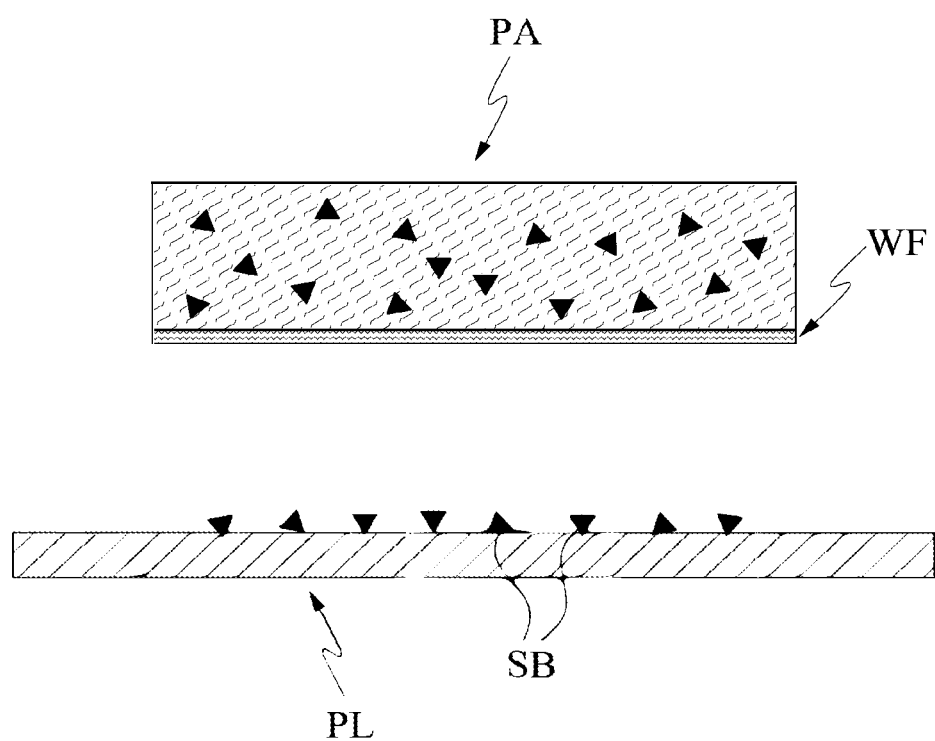
FIG. 7 illustrates providing of a substance as an example of a function of a patch according to the present application.
Figure 8:
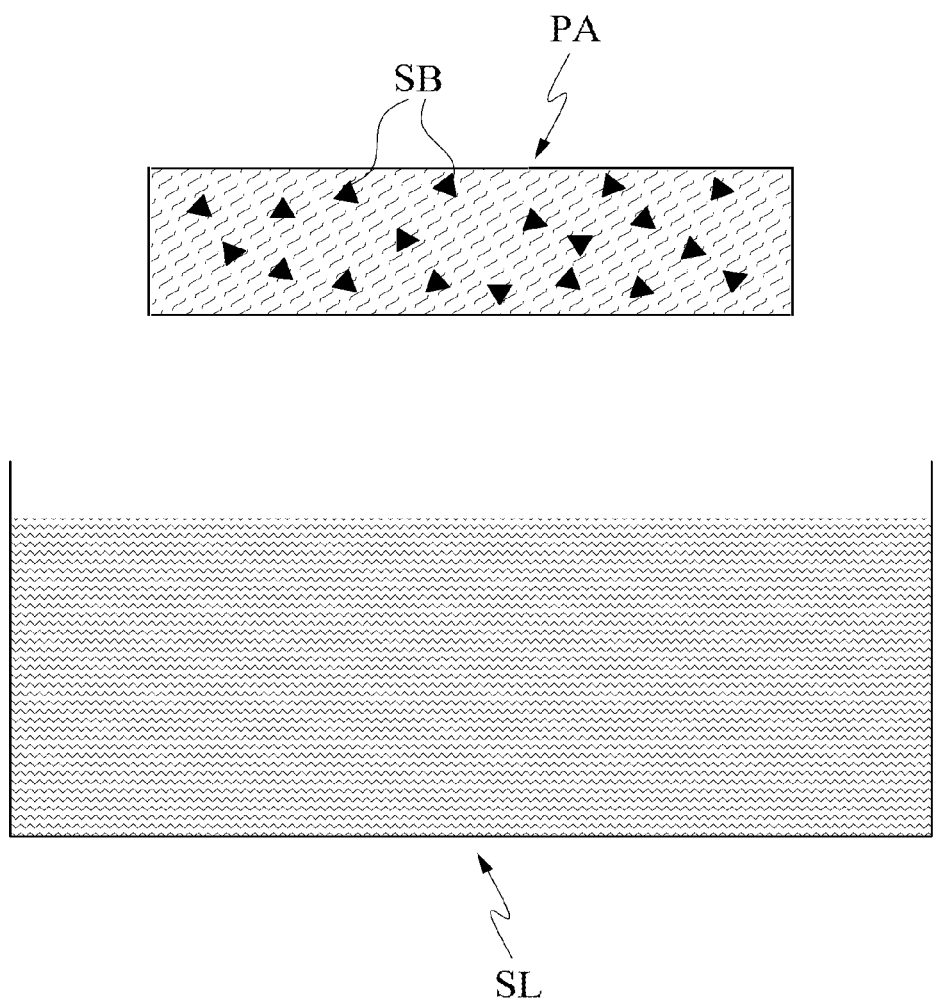
FIG. 8 illustrates providing of a substance as an example of a function of a patch according to the present application.
Figure 9:
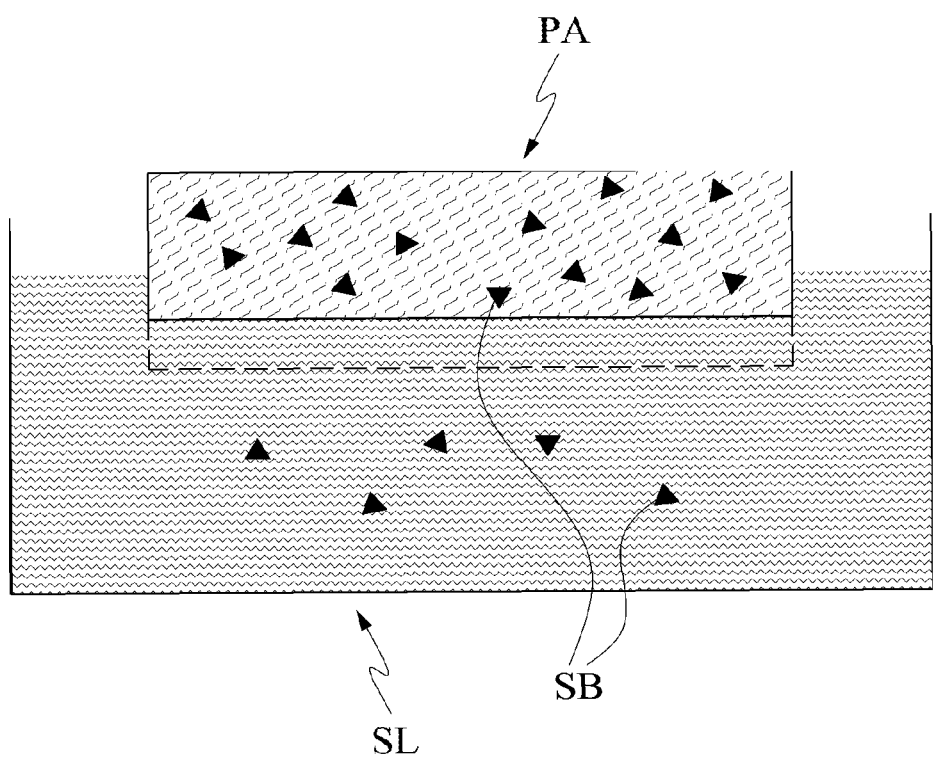
FIG. 9 illustrates providing of a substance as an example of a function of a patch according to the present application.
Figure 10:
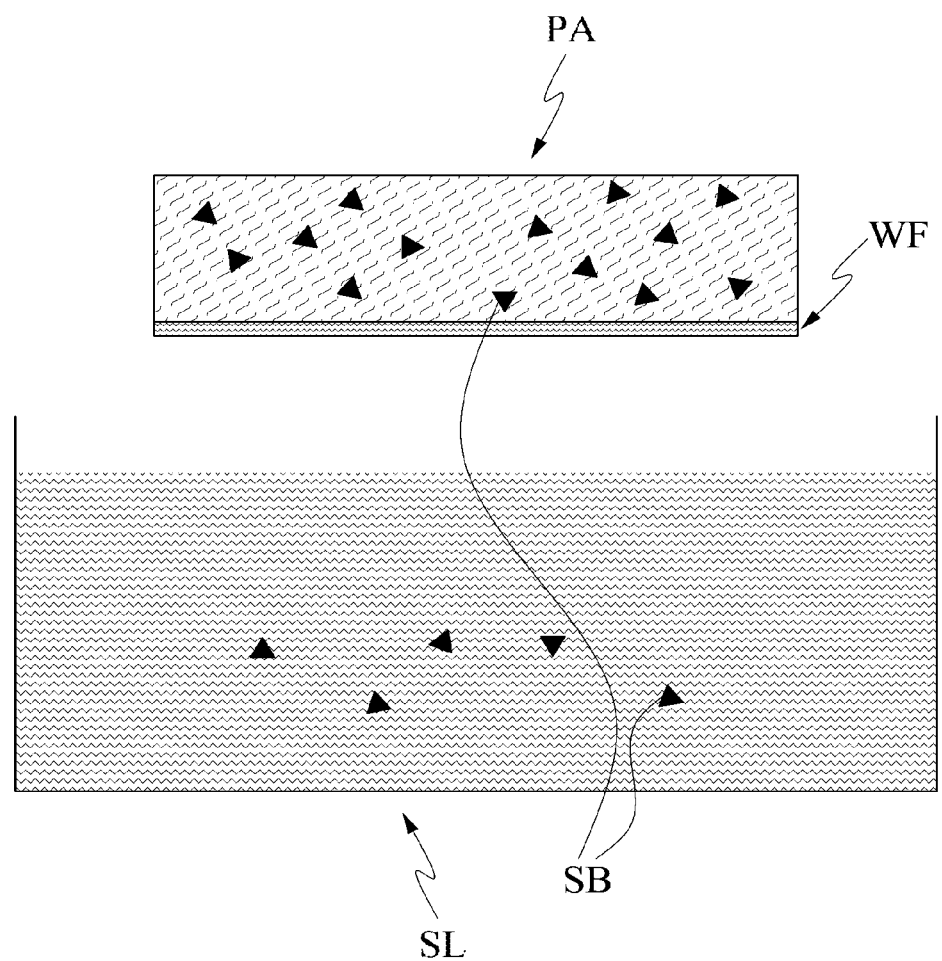
FIG. 10 illustrates providing of a substance as an example of a function of a patch according to the present application.

FIGS. 5 to 7 illustrate delivery of a substance from the patch PA to the external plate PL as an example of delivery of imbalance front among the functions of the patch PA according to the present application. According to FIGS. 5 to 7, by the patch PA coming into contact with the external plate PL, a portion of a substance contained in the patch PA may be provided to the plate PL. In this case, providing of the substance may become possible by the patch PA coming into contact with the plate so that the substance is movable. In this case, a water film WF may be formed in the vicinity of a contact surface at which the plate and the patch PA come into contact, and the substance may be movable through the formed water film WF.

Here, a case in which the liquid substance SB it provided from the patch PA to a substance having fluidity SL will be described. The substance having fluidity SL may be a liquid substance that is held in other containing space or that is flowing.

As the patch PA and the substance having fluidity come into contact (for example, the patch PA is put into a solution), at least a portion of the liquid substance SB captured in the patch PA may be diffused or moved due to irregular motion to the substance having fluidity SL. When the patch PA and the substance having fluidity SL are separated, a portion of the liquid substance SB that has been moved from the patch PA to the substance having fluidity become unable to move back to the patch PA so that a portion of the substance in the patch PA may be provided to the substance having fluidity.

The substance movement between the patch PA and the substance having fluidity SL may depend on an extent of a contact area between the patch PA and the substance having fluidity SL. For example, the substance movement efficiency between the patch PA and the substance having fluidity SL may be increased or decreased in accordance with an extent of an area at which the patch PA and the substance having fluidity SL come into contact (for example, a depth at which the patch PA is immersed into a solution or the like).

The substance movement between the patch PA and the substance having fluidity SL may be controlled through physical separation between the patch PA and the substance having fluidity.

A partial concentrations of the additive substance AS in the liquid substance SB and a partial concentration of the additive substance AS in the substance having fluidity may be different, and the additive substance AS may be provided from the patch PA to the substance having fluidity.

However, in the patch PA providing the maid substance SB to the substance having fluidity SL, the physical separation between the patch PA and the substance having fluidity SL is not essential. For example, when a force (driving force/casual force) that causes a substance to move from the patch PA to a liquid having fluidity disappears or is decreased to a reference value or lower, the movement of the substance may be stopped.

In "delivery" between the patch PA and the substance having fluidity SL, the above-described "delivery condition" between the patch PA and the substance having fluidity SL may not be required. It may be understood that substances that have already moved to the substance having fluidity SL are diffused and/or moved due to irregular motion in the substance having fluidity SL, and the substance has been provided to the substance having fluidity SL when a distance between the moved substance and the patch PA became larger a predetermined distance. Sines, while in the case of the plate PL, a movable range expanded due to the contact is extremely limited, and thus the attractive force between the patch PA and the substances the have moved to the plate PL may be significant, in the relationship between the patch PA and the substance having fluidity, a movable range expanded due to contact between the patch PA and the plate PL is relatively much wider, and thus the attractive force between the patch PA and the substances that have moved to the substance having fluidity SL is insignificant.

FIGS. 5 to 10 illustrate delivery of a substance from the patch PA to the substance having fluidity as an example of delivery of a substance from among the functions of the patch PA according to the present application. According to FIGS. 5 to 10, the patch PA may deliver a portion of a substance contained in the patch PA to an external substance having fluidity. The delivery of the portion of the contained substance may be performed by the patch PA being inserted into or coming into contact with the substance having fluidity so that substance movement is possible between the liquid substance SB agitated in the patch PA and the substance having fluidity.

Here, it is assumed that a substance is moved from the patch PA to another patch PA. In a contact region in which the patch PA and the other patch PA are in contact, at least a portion of the liquid substance B provided in the patch PA may be moved to the other patch PA.

In the contact region, the liquid substance SB provided in each patch PA they be diffused and moved to the other patch PA. In this case, due to the movement of the substance, a concertation of the liquid substance SB provided in each patch PA may be changed. Also in the present embodiment, as described above, the patch PA and the other patch PA may be separated, and a portion of the lipid substance SB in the patch PA may be provided to the other patch PA.

The substance movement between the patch PA and the other patch PA may be performed through a change in an environmental condition at including a change in a physical state.

The substance movement between the patch PA and another patch PA may depend on an extent of a contact area between the patch PA and the other patch PA. For example, the substance movement efficiency between the patch PA and the other patch PA may be increased or decreased in accordance with an extent of an area where the patch PA comes into contact with the other patch PA.

Figure 11:
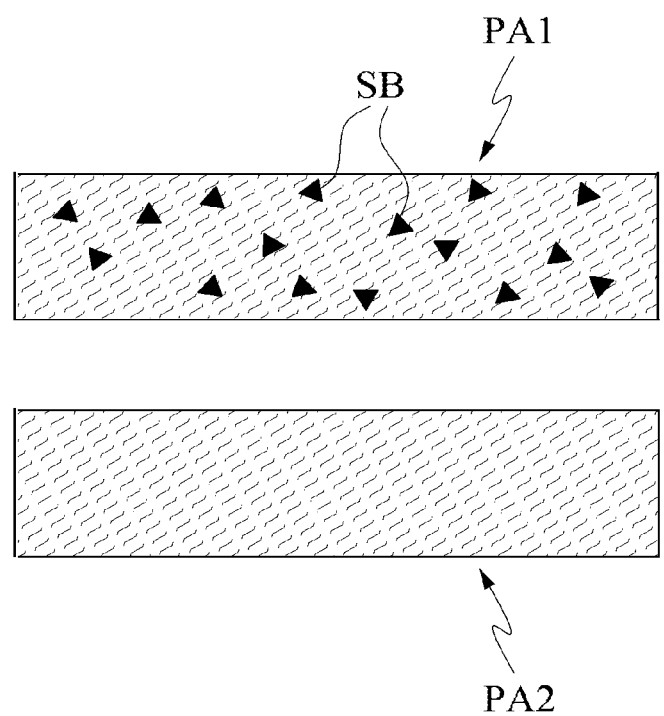
FIG. 11 illustrates providing of a substance as an example of a function of a patch according to the present application.
Figure 12:
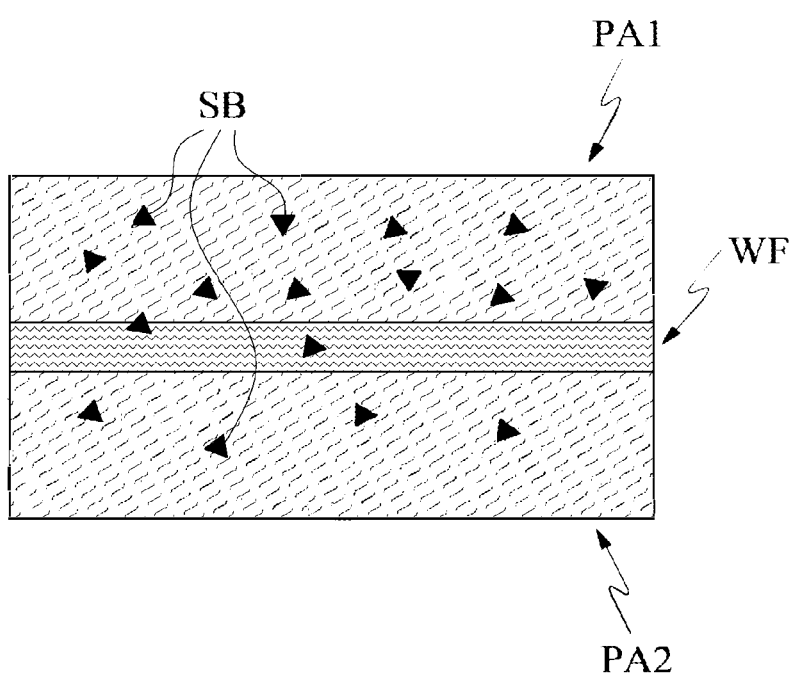
FIG. 12 illustrates providing of a substance as an example of a function of a patch according to the present application.
Figure 13:
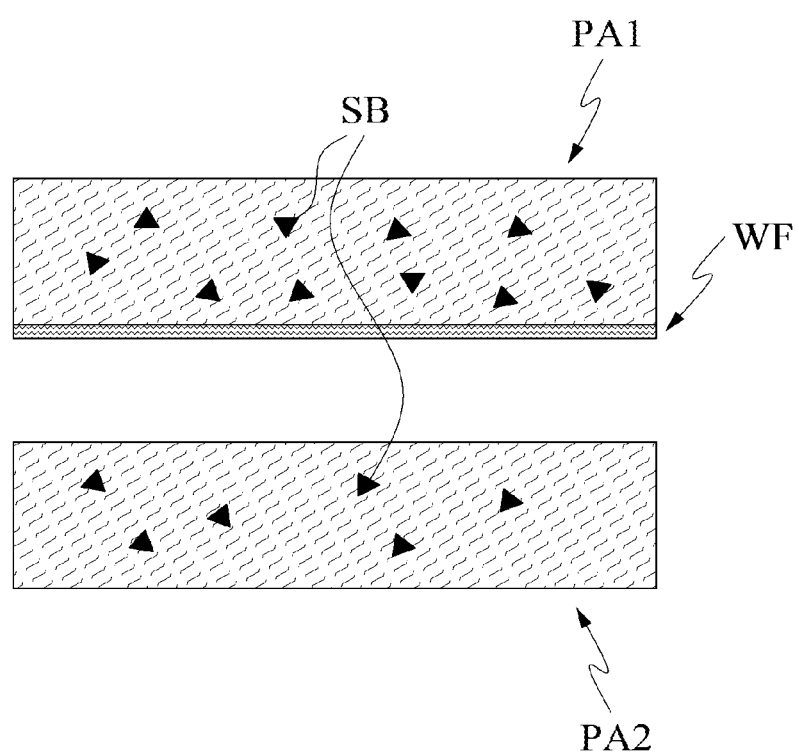
FIG. 13 illustrates providing of a substance as an example of a function of a patch according to the present application.

FIGS. 11 to 13 illustrate delivery of a substance from a patch PA1 to another patch PA2 as an example of delivery of a substance among the functions of the patch PA according to the present application. According to FIGS. 11 to 13, the patch PA1 may deliver a portion of a substance contained in the patch PA1 to the other patch PA2. The delivery of the portion of the substance may be performed by the patch PA1 coming into contact with the other patch PA2 and becoming a state in which a lipid substance SB captured in the patch PA1 and a substance captured in the other patch PA2 are exchangeable.

2.2.4.2 Absorption

Prior to description, it should be noted that, among the functions of the patch PA according to the present application, "absorption" may be managed similarly as the above-described "delivery" in some embodiments. For example, in a case in which a substance moves due to a concentration differences between substances, the "absorption" may be similar to the "delivery" in that a concentration of the liquid substance SB, particularly, a concentration of the additive substance AS, may be changed to control a direction in which the substance is moved. The "absorption" may also be similar to "delivery" in terms of controlling movement and selective absorption of a substance through a release of physical contact with the patch PA, and this may be clearly understood by those of ordinary skill in the art to which the present application pertains.

Due to the above-described characteristics, the patch PA according to the present application may capture an external substance. The patch PA may pull in an external substance present outside a region defined by the patch PA toward a region affected by the patch PA. The pulled external substance may be captured along with the liquid substance SB of the patch PA. The pulling of the external substance may be caused by attractive force between the external substance and the liquid substance SB already captured in the patch PA. Alternatively, the pulling of the external substance may be caused by an attractive force between the external substance and a region of the mesh structural body NS not occupied by the liquid substance SB. The pulling of the external substance may be caused by a force of surface tension.

Hereinafter, for convenience, the above-described function of the patch PA will be referred to as "absorption." Absorption may be understood as a concept subordinate to the above-described channeling function of the patch PA, the concept defining movement of an external substance to the patch PA.

The absorption may occur by the patch PA via a state in which the substance is movable and a state in which the substance is immovable.

A substance that is absorbable by the patch PA may be in a liquid or solid state. For example, when the patch PA comes into contact with an external substance including a solid state substance, absorption of the substance may be performed due to an attractive force between the solid state substance included in the external substance and the liquid substance SB placed in the patch PA. As another example, when the patch PA comes into contact with a liquid external substance, the absorption may be performed due to binding between the liquid external substrate and the liquid substance SB placed in the patch PA.

The external substance absorbed into the patch PA may be moved to the inside of the patch PA through the microcavities of the mesh structural body NS forming the patch PA or may be distributed on a surface of the patch PA. Positions at which the external substance is distributed may be set on the basis of a molecular weight or a particle size of the external substance.

While the absorption is performed, the form of the patch PA may be changed. For example, the volume, color, and the like of the patch PA may be changed. While the absorption into the patch PA is being performed, the absorption into the patch PA may be activated or delayed by adding external conditions such as a temperature change and a physical state change to an absorption environment of the patch PA.

The absorption will be described below as a function of the patch PA according to some examples of an external region that provides a substance to be absorbed into the patch PA when the absorption occurs.

Hereinafter, it will be assumed that the patch PA absorbs an external substance from a external plate PL. An example of the external plate may include a plate PL in which the external substance may be placed while the external substance is not absorbed thereinto.

A substance may be applied on the external plate PL. Particularly, a substance may be applied in a form of powder on the plate PL. The substance applied on the plate PL may be a single component or a mixture of a plurality of components.

The plate PL may have the shape of a flat plate. The shape of the plate PL may be deformed for improvement in ability to contain the substance or the like. For example, a well may be formed to improve the ability to contain the substance, a surface of the plate PL may be deformed by engraving or embossing, or a patterned plate PL may be used to improve contact with the patch PA.

The absorption of a substance from the plate PL by the patch PA according to the present application may be performed through contact between the plate PL and the patch PA. In this case, in a contact region in the vicinity of a contact surface between the plate PL, and the patch PA, a water film WF may be formed due to the liquid substance SB captured in the patch PA and/or the substance applied on the plate PL. When the water film (aquaplane, hydroplane) WF is formed in the contact region, the substance applied on the plate PL may be captured by the water film WF. The substance captured in the water film WF may freely flow within the patch PA.

When the patch PA is spaced a predetermined distance or more apart and separated from the plate PL, the water film WF may be moved along with the patch PA, and the substance applied on the plate PL may be absorbed into the patch PA. The substance applied on the plate PL may be absorbed into the patch PA as the patch PA is separated a predetermined distance or more apart from the plate PL. When the patch PA and the plate PL are spaced apart and separated, the liquid substance SB provided to the patch PA may not be moved to the plate PL, or only an insignificant amount thereof may be absorbed into the patch PA.

A portion of or the entire substance applied on the plate PL may react specifically with a portion of or the entire substance captured in the patch PA. In this aspect, absorption of a substance from the plate PL by the patch PA may be selectively performed. Particularly, the absorption may be performed selectively when the patch PA has a stronger attractive force than the plate PL with respect to a portion of the substance captured in the patch PA.

As an example, a portion of the substance may be fixed to the plate PL. In other words, a portion of the substance may be fixed to the plate PL while another portion of the substance is applied to have fluidity or not be fixed. In this case, when the patch PA and the plate PL are brought into contact and separated, the substance, excluding the portion of the substance fixed to the plate PL of the substance applied on the plate PL, may be selectively absorbed into the patch PA. Instead, the selective absorption may also occur due to polarities of a substance placed on the plate PL and a substance captured in the patch PA regardless of whether the substance is fixed.

As another example, when the liquid substance SB captured in the patch PA is bound specifically to at least a portion of a substance applied on the plate PL, only the portion of the substance applied on the plate PL bound specifically to the liquid substance SB may be absorbed into the patch PA when the patch PA is brought into contact with and then separated from the substance applied on the plate PL.

As yet another example, a portion of the substance applied on the plate PL may react specifically with a substance fixed to the plate PL in advance. In this case, only a remaining substance, excluding the substance that reacts specifically with the substance fixes to the plate PL in advance of the substance being applied to the plate PL, may be absorbed into the patch PA.

Figure 14:
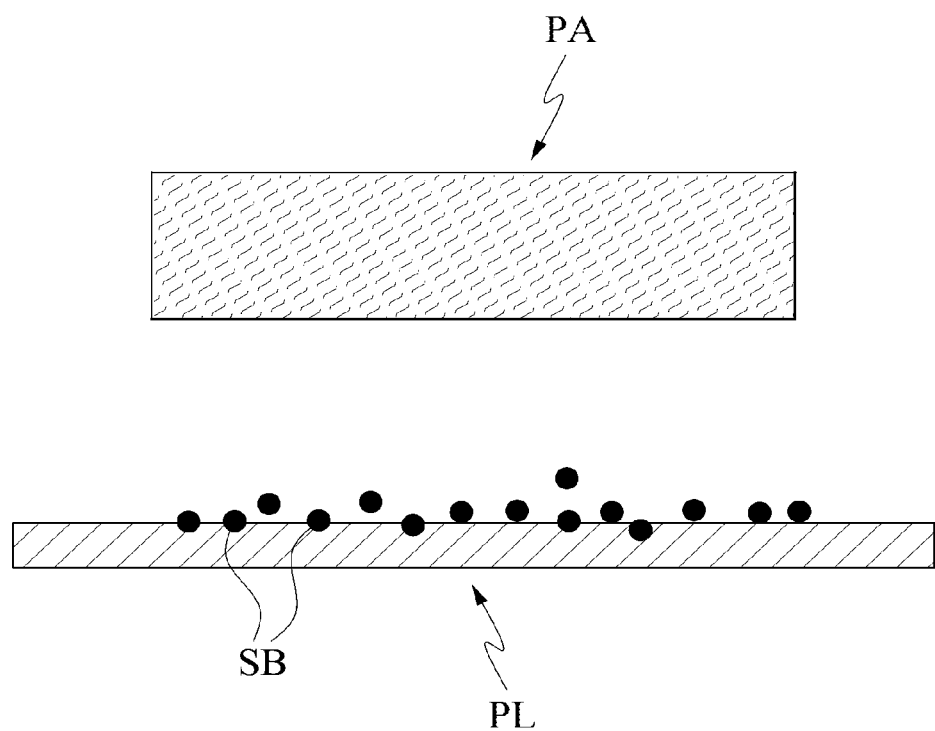
FIG. 14 illustrates absorbing of a substance as an example of a function of a patch according to the present application.
Figure 15:
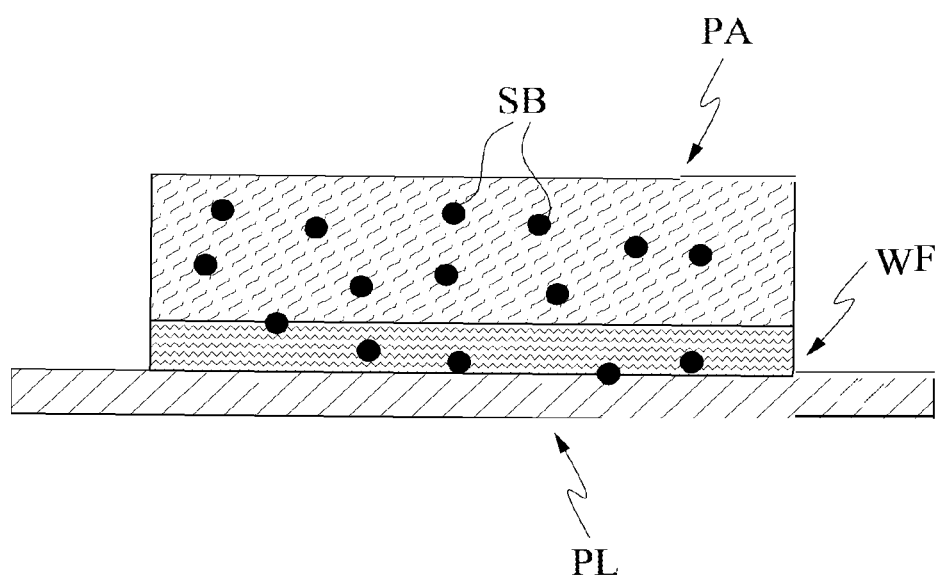
FIG. 15 illustrates absorbing of a substance as an example of a function of a patch according to the present application.
Figure 16:
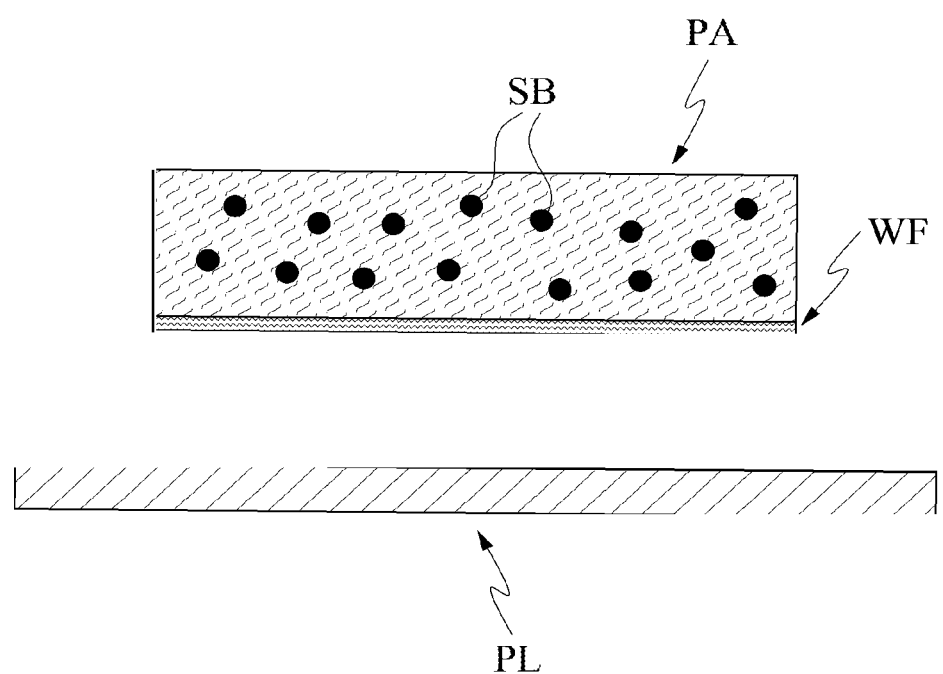
FIG. 16 illustrates absorbing of a substance as an example of a function of a patch according to the present application.

FIGS. 14 to 16 illustrate absorption of a substance from an external plate PL by the patch PA as an example of absorption of a substance from among the functions of the patch PA according to the present application. According to FIGS. 14 to 16, the patch PA may absorb a portion of a substance placed on the external plate PL from the external plate PL. The absorption of the substance may be performed by the patch PA corning into contact with the external plate PL, the water film WF being formed in the vicinity of a contact region between the external plate PL and the patch PA, and the substance being moveable to the patch PA through the water film WF.

Here, it will be assumed that a substance is absorbed into the patch PA from the substance having fluidity SL. The substance having fluidity may refer to a liquid external substance that is held in other containing space or that is flowing. More specifically, by having an environment in which the substance having fluidity SL and the liquid substance SB captured in the patch PA may flow to and from each other, a portion of or the entire substance having fluidity SL may be absorbed into the patch PA. In this case, the environment in which the substance having fluidity SL and the liquid substance SB may flow to and from each other may be formed by the patch PA coming into contact with at least a portion of the substance having fluidity SL.

When the patch PA comes into contact with the substance having fluidity SL, the patch PA may be in a state in which a substance is movable from the substance having fluidity SL. When the patch PA is separated from the substance having fluidity SL, at least a portion of the substance having fluidity SL may be absorbed into the patch PA.

The absorption of a substance into the patch PA from the substance having fluidity SL may depend on a concentration difference between the substance captured in the patch PA and the substance having fluidity SL. In other words, when the concentration of the liquid substance SB captured in the patch PA with respect to a predetermined additive substance AS is lower than the concentration of the substance having fluidity SL with respect to the predetermined additive substance AS, the predetermined additive substance AS may be absorbed into the patch PA.

When a substance it absorbed into the patch PA from the substance having fluidity SL, in addition to the absorption depending on the concentration difference while the patch PA and the substance having fluidity SL are in contact as described above, the absorption into the patch PA may also be controlled by adding an electrical factor or changing a physical condition. Further, without direct contact between the substance captured in the patch PA and a substance to be absorbed, the absorption of a substance may also be performed through indirect contact therebetween via a medium.

Figure 17:
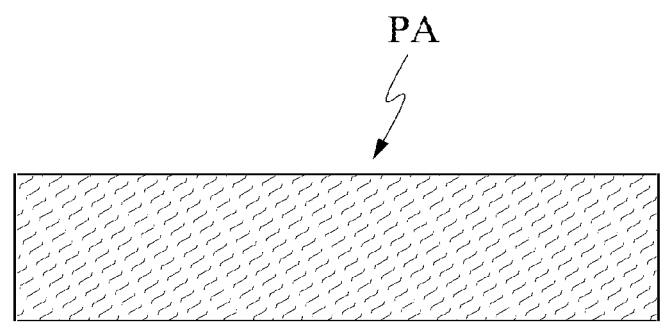
FIG. 17 illustrates absorbing of a substance as an example of a function of a patch according to the present application.
Figure 17:
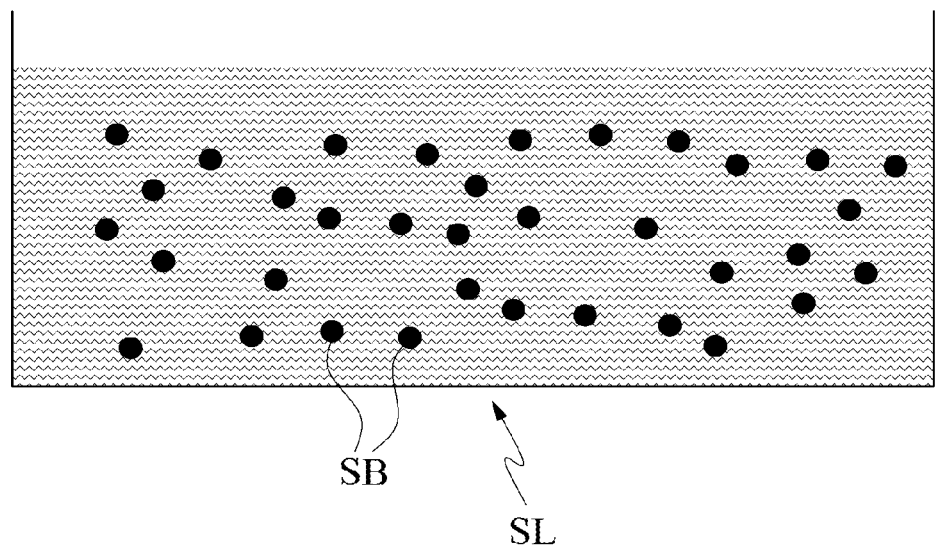
Figure 18:
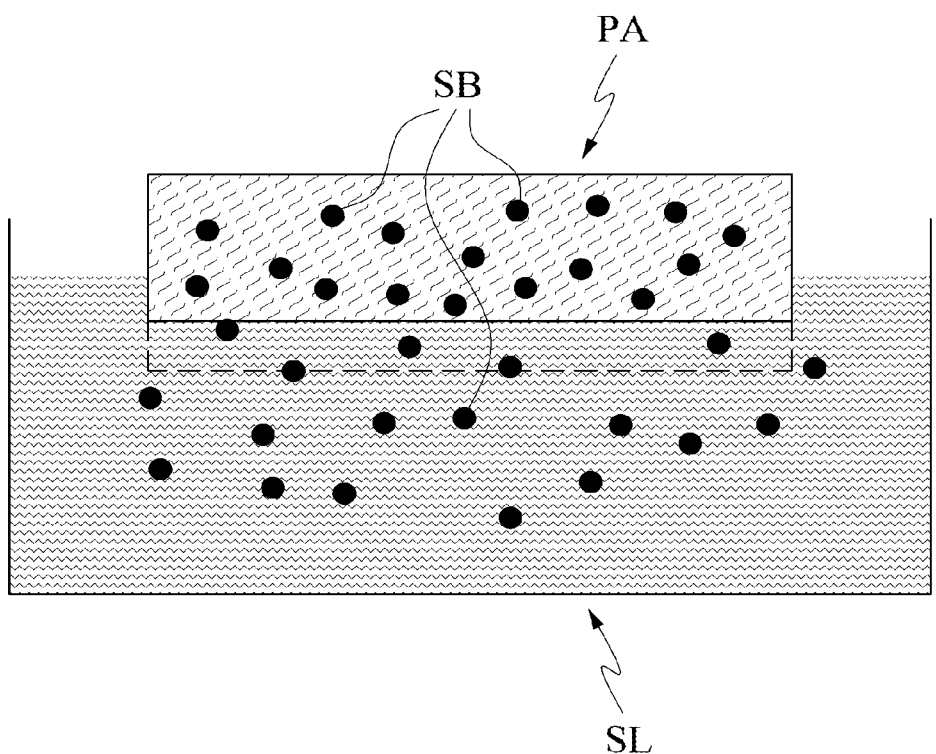
FIG. 18 illustrates absorbing of a substance as an example of a function of a patch according to the present application.
Figure 19:
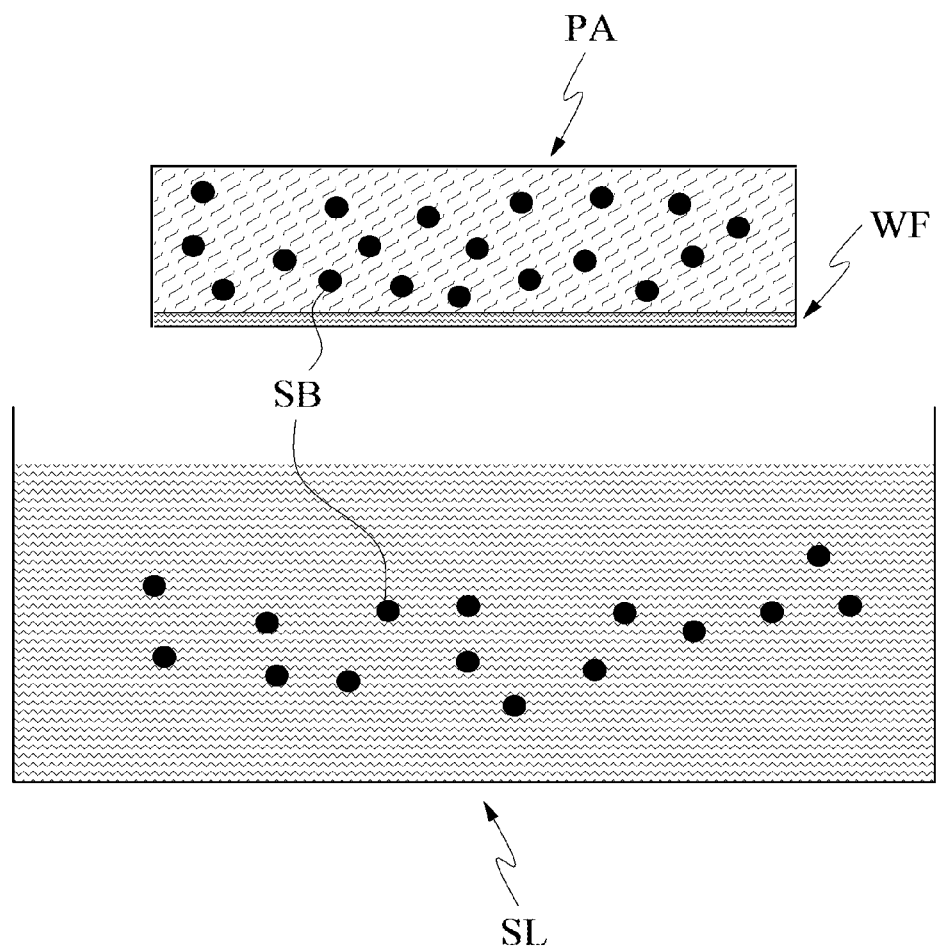
FIG. 19 illustrates absorbing of a substance as an example of a function of a peach according to the present application.

FIGS. 17 to 19 illustrate absorption of a substance from the substance having fluidity SL by the patch PA as an example of absorption of a substance from among the functions of the patch PA according to the present application. According to FIGS. 17 to 19, the patch PA may absorb a portion of the substance having fluidity SL. The absorption of a substance may be performed by the patch PA being immersed into the substance having fluidity SL or coming into contact with the substance having fluidity SL an that the liquid substance SB captured in the patch PA and the substance having fluidity SL are movable to and from each other.

Here, it will be assumed that the patch PA absorbs an external substance from another patch PA.

The absorption of an external substance from another patch PA by the patch PA may be performed due to a difference in binding force between the absorbed external substance and the substance already captured in the patch PA and between the absorbed eternal substance and the external substance not absorbed into the patch PA. For example, when the absorbed substance exhibits hydrophilic property, due patch PA exhibits hydrophilic property, and an attractive force between the absorbed substance and the patch PA is stronger than an attractive force between the other patch PA and the absorbed substance (that is, when the patch PA is more hydrophilic than the other patch PA), at least a portion of the external substance may be absorbed into the patch PA when the patch PA and the other patch PA are separated after being brought into contact.

Figure 20:
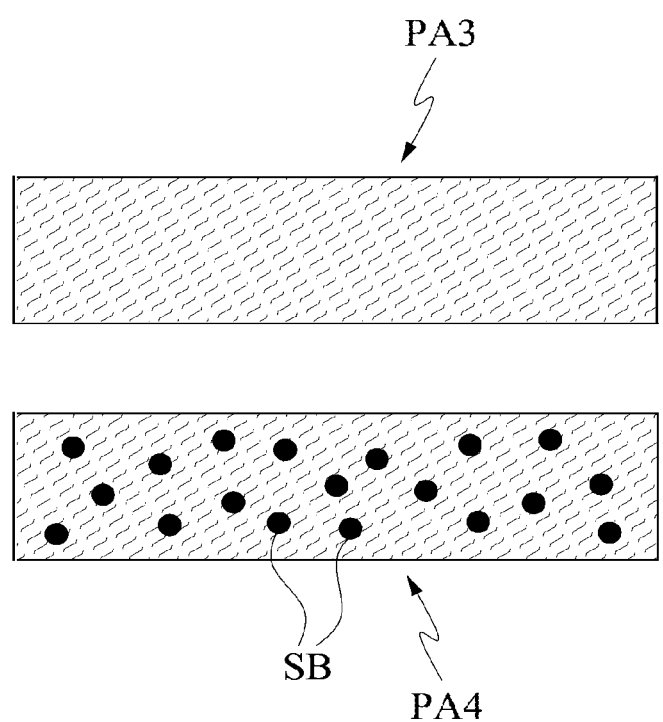
FIG. 20 illustrates absorbing of a substance as an example of a function of a patch according to the present application.
Figure 21:
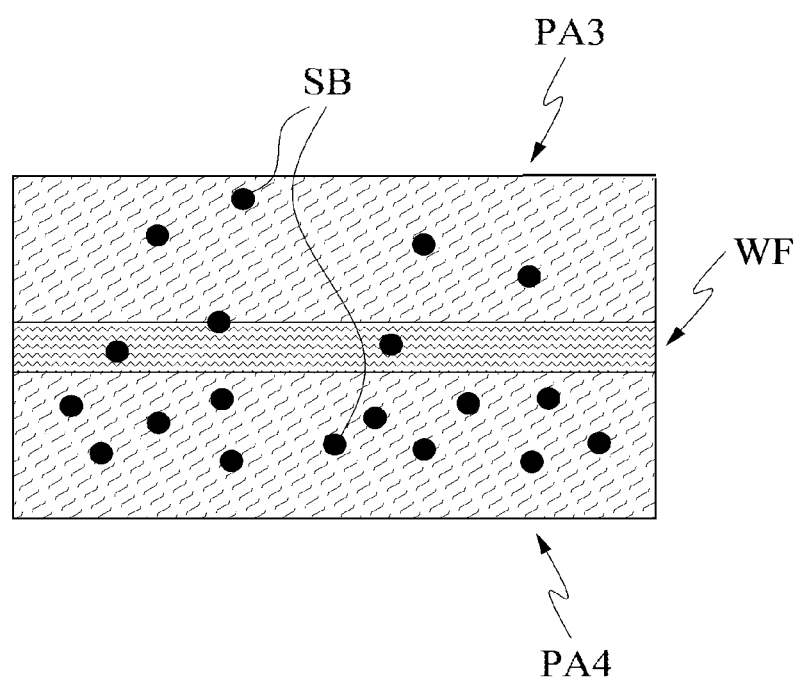
FIG. 21 illustrates thrashing of a substance as an example of a function of a patch according to the present application.
Figure 22:
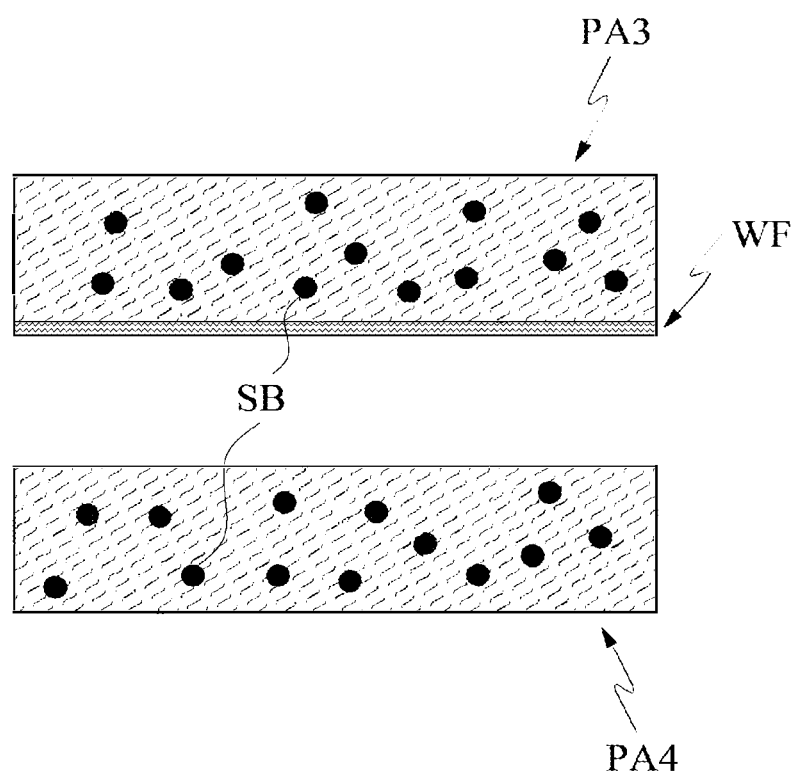
FIG. 22 illustrates thrashing of a substance as an example of a function of a patch according to the present application.

FIGS. 20 to 22 illustrate absorption of a substance from another patch PA4 by a patch PA3 as an example of absorption of a substance among the functions of the padre PA according to the present application. According to FIGS. 20 to 22, the patch PA3 may absorb a portion of a substance placed in the outer patch PA4. The absorption of the substance may be performed by the patch PA3 coming into contact with the other patch PA4 so that a liquid substance SB captured in the patch PA3 and a liquid substance SB captured in the other patch PA4 are exchangeable.

A binding force of the patch PA to the external substance absorbed thereinto may be changed in accordance with a proportion of a frame structural body of the three-dimensional mesh structural body NS constituting the patch PA with respect to the total volume of the patch PA. For example, as the proportion of a volume occupied by the frame structural body in the entire patch PA increases, the amount of substance captured in the structural body may be reduced. In this case, a binding force between the patch PA and a target substance may be reduced due to a reason such as reduction in a contact area between the target substance and the substance captured in the patch PA.

In relation to this, ratios of materials that constitutes the mesh structural body NS may be adjusted during manufacturing process of the patch PA so that polarity of the patch PA is controlled. For example, in the case of a patch PA manufactured using agarose, a concentration of the agarose may be controlled to adjust a degree of the absorption.

When the certain region has a weaker binding force than the patch PA with aspect to a substance provided from the patch PA, and the patch PA and another patch PA are brought into contact and then separated, the absorbed external substance may be separated from the other patch PA along with the patch PA.

2.2.4.3 Providing of Environment

Due to the above-described characteristics, the patch PA according to the present application may perform a function of adjusting an environmental condition of a desired region. The patch PA may provide an environment due to the patch PA to the desired region.

The environmental condition due to the patch PA may depend on the liquid substance SB captured in the patch PA. The patch PA may create a desired environment in a substance placed in an external region on the basis of characteristics of a substance accommodated in the patch PA or for a purpose of making the environment correspond to characteristics of the substance accommodated in the patch PA.

The adjustment of the environment may be understood as changing an environmental condition of the desired region. The changing of the environmental condition of the desired region may be implemented in a form in which a region affected by the patch PA is expanded to include at least a portion of the desired region or a form in which an environment of the patch PA is shared with the desired region.

Hereinafter, for convenience, the above-described function of the patch PA will be referred to as "providing of an environment."

The providing of an environment by the patch PA may be performed in a state in which a substance is movable between the patch PA and an external region subject to provide the environment. The providing of an environment by the patch PA may be performed through contact. For example, when the patch PA castes into contact with a desire region (for example, an external substance, a plate PL, or the like), a specific environment may be provided to the desired region by the patch PA.

The patch PA may adjust as environment of a target region TA by providing an environment with an appropriate pH, osmotic pressure, humidity level, concentration, temperature, and the like. For example, the patch PA may provide fluidity (liquidity) to the target region TA or a target substance. Such providing of fluidity may occur due to movement of a portion of a substance captured in the patch PA. A moist environment may be provided to the target region TA through the liquid substance SB or the base substance BS captured in the patch PA.

The environmental factors provided by the patch PA may be constantly maintained in accordance with a purpose. For example, the patch PA may provide homeostasis to the desired region. As another example, as a result of providing an environment, the substance captured in the patch PA may be adapted to an environmental condition of the desired region.

The providing of an environment by the patch PA may result from diffusion of the liquid substance SB included in the patch PA. That is, when the patch PA and the desired region come into contact, a substance may be movable through a contact region that is formed due to contact between the patch PA and the drained region. In relation to this, an environmental change due to an osmotic pressure, an environmental change due to a change in ionic concentration, providing of a moist environment, and a change in a pH level may be implemented in accordance with a direction in which the substance is diffused.

Figure 23:
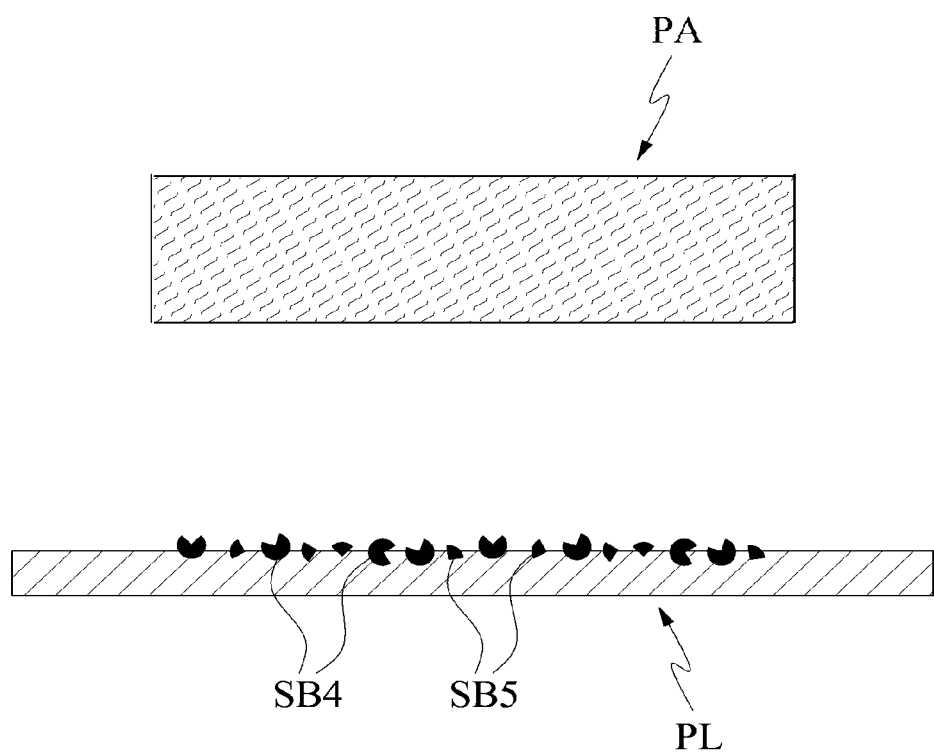
FIG. 23 illustrates providing of an environment as an example of a function of a patch according to the present application.
Figure 24:
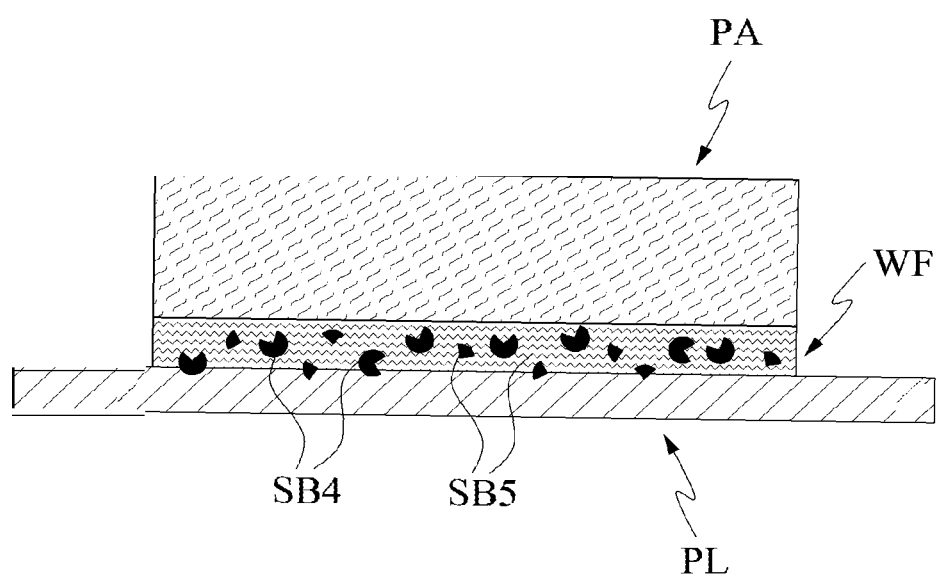
FIG. 24 illustrates providing of an environment as an example of a function of a patch according to the present application.
Figure 25:
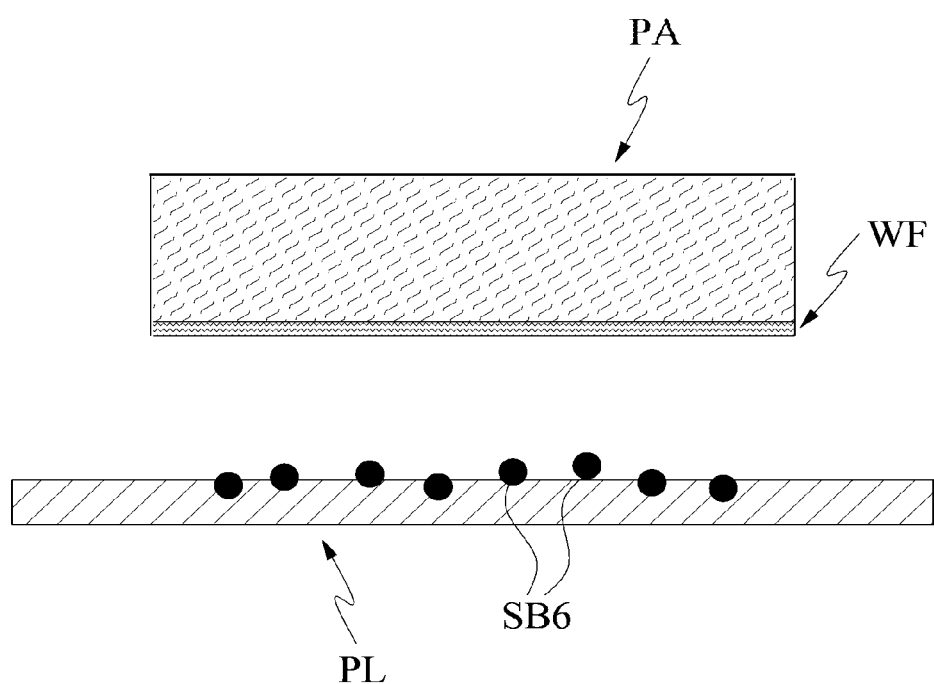
FIG. 25 illustrates providing of an environment as an example of a function of a patch according to the present application.

FIGS. 23 to 25 illustrate providing of a predetermined environment to an external plate PL by the patch PA at an example of providing of an environment among the functions of the patch PA according to dot present application. According to FIGS. 23 to 25, the patch PA may provide a predetermined environment to an external plate PL on which a fourth substance SB4 and a fifth substance SB5 are placed. For example, the patch PA may provide a predetermined environment to the plate PL for the fourth substance SB4 and the fifth substance SB5 to react and form a sixth substance SB6. The providing of the environment may be performed by the patch PA coming into contact with the plate PL so that a water film WF is formed in the vicinity of a contact region and the fourth substance SB4 and the fifth substance SB5 are captured in the water film WF.

3. Application of Patch

The patch PA according to the present application may be implemented to perform various functions by suitably applying the above-described functions of the patch PA.

The technical spirit of the present application will be described below by disclosing some embodiments. However, the technical scope to which functions of the patch PA disclosed by the present application are applied may be interpreted in a broad sense within the scope that may be easily derived by those of ordinary skill in the art, and the scope of the present application should not be interpreted as being limited by the embodiments disclosed herein.

3.1. In-Patch

The patch PA may provides reaction region for a substance. In other words, a reaction of a substance may occur in at least a portion of a spatial region affected by the patch PA. In this case, the reaction of a substance may be a reaction between liquid substances SB captured in the patch PA and/or a reaction between the captured liquid substance SB and a substance provided from the outside of the patch PA. The providing of a reaction region for a substance may activate or promote a reaction of a substance.

In this case, the liquid substance SB captured in the patch PA may include at least one of a substance added upon manufacturing the patch PA, a substance additive into the patch PA after the manufacturing of the patch PA and contained in the patch PA, and a substance temporarily caged in the patch PA. In other words, regardless of a form in which a substance is captured in the patch PA, any substance captured in the patch PA at a time point at which a reaction in the patch PA is activated may react in the patch PA. Further, a substance injected after the manufacturing of the patch PA may also act as a reaction initiator.

The providing of a reaction region for a reaction related to the mid substance SB captured in the patch PA may be a concept subordinate, in terms of embodiment, to the above-described Section 2.1.3 (that is, providing of reaction space). Alternatively, the providing of a reaction region for a reaction related to the liquid substance SB captured in the patch PA may consist of multiple concepts that perform combined functions of the above-described Section 2.1.3 and Section 2.2.4.2 (that is, absorption). The providing of a reaction region for a reaction related to the liquid substance SB captured in the patch PA is not limited thereto and may be implemented in the form in which two or more functions are combined.

3.1.1. First Embodiment

Hereinafter, description will be given by assuming that the function of absorption into the patch PA and the function of providing of a reaction space (hereinafter referred to as "providing function") are performed by a single patch PA. In this case, the absorption function and the providing function may be simultaneously-performed functions, functions performed at different time points, or functions sequentially performed to perform another function. The patch PA further including other functions in addition to the absorption and providing functions may also be considered as belonging to the present embodiment.

As described above, the patch PA may perform a function of capturing a substance, and the substance may have fluidity even when the substance is captured. When sane components of the liquid substance SB are non-uniformly distributed, the non-uniform components may be diffused. Even when components of the liquid substance SB are uniformly distributed, the liquid substance SB may have a predetermined level of mobility due to irregular motion of particles. In this case, a reaction between substances, for example, specific binding between substances, may occur inside the patch PA.

For example, in the patch PA, in addition to a reaction between captured substances, a reaction in a form in which a substance having fluidity that is newly captured in the patch PA and the substance that has been captured in the patch PA bind specifically to each other may also be possible.

The reaction between the substance having fluidity and the substance that has been captured in the patch PA may also occur after the substance patch bating separated from an space that has heat provided. For example, after the patch PA absorbs the substance having fluidity from an arbitrary space, the patch PA may be separated from the arbitrary space, and a reaction between the absorbed substance and the substance that has been captured in the patch PA may occur in the patch PA.

In addition, the patch PA may allow a ruction of a substance captured therein to occur by performing the absorption function with respect to a substance having fluidity. In other words, the absorption of the substance having fluidity by the patch PA may act as a trigger for a reaction between the absorbed substance and the substance that has been captured in the patch PA. The reaction may occur inside a space defined by the patch PA.

A composition of the liquid substance SB captured in the patch PA may be changed due to the reaction occurring inside the patch PA. When, particularly, a substance captured inside the patch PA is a compound, a chemical composition thereof may be changed before and after a reaction. Alternatively, a composition distribution of a substance may be changed in accordance with a position of the substance in the patch PA. For example, this may be due to diffusion or particles having an attractive force specific to another substance.

When the composition of the liquid substance SB is clanged due to a reaction inside the patch PA, a portion of the substance may be absorbed into the patch PA due to a concentration difference between the patch PA and a substance outside the patch PA (when a substance in contact with the patch PA is present, the corresponding substance), or the substance may be released from the patch PA to the substance outside the patch PA.

3.1.2 Second Embodiment

Hereinafter, an embodiment in which the containing function of the patch PA and the function of providing of a reaction space for a substance are performed together for at least a predetermined amount of time will be described. More specifically, the patch PA may perform a function of providing a space for at least a portion of the liquid substance SB contained in the patch PA to react.

The patch PA may contain a substance and provide a reaction space for the contained substance. In this case, the reaction space provided by the patch PA may be the microcavities formed by the mesh structural body NS of the patch PA or a surface region of the patch PA. Particularly, when a substance contained in the patch PA and a substance applied an a surface of the patch PA react, the reaction space may be the surface region of the patch PA.

The reaction space provided by the patch PA may serve to provide a specific environmental condition. While a reaction occurs in the liquid substance SB placed in the patch PA, an environmental condition of the reaction may be adjusted by the patch PA. For example, the patch PA may serve as a buffer solution.

By containing a substance through a mesh structure, the patch PA does not require a container, separately. When the reaction space of the patch PA is a surface of the patch PA, a reaction may be easily observed through the surface of the patch PA. For this, the shape of the patch PA may be deformed into a shape that facilitates the observation.

The liquid substance SB contained in the patch PA may be denaturalized or react with a different type of substance. The composition of the liquid substance SB contained in the patch PA may be changed with time.

The reaction may refer to a chemical reaction in which a chemical formula is changed, a physical state change, or a biological reaction. In this case, the liquid substance SB contained in the patch PA may be a substance formed of a single component or a mixture including a plurality of components.

3.2 Providing of Movement Path (Channeling)

Hereinafter, the patch PA that performs a function of providing a substance movement path will be described. More specifically, an described above, the patch PA may capture, absorb, release, and/or contain a substance having fluidity. Various embodiments of the patch PA that performs the function of providing a substance movement path may be implemented by each of the above-described functions of the patch PA or a combination thereof. However, a few embodiments will be disclosed for a better understanding.

3.2.1 Third Embodiment

The patch PA may be implemented to perform functions described in Section 2.2.4.1 (that is, the section related to delivery) and Section 2.2.4.2 (that is, the section related to absorption) among the above-described functions of de patch PA. In this case, the absorption function and the delivery function may be provided together or sequentially provided.

The patch PA may perform the absorption and delivery function/together to provide a substance movement path. Particularly, the patch PA may absorb an external substance and provide the absorbed external substance to an external region, thereby providing a movement path to the enteral substance.

The providing of the movement path of the external substance by the patch PA may be performed by absorbing the external substance and releasing the external substance. More specifically, the patch PA may come into contact with the external substance, absorb the external substance, come into contact with the external region, and deliver the external substance to the external region. In this case, the capturing of the external substance and the delivery of the captured external substance to the external region by the patch PA may be performed through a process similar to those of the above-described absorption and delivery.

The external substance absorbed into the patch PA and provided may be in a liquid phase or a solid phase.

In this way, the patch PA may allow a portion of the external substance to be provided to another external substance. The external substance and the other external substance may simultaneously come into contact with the patch PA. The external substance and the other external substance may come into contact with the patch PA at different time points.

The external substance and the other external substance may come into contact with the patch PA at different time points. When the external substances come into contact with the patch PA at different time points, the external substance may come into contact with the patch PA first, and after the external substance and the patch PA are separated, the patch PA and the other external substance may come into contact. In this case, the patch PA may temporarily contain a substance captured from the external substance.

The patch PA may simultaneously provide a substance movement path and additionally provide a time delay. The patch PA may perform a function of suitably adjusting an amount of substance provided to another external substance and a speed of such providing.

Such a series of processes may be carried out in one direction with respect to the patch PA. As a specific example, absorption of a substance may be performed through a surface of the patch PA, an environment may be provided in an inner space of the patch PA, and the substance may be released through another surface facing the surface.

3.2.2 Fourth Embodiment

The patch PA may perform the absorbing and releasing of a substance among the above-described functions of the patch PA and the providing of a reaction space for the substance simultaneously. In this case, the absorption and release of the substance and the providing of the reaction space may be performed simultaneously or sequentially.

According to an embodiment, in performing the processes of absorbing and releasing an external substance, the patch PA may provide a reaction space to the absorbed external substance for at least a predetermined amount of time. The patch PA may provide a specific environment for a least some time to the liquid substance SB captured in the patch PA, including the absorbed external substance.

The liquid substance SB that has been captured in the patch PA and the external substance captured in the patch PA may react inside the patch PA. The external substance absorbed into the patch PA may be affected by an environment provided by the patch PA. The substance released from the patch PA may include at least a portion of a substance generated through the reaction. The external substance may be released from the patch PA, after the composition, characteristics, and the like of the external substance are changed.

The absorbed substance may be released from the patch PA. The external substance being absorbed into the patch PA and being released from the patch PA may be understood at the external substance passing through the patch PA. The external substance that has passed through the patch PA may lose integrity due to a reaction inside the patch PA or an influence of an environment provided by the patch PA.

The above-described processes of absorption of an external substance, reaction of a substance, and providing of the substance may be carried out in one direction. In other words, the absorption of a substance may be performed at one position of the patch PA, the providing of an environment may be performed at another position of the patch PA, and the release of the substance may be performed at yet another position of the patch PA.

Figure 26:
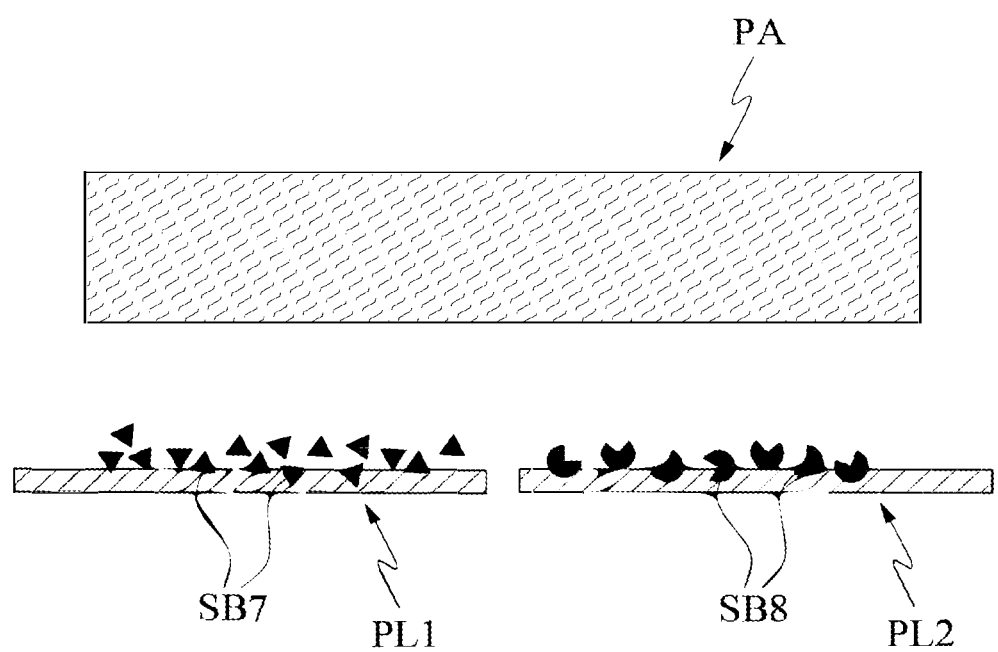
FIG. 26 illustrates performance of absorbing and providing of a substance as an embodiment of a patch according to the present application.
Figure 27:
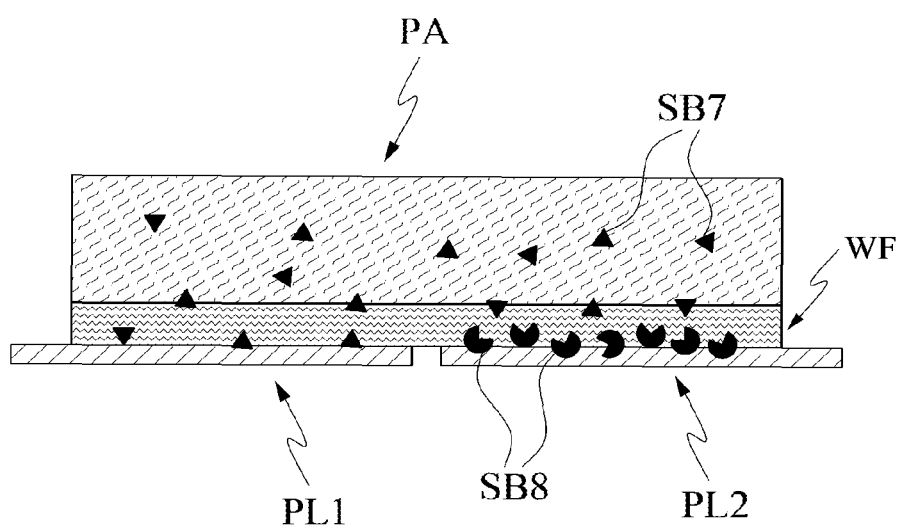
FIG. 27 illustrates performance of absorbing and providing of a substance of a an embodiment of a patch according to the present application.
Figure 28:
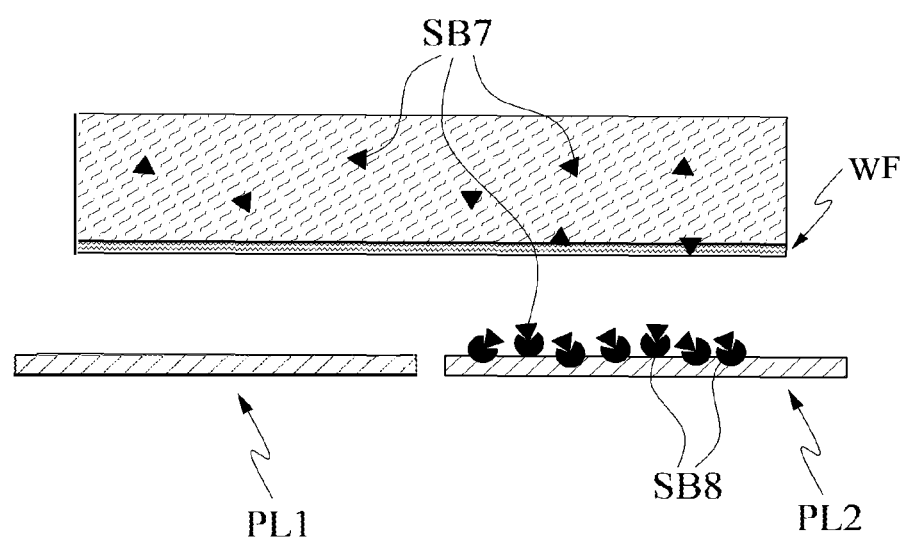
FIG. 28 illustrates performance of absorbing and providing of a substance as an embodiment of a patch according to the present application.

FIGS. 26 to 28 illustrate providing of a substance movement path between two plates PL as an embodiment of the patch PA according to the present application. According to FIGS. 26 to 28, the patch PA may provide a substance movement path between a plate PL1 on which a seventh substance SB7 is applied and a plate PL2 on which an eighth substance SB8 is applied. As a specific example, when the seventh substance SB7 is capable of binding to the eighth substance, and the eighth substance is fixed to air plate PL2, the patch PA may come into contact with the plates PL1 and PL2 so that the seventh substance SB7 is moved through the patch PA and bound to the eighth substance SB8. The seventh substance SB7 and the eighth substance SB8 may be connected to the patch PA through a water film WF formed by the patch PA coming into contact with the plates PL1 and PL2.

Figure 29:
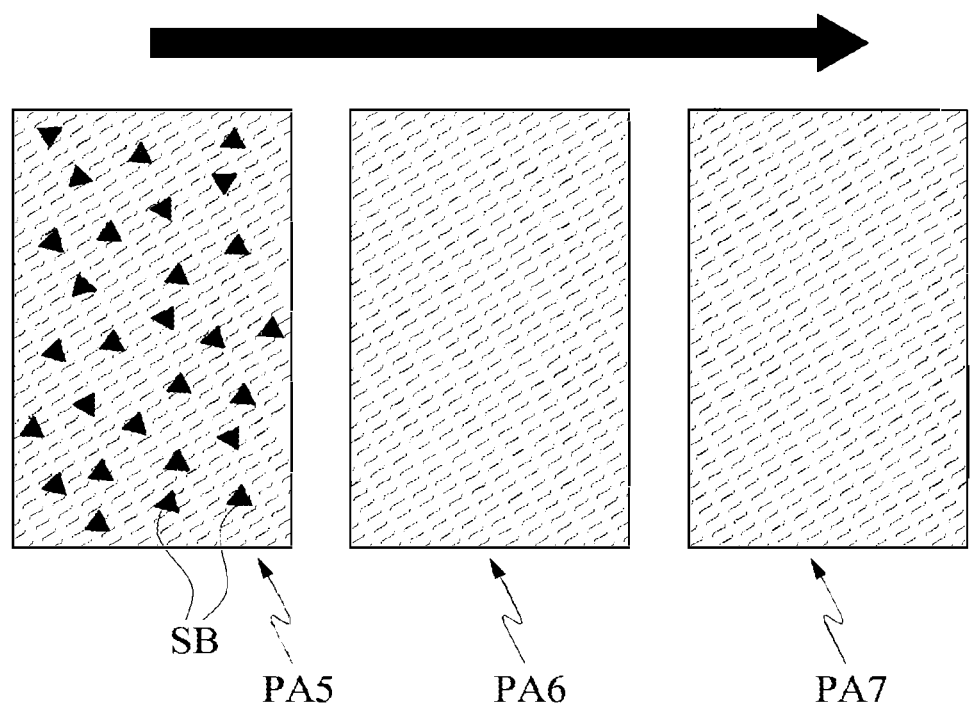
FIG. 29 illustrates performance of absorbing and providing of a substance as an embodiment of a patch according to the present application.
Figure 30:
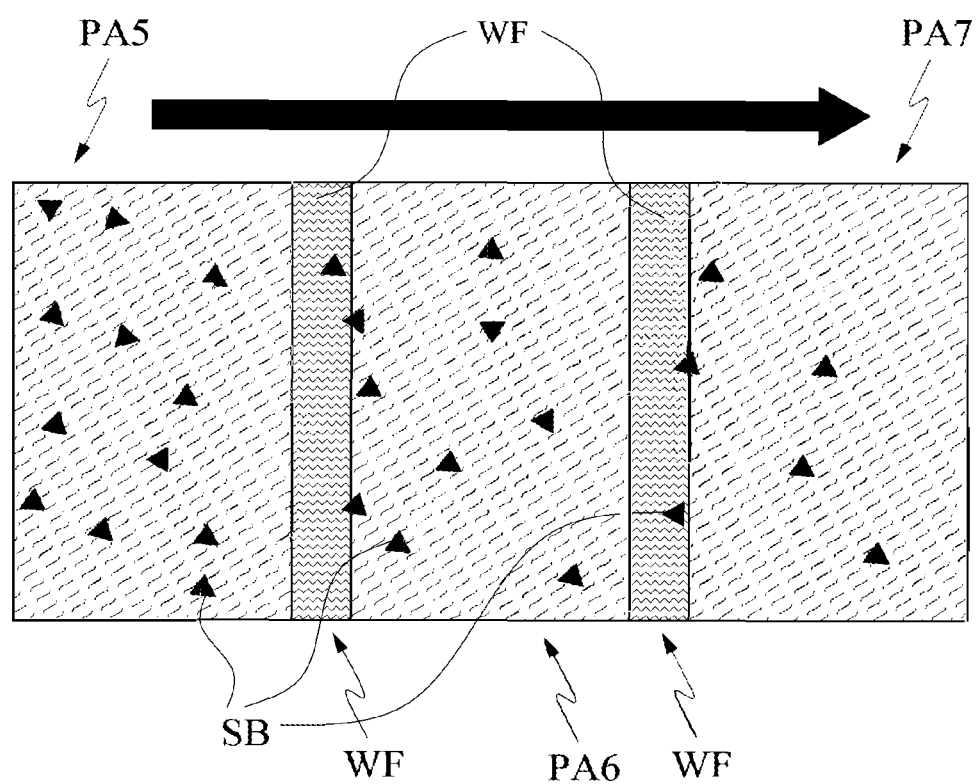
FIG. 30 illustrates performance of absorbing and providing of a substance as an embodiment of a patch according to the present application.

FIGS. 29 and 30 illustrate providing of a substance movement path between two patches as an embodiment of the patch PA according to the present application. Accreting to FIGS. 29 and 30, a patch PA6 configured to provide the movement path may be in contact with a patch PA5 configured to contain a substance to be moved, and a patch PA7 configured to a receive the substance to be moved. The patch PA6 configured to provide the movement path may come into contact with the patch PA5 configured to contain the substance to be moved and the patch PA7 configured to receive the substance to be moved, and the substance to be moved may be moved to the patch PA7 configured to receive the substance to be moved. The movement of the substance between the patches may be performed by a water film WF formed in the vicinity of a contact region between the patches.

Figure 31:
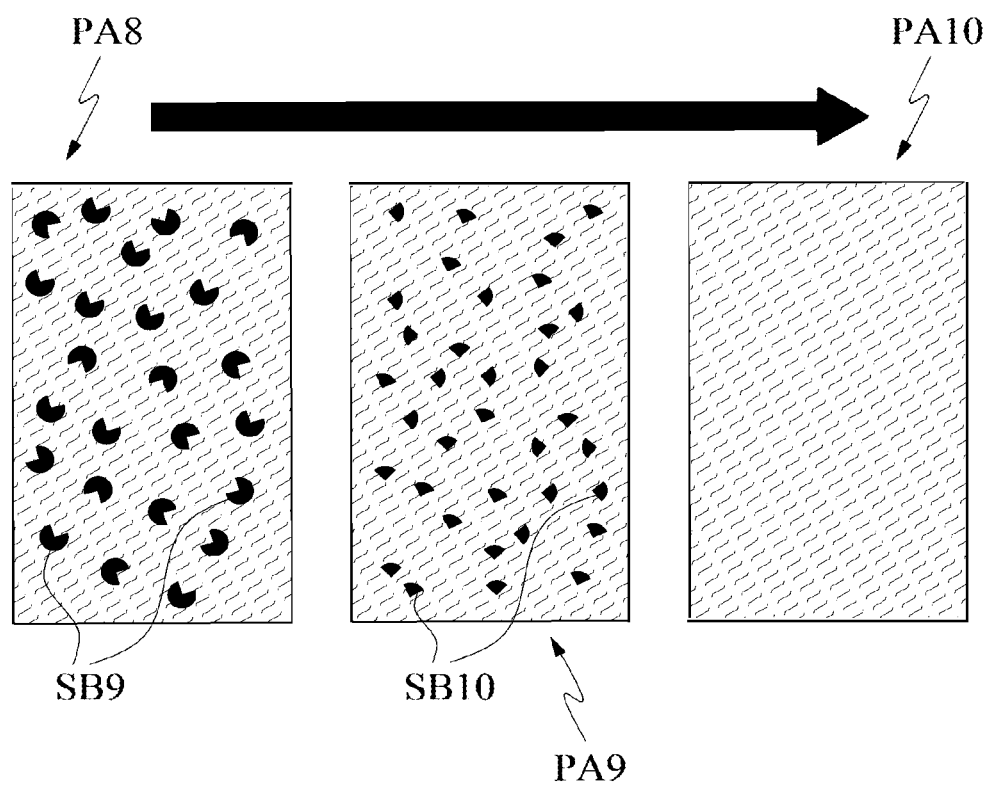
FIG. 31 illustrates performance of absorbing and providing of a substance and providing of an environment as an embodiment of a patch according to the present application.
Figure 32:
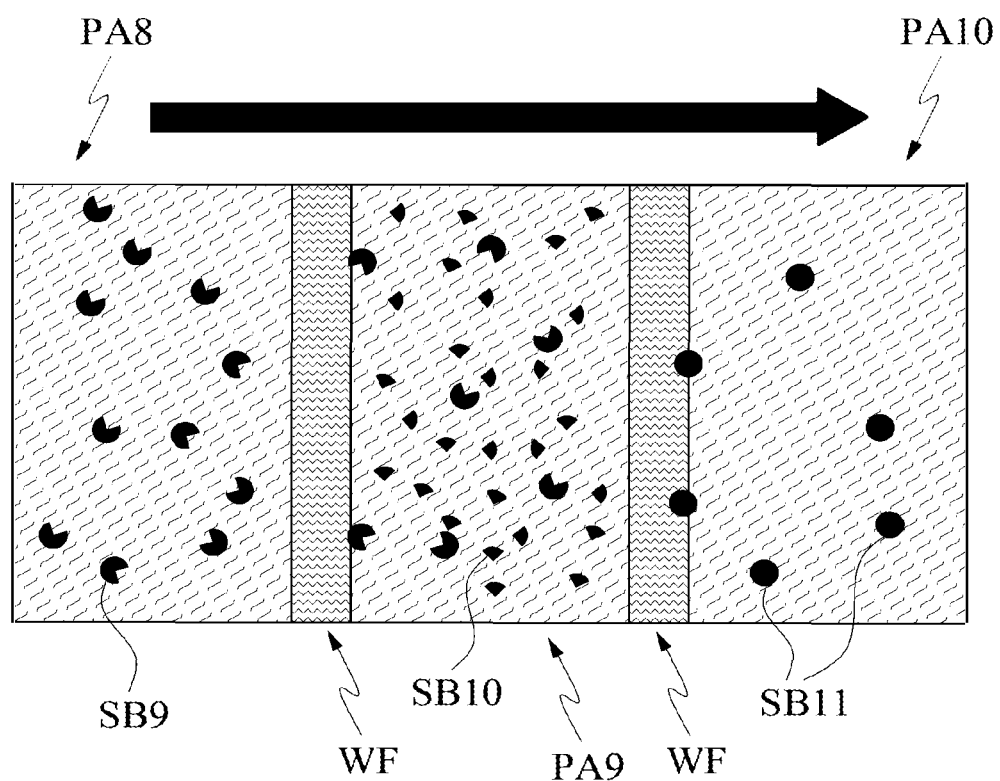
FIG. 32 illustrates performance of absorbing and providing of a substance and providing of an environment as an embodiment of a patch according to the present application.

FIGS. 31 and 32 illustrate providing of a substance movement path between two patches as an embodiment of the patch according to the present application. According to FIGS. 29 and 30, a patch PA9 configured to provide the movement path may be in contact with a patch PA8 configured to contain a ninth substance SB9 and a patch PA10 configured to receive a substance. The patch PA9 providing the movement path may come into contact with the patch PA8 configured to contain the ninth substance SB9 to absorb the ninth substance SB9. The absorbed ninth substance SB9 may react with a tenth substance SB10 contained in the patch PA9, which is configured to provide the movement path, and generate an eleventh substance. An eleventh substance SB11 may be provided from the patch PA9 confirmed to provide the movement path to the patch PA10 configured to receive the substance. The movement of a substance between the patches PA may be performed though a water film WF formed in the vicinity of a contact region between the patches PA.

3.3 Multi-Patch

A patch PA may be solely used, or a plurality of patches PA may be used together. In this cast, the plurality of patches PA being able to be used together includes a case in which the plurality of patches PA are sequentially used as well as a case in which the plurality of patches PA are used simultaneously.

When the plurality of patches PA are used simultaneously, the patches PA may perform different functions. Although each patch PA of the plurality of patches PA may contain the same substance, the plurality of patches PA may also contain different substances.

When the plurality of patches PA are used simultaneously, the patches PA may not come into contact with each other such that substance movement does not occur between the patches PA, or a desired function may be performed in a state in which substances contained in the patches PA are exchangeable.

Although the plurality of patches PA used together may be manufactured in shapes similar to each other or in the same size, the plurality of patches PA may be used together even when the plurality of patches PA have different shapes. Each patch PA constituting the plurality of patches PA may be manufactured such that densities of the mesh structural bodies NS are different or components constituting the math structural bodies NS are different.

3.3.1 Contact with Plurality of Patches

When a plurality of patches PA are used, the plurality of patches PA may come into contact with a single target region TA. The plurality of patches PA may come into contact with the single target region TA and perform a desired function.

When a plurality of target regions TA are present, the plurality of patches PA may come into contact with different target regions TA. When the plurality of target regions TA are present, the plurality of patches PA may respectively come into contact with corresponding target regions TA and perform a desired function.

The plurality of patches PA may come into contact with a substance applied on the target region TA. In this case, the substance applied on the target region TA may be fixed or have fluidity.

The desired function may be a function of providing or absorbing the substance. However, each patch PA does not necessarily provide the same substance or absorb the same substance, and the patches PA may provide different substances to the target region TA or absorb different components from a substance placed in the target region TA.

The desired function may be different for each patch PA constituting the plurality of patches PA. For example, one patch PA may perform the function of providing a substance to the target region TA, and another patch PA may perform the function of absorbing the substance from the target region TA.

The plurality of patches PA may include different substance, and the different substance may be provided to a single target region TA and used to induce a desired reaction. When a plurality of components of a substance is required for the desired reaction to occur, the plurality of components may be contained in a plurality of patches PA respectively and provided to the target region TA. Such use of the plurality of patches PA may be particularly useful when properties of substances required for a desired reaction are lost or altered when the substances required for the reaction being mixed for reason such as being contained in a single patch PA.

According to an embodiment, when the plurality of patches PA include substances formed of different components, and the substances formed of different components have different specific binding relationships, the substances formed of different components may be provided to the target region TA. The plurality of patches PA may be used to detect a plurality of specific bindings from the substances applied on the target region TA, by providing the substances including different components.

According to another embodiment, the plurality of patches PA may include substances formed of the same component, but each patch PA may have a different concentration with aspect to the substance formed of the same component. The plurality of patches PA including the substances formed of the same component may come into contact with the target region TA and be used to determine an influence in accordance with a concentration of the substance included in the plurality of patches PA.

When the plurality of patches PA are used as described above, the patches PA may be grouped into more efficient forms and used. In other words, the configuration of the plurality of patches PA being used may be changed every time the plurality of patches PA at used. The plurality of patches PA may be manufactured in the form of a cartridge and used. In this case, the form of each patch PA being used may be suitably standardized and manufactured.

The plurality of patches PA in the form of a cartridge may be suitable when patches PA configured to contain a plurality of types of substances are manufactured to be used by being chosen as necessary.

Particularly, when attempting to detect a specific reaction of each substance from the target region TA using a plurality of types of substances, a combination of specific reactions to be detected may be changed every time the detection is performed.

Figure 33:
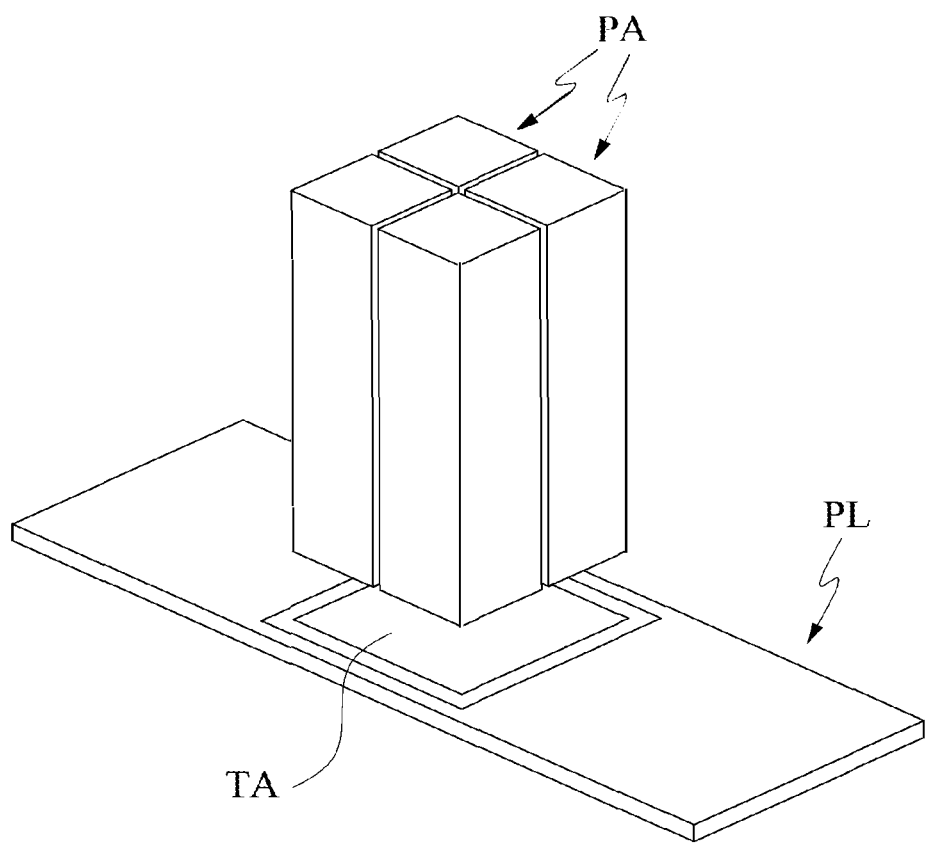
FIG. 33 illustrates an implementation of a plurality of patches as an embodiment of a patch according to the present application.

FIG. 33 illustrates a case in which the plurality of patches PA are used together as an embodiment of the patch PA according to the present application. According to FIG. 33, the plurality of patches PA according to an embodiment of the present application may simultaneously come into contact with a target region TA placed on a plate PL. The patches PA constituting the plurality of patches PA may have a standardized form. The plurality of patches PA may include a first patch and a second patch, and a substance contained in the first patch may be different from a substance contained in the second patch.

Figure 34:
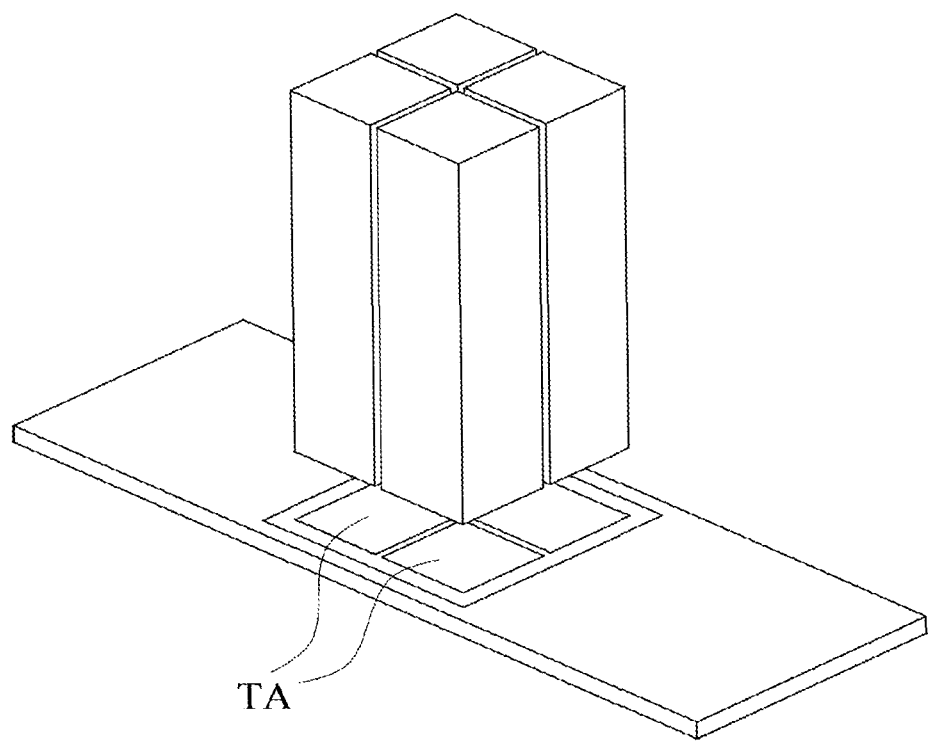
FIG. 34 illustrates an implementation of a plurality of patches and a plate having a plurality of target regions as an embodiment of a patch according to the present application.

FIG. 34 illustrates a case in which the plurality of patches PA are used and the plate PL includes a plurality of target regions TA. According to FIG. 34, the plurality of patches PA according to an embodiment of the present application may simultaneously come into contact with the plurality of target regions TA placed on the plate PL. The plurality of patches PA may include a first patch PA and a second patch PA, the plurality of target region TA may include a first region and a second target region, and the first patch may come into contact with the first target region and the second patch may come into contact with the second target region.

3.3.2 Fifth Embodiment

The plurality of patches PA may perform a plurality of functions. As described above, the patches PA may simultaneously perform a plurality of functions, and the patches PA may also simultaneously perform on different functions. However, embodiments are not limited to the above, and the functions may also be combined and performed in the plurality of patches PA.

First, in the case in which the patches PA simultaneously perform the plurality of functions, the patches PA may perform both containing and release of a substance. For example, the patches PA may contain different substances and release substances contained in the target regions TA. In this case, the contained substances may be simultaneously or sequentially released.

Next, in the case in which the patches PA simultaneously perform different functions, the patches PA may separately perform containing and release of a substance. In this case, only some of the patches PA may come into contact with a target region TA and release a substance to the target region TA.

3.3.3 Sixth Embodiment

When a plurality of patches PA are used, as described above, the plurality of patches PA may perform a plurality of functions. First, the patches PA may simultaneously perform containing, releasing, and absorbing of substances. Alternatively, the patches PA may also separately perform the containing, releasing, and absorbing of the substances. However, embodiments are not limited thereto, and the functions may also be combined and performed in the plurality of patches PA.

For example, at least some of the plurality of patches PA may contain a substance and release the contained substance to the target region TA. In this case, at least a remainder of the plurality of patches PA may absorb a substance from the target region TA. Some of the plurality of patches PA may release a substance that binds specifically to a substance placed in the target region TA. In this case, specific binding may be detected by absorption of a substance that has not formed specific binding from the substance placed in the target region TA using another patch PA.

3.3.4 Seventh Embodiment

When a plurality of patches PA are used, the patches PA may simultaneously perform containing and release of a substance and providing of an environment. Alternatively, the patches PA may separately perform the containing and release of a substance and providing of an environment. However, embodiments are not limited thereto, and the functions may also be performed in combination in the plurality of patches PA.

For example, a patch PA among the plurality of patches PA may release a substance contained therein to the target region TA. In this case, another patch PA may provide an environment to the target region TA. Here, the providing of an environment may be implemented in the form in which an environmental condition of a substance contained in the other patch PA is provided to the target region TA. More specifically, a reacting substance may be provided to the target region TA by the patch PA, and the other patch PA may come into contact with the target region. TA and provide a buffering environment.

As anther example, the plurality of patches PA may be in contact with each other. In this case, at least one patch PA may contain a substance and release the substance contained therein to another patch PA configured to provide an environment. In the present embodiment, the patch PA configured to provide an environment may release a substance, come into contact with at least one other patch PA that is not in contact with the patch PA configured to provide an environment, and absorb a substance from the patch PA.

4. Tissue Diagnosis

The above-described patch according to the present application may also be applied in performing diagnosis of a tissue. Hereinafter, tissue diagnosis to which the patch of the present application is applied will be described.

4.1 Introduction 4.1.1 Meaning

In the present application, tissue diagnosis may be defined as a concept in which diagnosis, prediction, or management of an illness or a disease is performed with a tissue as a sample to be diagnosed that is a differentiated from performing diagnosis with a bodily fluid or cells as a sample.

In the narrow sense, "tissue" may refer to a tissue collected from the human body. For example, "tissue" may refer to a partial tissue, an epithelial tissue, or the like. In the broad sense, "tissue" may refer to tissues collected from animals and plants as well as the human body and may further include artificial tissues. Hereinafter, it will be assumed the "tissue" refers to the tissue in the narrow sense.

In applying the patch of the present application to immunoassay, the above-described base substance and additive substance may be properly changed in accordance with a site to which the patch is applied.

4.1.2 Classification of Tissue Diagnosis

In the present application, tissue diagnosis may be classified in accordance with a few standards.

Tissue diagnosis may be classified in accordance with methods of manufacturing a sample or states of the sample. A sample used in tissue diagnosis may be a microtome cut tissue filled with paraffin or a frozen section of tissue.

Tissue diagnosis may be classified in accordance with a target which is a standard of diagnosis (that is, a target substance). In other words, tissue diagnosis may be differently performed in accordance with a case in which it is desired to detect a target base sequence (or, a target nucleic acid sequence) and perform diagnosis, a case in which it is desired to detect a target protein (in particular, an antigen) and perform diagnosis, and a case in which it is desired to observe the morphology of cells that constitute a tissue. The target substance may include a target protein, a target base sequence, a DNA, and the like included in a tissue sample.

Tissue diagnosis may be classified in accordance with a method of obtaining a diagnosis result. The tissue diagnosis may be performed including a method of acquiring an image or a method of obtaining a quantitative measurement value of a target substance included in a same. The acquiring an image may refer to acquiring an image acquired in a bright field or a method of acquiring a fluorescene image.

4.1.3 Method of Tissue Diagnosis 4.1.3.1 Immunological Diagnosis

Tissue diagnosis according to the present application may refer to performing diagnosis by obtaining a distribution of target proteins in a tissue sample SA. In this case, an immunological method may be used. In other words, target proteins may be detected by an antigen-antibody reaction, and a distribution of the target proteins may be obtained.

The obtaining of the distribution of the target proteins may be performed using antibodies that bind specifically to the target proteins. In other words, the obtaining of the distribution of the target proteins may be performed by detecting a product PD due to a chemical reaction of a substance catalyzed by enzymes attached to the antibodies that bind specifically to the target proteins. The obtaining of the distribution of the target proteins may be performed using first antibodies that bind specifically to the target proteins and second antibodies that bind specifically to the first antibodies. In this case, labels that facilitate checking of the distribution of the target proteins may have been attached to the second antibodies.

Alternatively, the obtaining of the distribution of the target proteins may be performed by detecting fluorescence emitted from fluorophores attached to the antibodies that bind specifically to the target proteins.

As an example of the above-described immunological tissue diagnosis, whether cancer has developed may be checked by detecting a specific protein, expression of which is increased or decreased due to the development of cancer.

4.1.3.2 Morphological Diagnosis

Tissue diagnosis according to the present application may be performed by observing the morphology or distribution of cells and other substance that constitute a tissue sample SA. In this case, a staining process that makes parts constituting a tissue to exhibit color to facilitate performance of the morphological diagnosis may be accompanied.

As an example of the morphological tissue diagnosis, the morphology of cells that constitute a tissue sample SA may be observed and the characteristic morphology of malignant cells may be detected to determine a presence or type of tumor.

4.1.3.3 DNA Diagnosis

Tissue diagnosis according to the present application may be performed in accordance with a constitution of DNA included in a tissue sample SA. The tissue diagnosis may be performed by detecting a specific base sequence from a tissue sample SA.

As an example of the DNA tissue diagnosis, a tumorigenic gene (an oncogene) may be detected to predict the likelihood of developing cancer. Also, the DNA tissue diagnosis may be used in early detection of a genetic disease with likelihood of development, prenatal testing, and the like.

4.2 Preparation for Tissue Diagnosis

Tissue diagnosis according to the present application may be performed using the above-described patch PA with a tissue sample SA as a target.

4.2.1 Preparation of Sample to be Diagnosed

In tissue diagnosis according to the present application, diagnosis of a lesion may be performed for a tissue collected from a human body. The tissue collected from the human body may have been pre-processed to facilitate performance of diagnosis.

The tissue sample SA may be a microtome cut tissue sample SA that has been filled with paraffin or a frozen section of tissue. Gelatin may have been embedded in the tissue sample SA which is a frozen section of tissue. However, this is merely an example, and a medium other than parrafin, suds as celloidin and carbowax, may also have been embedded in the tissue sample SA.

The tissue sample SA may be collected from the human body and provided after gong though fixation, washing, dehydration, cleaning, infiltration, embedding, and microtome cutting. The provided tissue sample SA may be dried.

The tissue sample SA may be fixated by formaldehyde, ethyl alcohol, acetone, and the like.

The tissue sample SA may be formed as a thin section of tissue of 3 to 5 μm. The microtome-cut sample SA may be manufactured using a microtome such as a rotary microtome and a freezing microtome.

The tissue sample SA according to the present application may be placed on a plate PL. The tissue sample SA may be fixated on the plate PL.

The plate PL may refer to a general slide glass or a solid plate PL such as a plate PL manufactured with polystyrene, polypropylene or the like. A form of a bottom or transparency of the plate PL may be different in accordance with a detection means. The plate PL may include a reaction region which comes into contact with the patch PA or in which a desired reaction may occur.

The above-described plate, reaction region that may be placed on the plate, and tissue sample that may be placed in the reaction region may be interchangeably used in accordance with the context. Particularly, it is defined that, as a subject that comes into contact with the patch, the plate, the reaction region, and the tissue sample may be substituted with each other.

The tissue sample SA may be a living body. However, in the present application, unless particularly mentioned otherwise, it is assumed that diagnosis is performed on a tissue sample SA provided for histological analysis.

A method of performing diagnosis using a tissue simple SA placed on a plate PL will be described below.

4.1.1 Preparation of Patch

Tissue deposit according to the present application may be performed using the above-described patch PA.

The patch PA may contain a staining reagent for staining the tissue sample SA. The patch PA may contain the staining reagent and provide the staining reagent to the tissue sample SA. The staining reagent may include hematoxylin for staining a nucleus of the tissue or eosin for staining a cytoplasm. The staining reagent may be an immunostaining reagent for labeling a specific protein by an antigen-antibody reaction. The immunostaining reagent may include an antibody to which a specific protein binds specifically.

The patch PA may contain a fluorescence reagent for observing the tissue sample SA. The patch PA may contain the fluorescence and provide the fluorescence reagent to the tissue sample SA. The fluorescence reagent may contain some substance that label a target substance, label a target protein, or label a target DBA. The patch PA may contain a labeling substance such as a color labeling substance (e.g., hematoxylin) and a fluorescence labeling substance (e.g., an antibody with a fluorophore attached thereto).

The patches PA may be used separately or in combination in accordance with methods of performing tissue diagnosis.

4.2 Performance of Tissue Diagnosis

Tissue diagnosis according to the present application may be differently performed in accordance with detection patterns of diagnosis results.

When it is desired to acquire a bright-field image, diagnosis may be performed by staining (that is, color-labeling) of stale components of the tissue sample SA. When it is desired to acquire a fluorescence image, diagnosis may be performed by fluorescence-labeling of some components of the tissue sample SA.

The diagnosis performed by staining of some components of the tissue sample SA and the diagnosis performed by fluorescence-labeling of components of the tissue samples SA will be dared below with reference to FIGS. 35 to 38.

Figure 35:
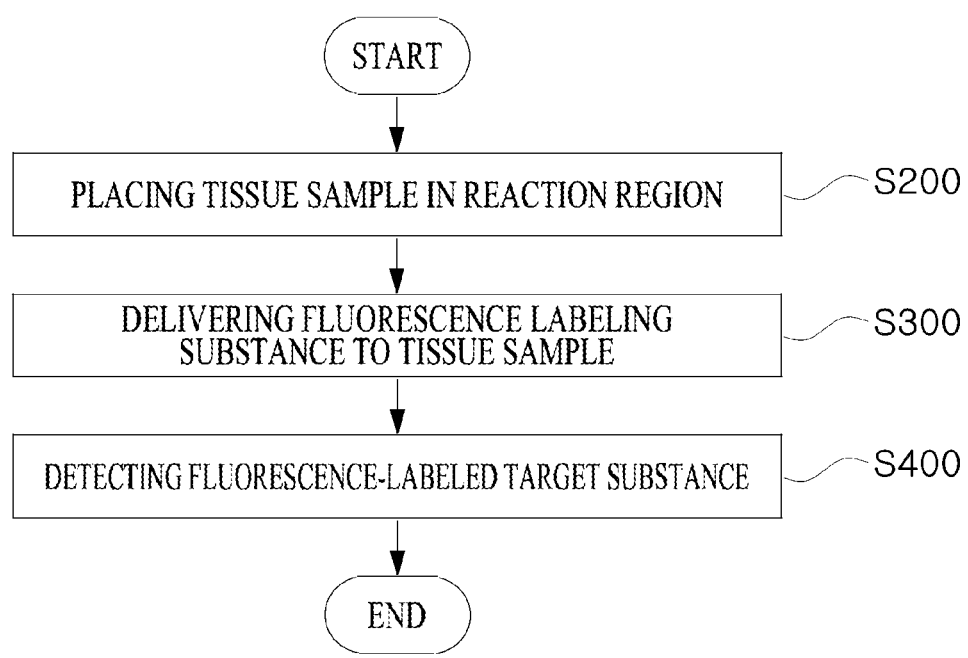
FIG. 35 illustrates a flowchart for describing an example of a tissue diagnosis method according to the present application.

Referring to FIG. 35, a tissue diagnosis method according to an embodiment of the present application may include placing a tissue sample SA in a reaction region (S200), providing fluorescence labeling substance to the tissue sample SA (S300), and detecting a fluorescence-labeled target substance TS (S400). The tissue diagnosis method may include detecting the target substance TS from the tissue sample SA by using a patch PA, which includes a mesh structural body forming micro-cavities and is configured to contain a substance in the micro-cavities.

In this case, the target substance TS may be a target base sequence included in the tissue sample SA, the fluorescence labeling substance may include a fluorescence-labeled nucleic acid probe, and the nucleic acid probe may bind complimentarily to the target base sequence. Alternatively, the target substance TS may be a fluorescence-labeled target protein, the fluorescence labeling substance may include a fluorescence-labeled antibody, and the antibody may bind specifically to the target protein.

The fluorescence labeling substance may be a fluorescence labeling complex that includes a reaction derivative that reacts specifically with the target substance TS and a fluorescence marker for detecting the target substance TS.

In this case, the reaction derivative may refer to a part that binds specifically to the target substance. For example, the reaction derivative may include a probe that binds complementarily to a target base sequence, an antibody that binds specifically to a target protein, or the like.

Also, the fluorescence marker may refer to a portion attached to the reaction derivative to induce a fluorescence detection. For example, the fluorescence marker may include a fluorophore attached to an antibody, and an enzyme that induces fluorescence emission by a chemical reaction with a fluorophore, which is attached to a probe, or a substrate.

The fluorescence-labeled probe may be a probe to which a fluorophore capable of emitting fluorescence is attached. The fluorescence-labeled probe may be a probe to which an enzyme that reacts with a substrate and induces fluorescence emission is attached.

The placing of the tissue sample SA in the reaction region (S200) may include fixating the tissue sample SA on the reaction region or the plate PL. The tissue sample SA may be a tissue sample SA which is cut with a microtome after going through at least some of fixation, washing, dehydration, cleaning, infiltration, and embedding.

The providing of the fluorescence labeling substance to the tissue sample SA (S300) may include providing the fluorescence labeling substance to the tissue sample SA by using the patch PA that contains the fluorescence labeling substance for specifically labeling the target substance TS.

The detecting of the fluorescence-labeled target substance TS (S400) may include detecting the fluorescence-labeled target substance TS from the tissue maple SA.

The detecting of the fluorescence label may be performed by acquiring a fluorescence image of the tissue sample SA. The fluorescence image may refer to an image in which the fluorescence labeled to the target substance is identifiably displayed.

The detecting of the fluorescence-labeled target substance TS may be performed by measuring an amount of fluorescence emitted from the target substance TS included in the tissue uncle SA. The detecting of the fluorescence-labeled target substance TS may include obtaining information on distribution of the target substance TS in the tissue sample SA.

The obtaining of the distribution of the target substance in the tissue sample may include obtaining positions at which the target substance is distributed, regions at which the target substance is distributed, forms of the distribution, or an amount of the distributed target substance.

Figure 36:
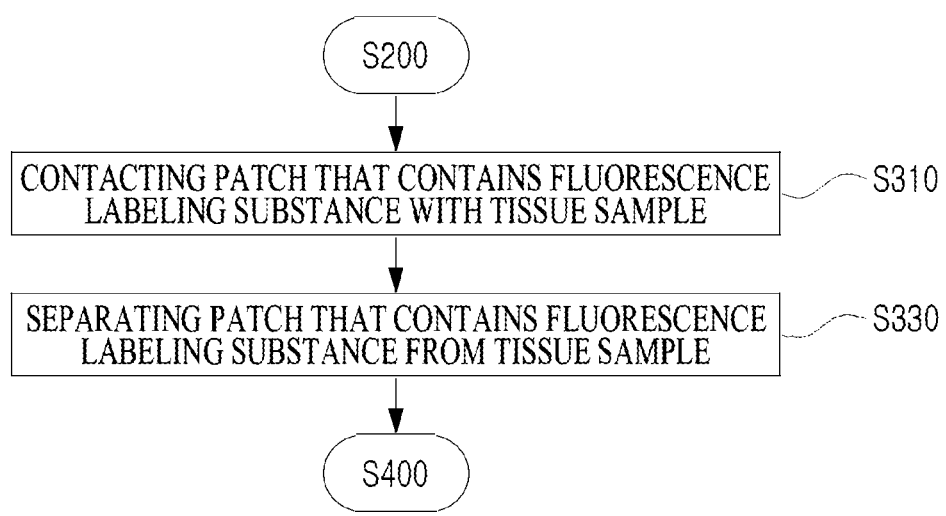
FIG. 36 illustrates a flowchart for describing an example of delivering a fluorescence labeling substance to a tissue sample in a tissue diagnosis method according to an embodiment of the present application.

Referring to FIG. 36, in the tissue diagnosis method according to the present application, the providing of the fluorescence labeling substance to the tissue sample SA (S300) may include contacting the patch PA which contains the fluorescence labeling substance with the tissue sample SA (S310) and separating the patch PA which contains the fluorescence labeling substance from the tissue sample SA (S330).

In the contacting of the patch PA which contains the fluorescence labeling substance with the tissue sample SA (S310), when the patch PA is in contact with the tissue sample SA, the fluorescence labeling substance may be allowed to move to the reaction region.

In the separating of the patch PA which contains the fluorescence labeling substance from the tissue sample SA (S330), when the patch PA is separated from the tissue sample SA, a residual fluorescence labeling substance that has not bound in the target substance TS of the fluorescence labeling substance may be removed from the reaction region.

Figure 37:
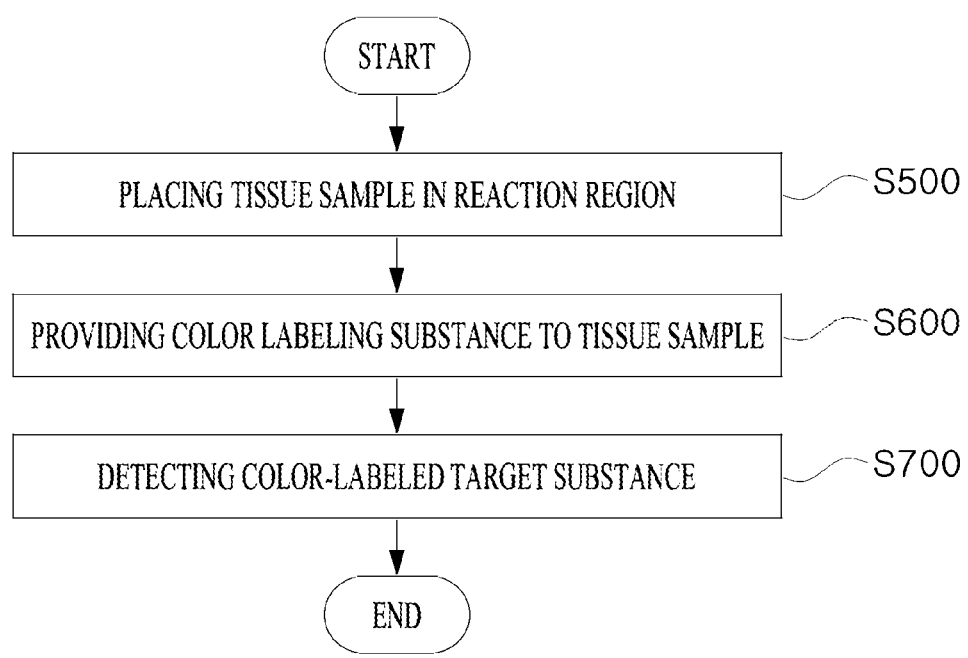
FIG. 37 illustrates a flowchart for describing an example of a tissue diagnosis method according to the present application.

Referring to FIG. 37, the tissue diagnosis method according to an embodiment of the present disclosure may include placing a tissue sample SA in a reaction region (S500), providing a color labeling substance to the tissue sample (S600), and detecting a color-labeled substance TS (S700). The tissue diagnosis method may include detecting the target substance TS from the tissue sample SA by using a patch PA, which includes a mesh structural body forming micro-cavities and is configured to contain a substance in the micro-cavities.

The color labeling substance may be a color labeling complex that includes a reaction derivative that reacts specifically with the target substance TS and a color marker for detecting the target substance TS.

In this case, the reaction derivative may refer to a part that binds specifically to the target substance. For example, the reaction derivative may include a probe that binds complementarily to a target bate sequence, an antibody that binds specifically to a target protein, or the like.

Also, the color marker may refer to a portion attached to the reaction derivative to induce a color detection. For example, the color marker may include an enzyme which is attached to an antibody and induces fluorescence emission by a chemical reaction with a substrate or the enzyme attached to a probe.

The target substance TS may be a target base sequence included in the tissue sample SA, and the color labeling substance may include a nucleic acid probe that binds complementarily to the target base sequence. Alternatively, the target substance TS may be a target protein included in the tissue sample SA, the color labeling substances may include an antibody to which a marker which induces color labeling is attached, and the antibody may bind specifically to the target protein. The target protein included in the tissue sample may be an antigen.

The placing of the tissue sample SA in the reaction region (S500) may be performed similarly as in the above-described embodiment.

The providing of the color labeling substance to the tissue sample SA (S600) may include providing a staining substance to the tissue sample SA by using a patch PA which contains the color labeling substance for assigning color to the target substance TS. The assigning of the color may refer to binding particles which exhibit color to the target substance, infiltrating a substance which exhibits color to the target substance, or the like.

The detecting of the color-assigned target substance TS (S700) may be performed by acquiring an image of the tissue sample SA. In this case, the image of the tissue sample SA may be an image in which the color labeling is displayed.

Figure 38:
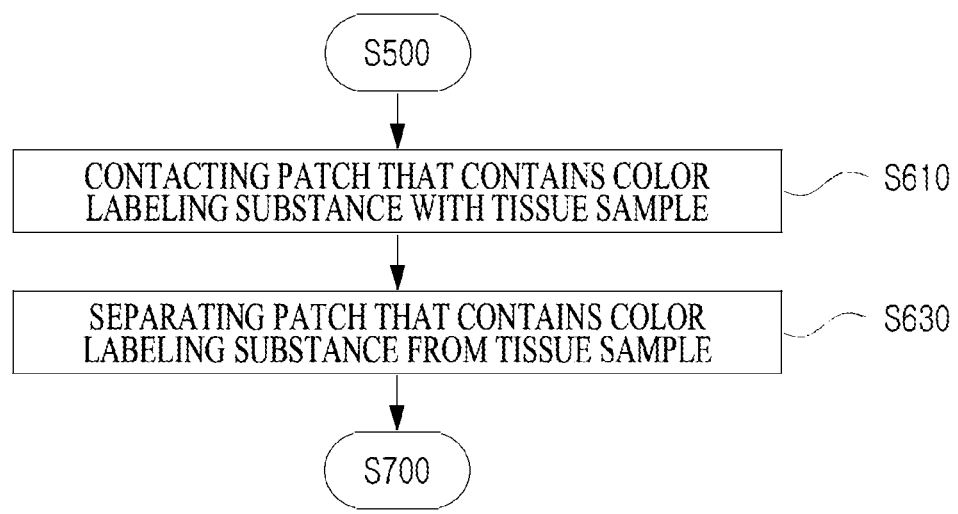
FIG. 38 illustrates a flowchart for describing an example of delivering a color labeling substance to a tissue sample in a tissue diagnosis method according to an embodiment of the present application.

Referring to FIG. 38, in the tissue diagnosis method according to the present embodiment, the providing of the color labeling substances to the tissue sample SA (S600) may include contacting the patch PA which contains the color labeling substances with the tissue simple SA (S610) and separating the color labeling substances from the tissue sample SA (S630).

In the contacting of the patch PA which contains the color labeling substances with the tissue sample SA (S610), when the patch PA is in contact with the tissue sample SA, the color labeling substances may be movable to the reaction region.

In the separating of the color labeling substances from the tissue sample SA (S630), when the patch PA is separated from the tissue sample SA, a residual color labeling substance that has not reacted with the target substance TS of the color labeling substances may be removed from the reaction region.

Figure 48:
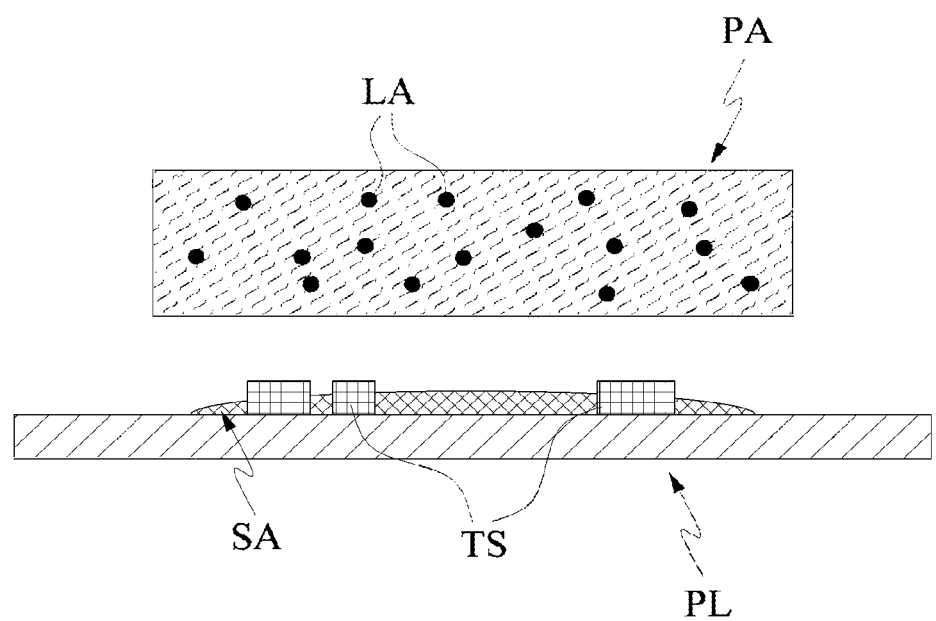
FIG. 48 illustrates an embodiment of a tissue diagnosis method according to the present application.
Figure 49:
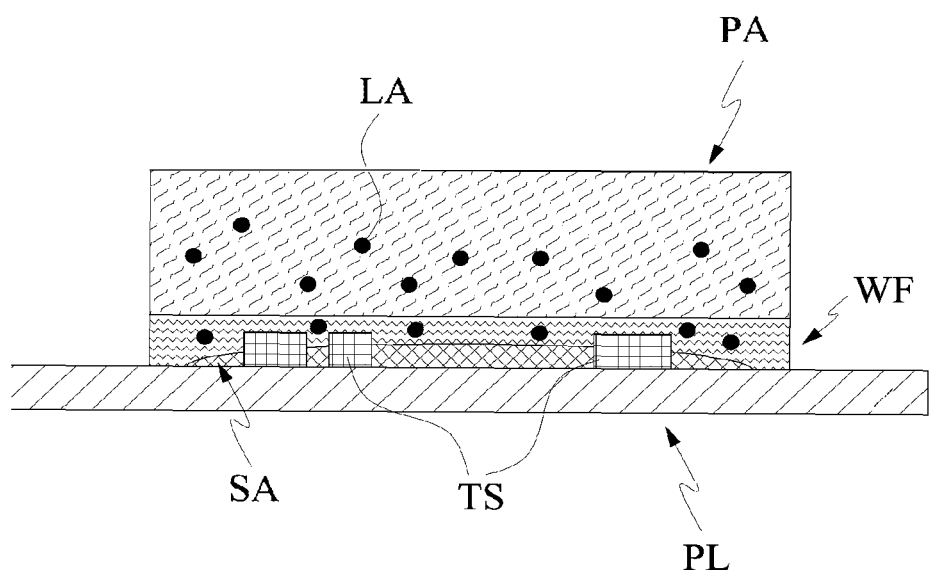
FIG. 49 illustrates an embodiment of a tissue diagnosis method according to the present application.
Figure 50:
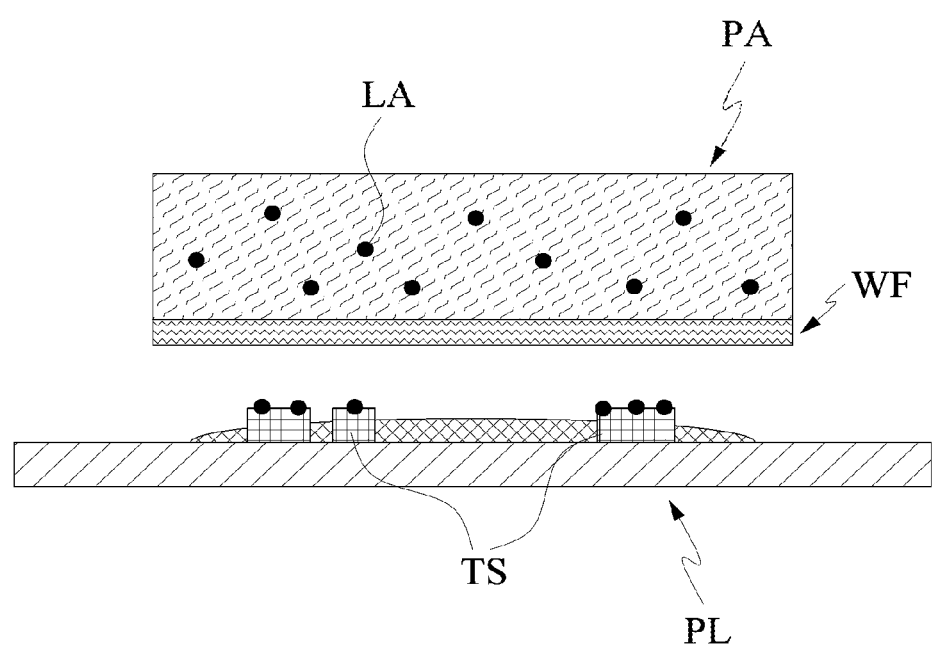
FIG. 50 illustrates au embodiment of a tissue diagnosis method according to the present application.

FIGS. 48 to 50 schematically illustrate the detecting of the target substance included in the tissue sample SA by using the patch PA, as an embodiment of the tissue diagnosis method according to the present application. According to FIGS. 48 to 50, the tissue sample SA may be placed on the plate PL, labeling substances LA may be provided to the tissue sample SA, and the target substance TS labeled by the labeling substances LA may be detected. The labeling substances LA in the present embodiment may be a fluorescence labeling substance or color labeling substance.

In this case, the providing of the labeling substances LA may be performed using a patch PA that contains the labeling substances LA.

The providing of the labeling substance LA may be performed by contacting the patch PA which contains the labeling substances LA with the tissue sample SA (or the reaction region) and then separating the patch PA therefrom (S310, S330, S610, S630). By contacting the patch PA which contains the labeling substances LA with the tissue sample SA (S310, S610), a water film WF may be formed in the vicinity of a contact portion. The labeling substances LA may be allowed to move to the reaction region (or the tissue sample SA) through the formed wars film WF. The labeling substances LA which have been allowed to move to the reaction region may react specifically with or bind specifically to the target substance TS included in the tissue sample SA or be attached to the target substance TS.

By separating the patch PA from the plate PL or the tissue sample SA (S330, S630), a labeling substance LA that has not reacted with the target substance TS (that is, the residual labeling substance) may be removed from the plate PL. When the patch PA is separated from the plate PL, the water film WF which has been formed may move along with the patch PA, and the residual labeling substance may be captured in the water film WF and absorbed heat the patch PA. The residual labeling substance may be removed from the plate PL when the patch PA is separated from the plate PL. The residual labeling substance may include a residual color labeling substance or a residual fluorescence labeling unbalance.

The target substance TS included in the tissue sample SA may be detected by detecting the labeling substances LA which have reacted specifically with or bound specifically to the target substance TS and are placed on the plate PL.

Figure 51:
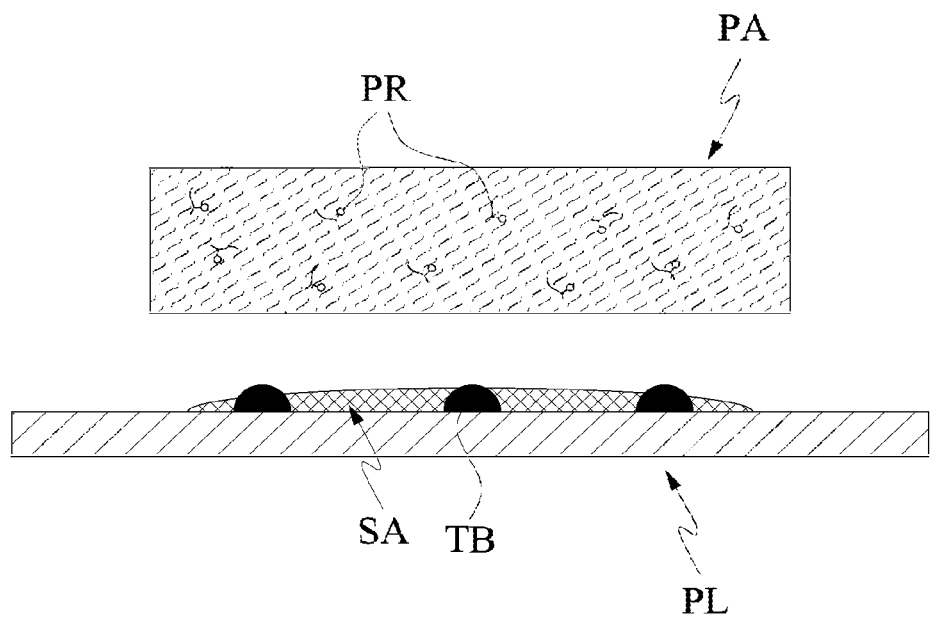
FIG. 51 illustrates a case in which a probe is used, as an embodiment of a tissue diagnosis method according to the present application.
Figure 52:
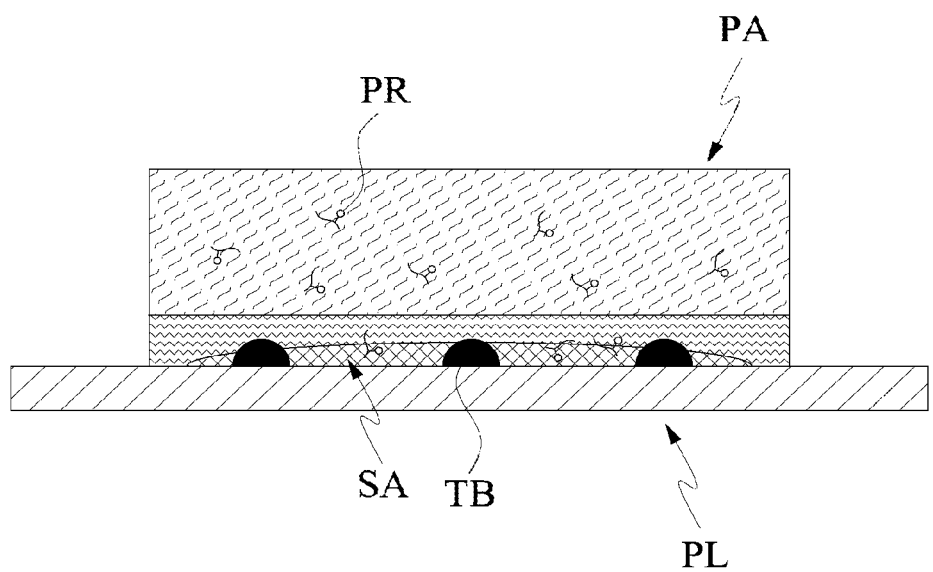
FIG. 52 illustrates a case in which a probe is used, as an embodiment of a tissue diagnosis method according to the present application.
Figure 53:
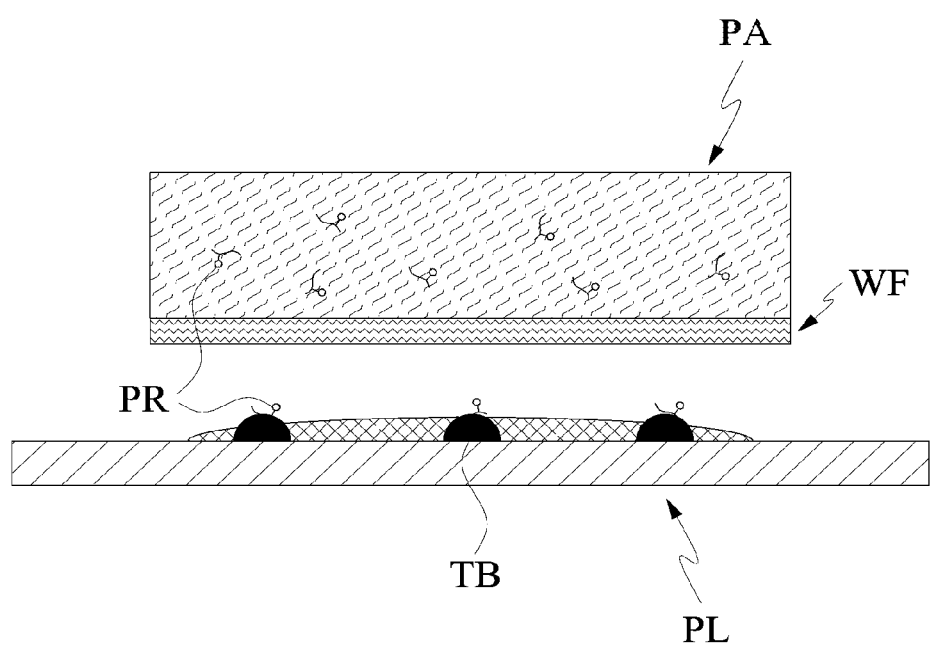
FIG. 53 illustrates a case in which a probe is used, as an embodiment of a tissue diagnosis method according to the present application.
Figure 54:
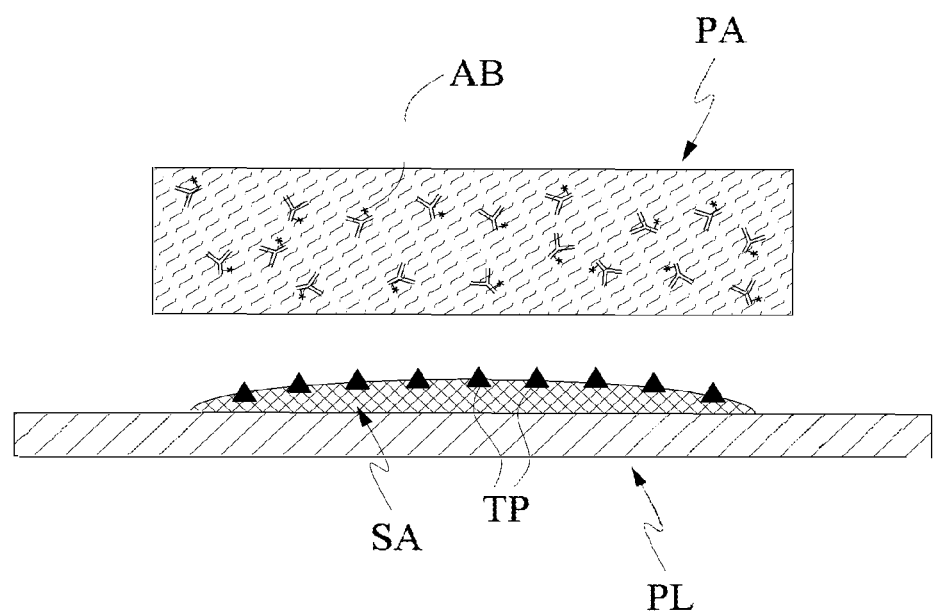
FIG. 54 illustrates a case in which an antibody is used, as an embodiment a a tissue diagnosis method according to the present application.
Figure 55:
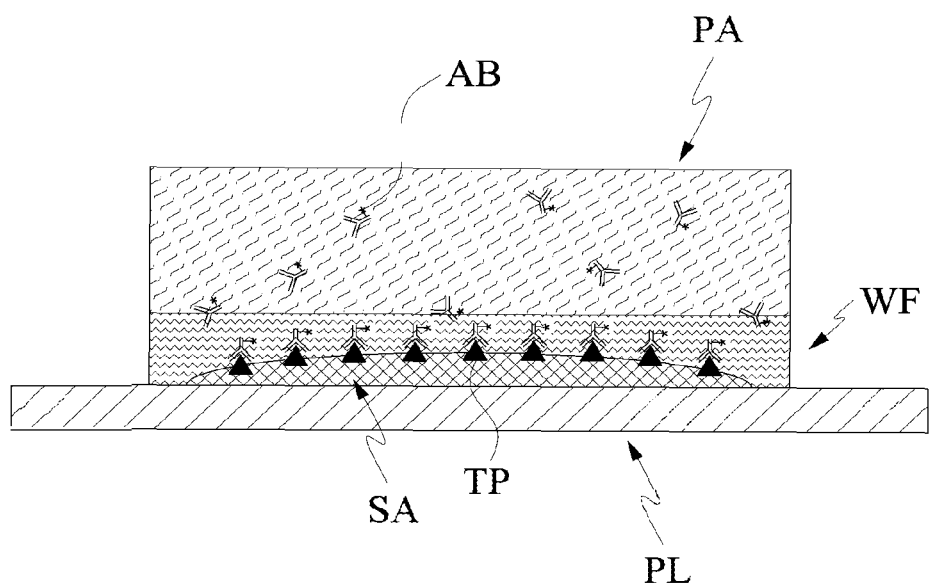
FIG. 55 illustrates a case in which an antibody is used, as an embodiment of a tissue diagnosis method according to the present application.
Figure 56:
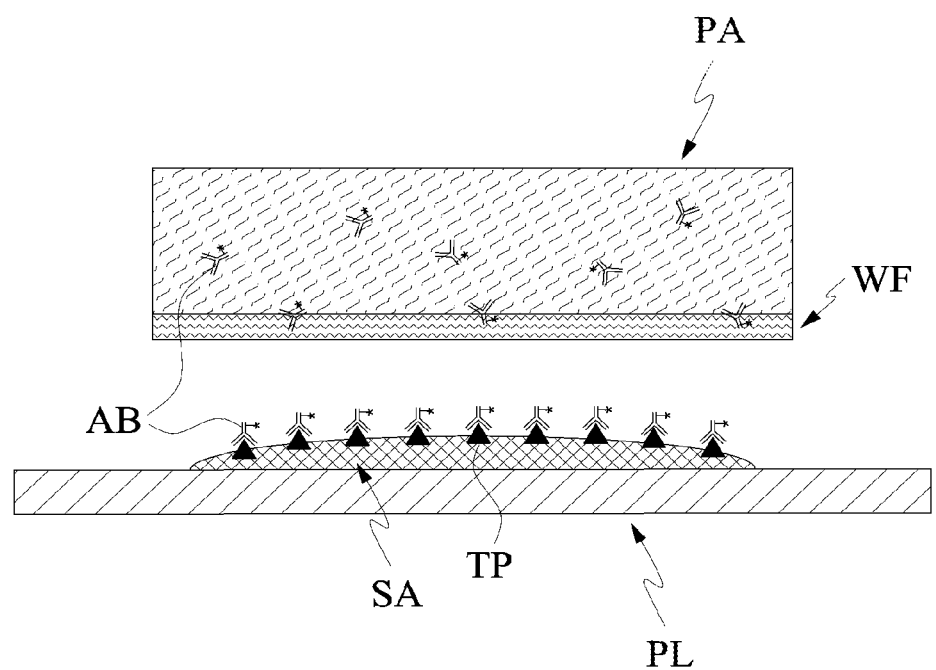
FIG. 56 illustrates a case in which an antibody is used, as an embodiment of a tissue diagnosis method according to the present application.
Figure 57:
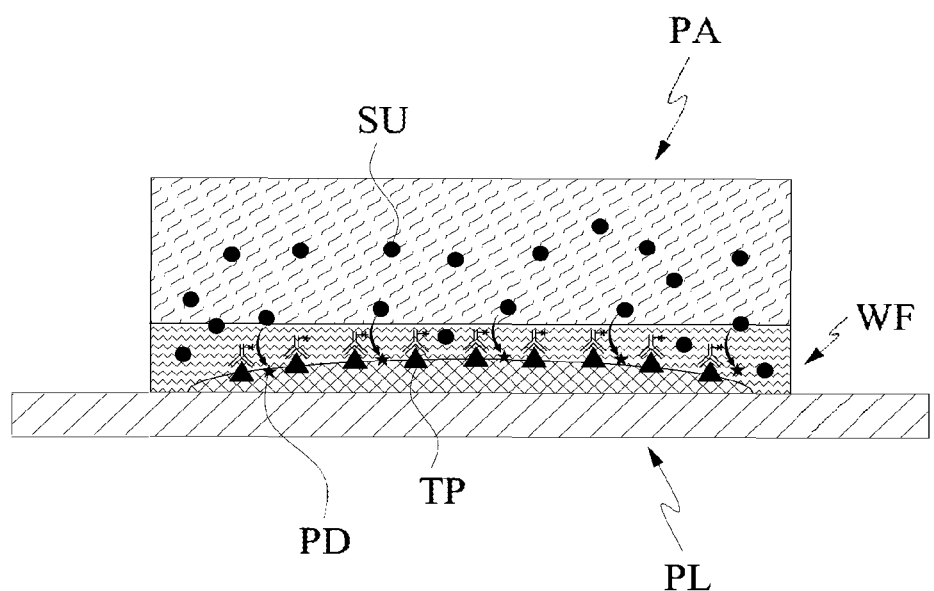
FIG. 57 illustrates a case in which an antibody is used, as an embodiment of a tissue diagnosis method according to the present application.
Figure 58:
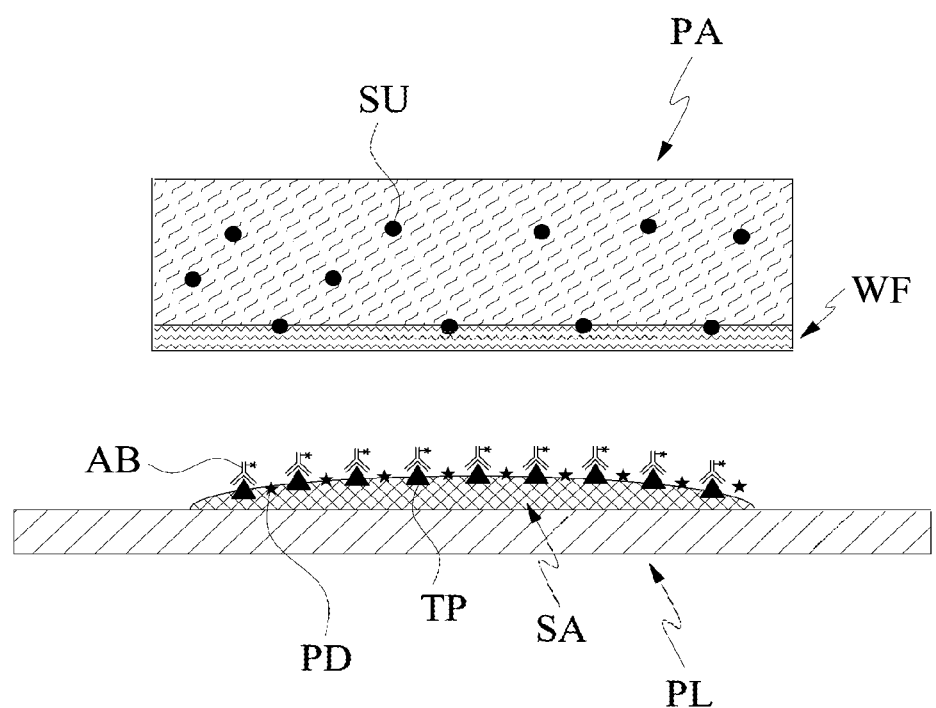
FIG. 58 illustrates a case in which an antibody is used, as an embodiment of a tissue diagonals method according to the present application.

FIGS. 51 to 53 illustrate a case in which a probe PR is used to detect a target base sequence TB included in a tissue sample SA, as an embodiment of the tissue diagnosis method according to the present application. Referring to FIGS. 51 to 53, a tissue sample SA may be placed on the plate PL, a labeling probe PR having a complementary relationship with the target base sequence TB may be provided to the tissue sample SA, and the target base sequence TB labeled by the labeling probe PR may be detected. In this case, the providing of the labeling probe PR may be performed using a patch PA that contains the labeling probe PR.

The providing of the labeling probe PR may be performed by contacting the patch PA which contains the labeling probe PR with the tissue sample SA and separating the patch PA therefrom (S310, S330, S610, S630). By contacting the patch PA which contains the labeling probe PR with the tissue sample SA (S310, S610), a water film WF may be formed in the vicinity of a contact portion. The labeling probe PR may became movable to the reaction region through the formed water film WF. The labeling probe PR which his become movable to the reaction region may bind complementarily to the target base sequence TB included in the tissue sample SA.

By separating the patch PA front the plate PL or the tissue sample SA (S330, S630), a labeling probe PR which has not bound to the target base sequence TB (that is, residual labeling probe) may be removed from the plate PL. When the patch PA is separated from the plate PL, the water film WF, which has been formed, may move along with the patch PA, and the residual labeling probe may be captured in the water film WF and absorbed into the patch PA. The residual labeling probe may be removed from the plate PL when the patch PA is separated from the plate PL.

FIGS. 51 to 53 merely schematically illustrate the detection of the target base sequence by using a labeling probe, and the labeling probe may substantially infiltrate into cells of the tissue sample SA and bind specifically to the target base sequence TB.

FIGS. 54 to 58 schematically illustrate a case in which an antibody AB is used to detect a target protein included in a tissue sample SA, as an embodiment of the tissue diagnosis method according to the present application. Referring to FIGS. 54 to 58, a tissue sample SA may be placed on the plate PL, an antibody AB may be provided to the tissue sample SA, and a target protein may be detected from the tissue sample SA.

In this case, the providing of the antibody AB may be performed using a patch PA that contains the antibody AB. Also, a label for identification may be attached to the antibody AB.

The providing of the antibody AB may be performed by contacting the patch PA which contains the antibody AB with the tissue sample SA and separating the patch PA therefrom. By contacting the patch PA which contains the antibody AB with the tissue sample SA, a water film WF may be formed in the vicinity of a contact portion. The antibody AB may become movable to the reaction region through the formed water film WF. The antibody AB which has become movable to the reaction region may bind specifically to the target protein included in the tissue sample SA.

By separating the patch PA firm the plate PL or the tissue sample SA, an antibody AB that has not bound to the target protein (that is, residual antibody AB) may be removed from the plate PL. When the patch PA is separated from the plate PL, the water film WF, which has been formed, may move along with the patch PA, and the residual antibody AB may be captured in the water film WF and absorbed into the patch PA. The residual antibody AB may be removed from the plate PL when the patch PA is separated fawn the plate PL.

When, as described above, the antibody AB bind specifically to the target protein and an identification label is attached to the antibody AB itself, the identification label may be detected in a state in which only the antibody AB is provided, and the target protein may be detected. However, when an enzyme is attached to the antibody AB, a patch PA that contains a substrate SU may be may be separately provided and used. Providing the substrate SU to the reaction region by using the patch PA which contain the substrate SU may be similar to the above-described providing of the antibody AB (see FIGS. 57 and 58).

Although a method of identifying a target protein using an antibody by Direct Enzyme-Linked Immunosorbent Assay (ELISA) has been described with respect to the present embodiment, a method using Indirect ELISA may also be used. In this case, Indirect ELISA refers to detecting a target substance using a first antibody that binds specifically to the target substance and a second antibody that has a property of binding specifically to the first antibody and has an identification label attached thereto.

Hereinafter, a case in which diagonals is performed by staining a target substance to be detected TS included in a tissue sample SA and a case in which diagnosis is performed by assigning fluorescence to a target substance to be detected TS will be separately reviewed. However, each diagnosis method is not necessarily performed independently, and the two diagnosis methods may also be performed together in a single diagnostic process. In other wards, the issue methods disclosed herein are not necessarily independent of each other or performed as separate processes. For example, a bright-field image and a fluorescence image of the same tissue sample SA may be obtained through a single process. When a plurality of diagnostic methods are used in a single diagnostic process, information acquired in accordance with the diagnostic methods may be different.

4.2.1 Performance of Staining Diagnosis—Acquisition of Bright-Field Image

Staining may be used to observe a tissue sample SA. Since most elements that constitute a tissue do not exhibit color, diagnosis may be performed by staining the tissue sample SA so that components of a tissue are distinguishable and are easy to observe.

The staining herein includes, in addition to using a substance that exhibits color to stain a target substance TS so that the target substance TS exhibits color, using a label capable of generating a precipitation and locating a color label in the target substance TS. Specifically, the staining of the tissue may be performed using vital staining, staining using selective dissolution, staining using a chemical color reaction, staining using a metal infiltration technique, staining using a staining reagent, or the like.

A few embodiments of a method of performing tissue diagnosis by staining a portion of a tissue sample SA will be described below.

Performing tissue diagnosis according to the present application may include placing a tissue sample SA in a reaction region, providing a staining substance to the tissue sample SA by using a patch PA, and acquiring a bright-field image of the tissue sample SA located in the reaction region.

The placing of the tissue sample SA in the reaction region may include placing the tissue sample SA on the plate PL. The placing of the tissue sample SA in the reaction region may include fixating the tissue sample SA on the reaction region or the plate PL. The fixating of the tissue sample SA may be performed by drying the tissue sample SA.

The providing of the staining substance to the tissue sample SA may include providing a staining substance for determining the morphology of cells that constitute the tissue sample SA. The patch PA may contain the staining substance for determining the morphology of cells that constitute the tissue sample SA and provide the staining substance to the sample SA or the reaction region.

The staining substance for determining the morphology of cells that constitute the tissue sample SA may be an ionic staining substance. In other words, the staining substance may exhibit acidity and assign color to a portion of the tissue sample SA that exhibits basicity. Alternatively, the staining substance may exhibit basicity and assign color to a portion of the tissue sample SA that exhibits acidity.

The staining substance for determining the morphology of cells that constitute the tissue sample SA may be an immunostaining substance. The staining substance may include an antibody that binds specifically to a target protein by an antigen-antibody reaction. The antibody that binds specifically to the target protein may indicate a region in which the target protein is distributed. Therefore, morphological analysis on the tissue sample SA may be performed by analyzing the region in which the target protein is distributed.

The providing of the staining substance to the tissue sample SA may include providing a staining substance for labeling the target protein. The patch PA may contain the staining substance for labeling the target protein and provide the staining substance to the sample SA or the reaction region.

The staining substance for labeling the target protein may be a staining substance that uses an antigen-antibody reaction. In other words, the target protein may be an antigen related to a specific disease, and the providing of the staining substance may include providing an antibody, which binds specifically to the antigen and has an enzyme attached thereto, and a substrate SU, which is catalyzed by the enzyme and generates a precipitation which exhibits color.

The staining substance for labeling the target protein may induce a color reaction in a region in which the target protein is located. In this case, the tissue diagnosis according to the present embodiment may be performed by performing colorimetric measurement according to the color reaction and obtaining information on a presence of target proteins, distribution of target proteins, and the like.

The providing of the staining substance to the tissue sample SA may include providing a staining substance for labeling a target base sequence. The patch PA may contain a staining substance for labeling a DNA (or a specific base sequence) included in the tissue sample SA and provide the staining substance to the tissue sample SA or the reaction region.

In this case, the target base sequence to be detected may be a target base sequence that causes a disease to be diagnosed.

The staining substance for labeling the target base sequence may be for detecting the target base sequence by in situ hybridization (ISH). The staining substance for labeling the target sequence may use a nucleic acid probe to detect a target base sequence. Specifically, the staining substance for labeling the target base sequence may include a probe that binds specifically (or complementarily) to the target base sequence and generates color precipitation substance. The detecting of the target base sequence may be performed using chromogenic in situ hybridization (CISH).

A diagnostic method for detecting a target base sequence may be used to determine whether cancer (e.g., breast cancer) has developed or whether a person is infected with human papillomavirus.

The policing of the staining substance may be performed by contacting a patch PA which contains the staining substance with the reaction region (hereinafter, the reaction region is defined as a concept that encompasses the sample SA and the reaction region) and separating the patch PA from the reaction region. According to a method of staining the tissue sample SA according to the present application, in comparison to a conventional method in which staining of a tissue is performed by applying a large amount of staining reagent, a significantly smaller amount of staining reagent is required in staining, and thus diagnosis may be more economically performed.

In this case, the providing of the staining substance may be performed by contacting the patch PA with the reaction region so that the staining substance becomes movable to the reaction region, and the staining substance binding to a staining target substance TS included in the reaction region. In this case, when the patch PA is separated from the reaction region, a staining substance that has not bound to the staining target substance TS of the staining substance that has moved to the reaction region may be absorbed into the patch PA.

Specifically, the providing of the staining substance may be performed by contacting the patch PA with the reaction region so that, through a water film WF formed in the vicinity of a contact region, the staining substance becomes movable to the reaction region and binds to the staining target substance TS included in the reaction region. In this case, when the patch PA is separated from the reaction region, a staining substance that has not bound to the staining target substance TS of the staining substance that has moved to the reaction region may be captured in the water film WF and absorbed into the patch PA.

When the staining substance is provided using the patch PA as described above, just by separating the patch PA from the reaction region, the staining substance that has not bound to the staining target substance TS may be removed from the sample SA. Therefore, when the tissue diagnosis method according to the present application is used, an amount of consumed reagent may be reduced and prompt diagnosis may be performed in comparison to a conventional method in which a washing process has to be performed using a separate washing solution to remove a substance that has not bound specifically to a staining target substance TS (that is, residual staining substance).

The acquiring of the bright-field image of the tissue sample SA may include acquiring an image in which a target substance which becomes a basis of the tissue diagnosis (that is, the staining target substance TS) is stained, color-developed, or colored. Alternatively, acquiring of the bright-field image may include acquiring an image in which color particles are bound to the target substance TS or a pigment is precipitated on the target substance TS. The bright-field image may be an image in which some elements which are a basis of the morphological analysis of cells that constitute the tissue sample SA are stained or colored. The bright-field image may be an image in which a target protein included in the tissue sample SA is color-labeled. The bright-field image may be an image in which a DNA or target base sequence included in the tissue sample is color-labeled.

The acquiring of the bright-field image of the tissue sample SA may be performed using bright field microscopy. The acquiring of the bright-field image of the tissue sample SA may be performed using a light microscope. The acquiring of the bright-field image may include making light incident on one surface of a plate PL on which the tissue sample SA is placed and recognizing the light which has been incident and has passed through the tissue sample SA to acquire the bright-field image. The acquiring of the bright-field image of the tissue sample SA may be performed using an imaging module such as a complementary metaloxide semiconductor (CMOS) image sensor and a charge coupled device (CCD) image sensor. The acquiring of the bright-field image may include acquiring a single image including an entire region of the tissue sample SA. Alternatively, the acquiring of the bright-field image may include acquiring a plurality of unit images by separately imaging a plurality of unit regions of the tissue sample SA placed in the reaction region and combining the plurality of acquired unit images.

The tissue diagnosis according to the present embodiment may further include analyzing the acquired bright-field image.

The analyzing of the acquired image may include performing morphological analysis.

For example, the analyzing of the acquired image may be performed to determine whether cancer has developed from the sample SA. Specifically, a presence of an irregular morphology of a nucleus may be determined from morphologies of nuclei included in the tissue sample SA, an adhesiveness between cells may be determined from a binding state between cells included in the tissue sample SA, or whether the arrangement of cells included in the tissue sample SA is uniform may be determined to determine whether cancer has developed from the tissue sample SA. However, the above subjects of determination are merely examples, and various other morphological aspects may be applied to determine a presence of tumor cells in the tissue sample SA.

Figure 42:
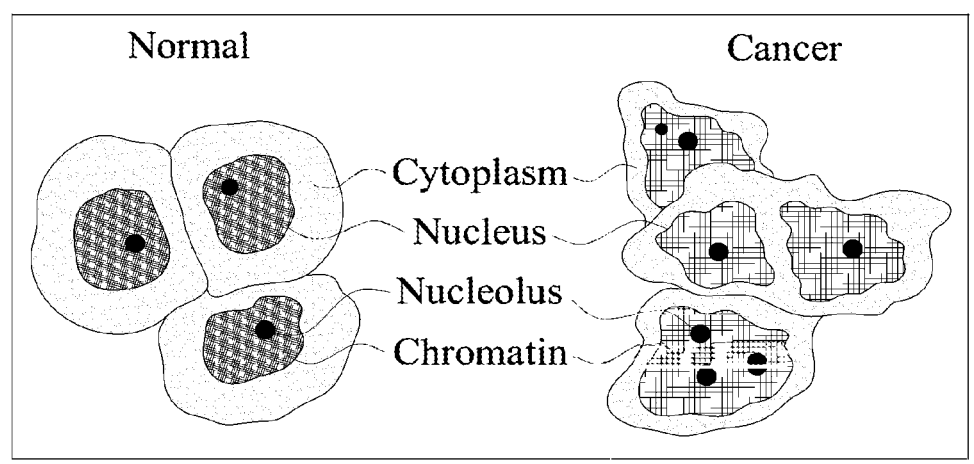
FIG. 42 illustrates as example of morphological diagnosis in an embodiment of a tissue diagnosis method according to the present application.

For example, FIG. 42 schematically illustrates tumor cells and normal cells in an embodiment of tissue diagnosis according to the present application. Referring to FIG. 42, normal cells have uniform morphology, have a large cytoplasm and a nucleus for each cell, the nucleus has a nucleolus, and chromatins are densely distributed in the nucleus. In contrast, tumor cells have irregular morphology, have a small cytoplasm and multiple nuclei for each cell, a plurality of nucleoli may be present in each nucleus, and chromatins may be sparsely distributed in the nucleus. Using such differences in morphological characteristics of tumor cells and normal cells, the presence of tumor cells may be determined or a distribution of tumor cells may be obtained from an image of a tissue sample SA.

The analyzing of the acquired image may include obtaining a distribution of a substance to be detected TS. For example, a distribution of target proteins may be obtained. In other words, a presence of a target antigen related to a disease to be diagnosed or positions at which the antigen is distributed in the tissue sample SA may be obtained. Alternatively, a distribution of a target base sequence may be obtained. For example, whether a target base sequence related to a disease to be diagnosed is included in the tissue sample SA and a distribution of the target base sequence in the tissue sample SA may be obtained from the tissue sample SA.

The above-described image analysis may be performed by artificial intelligence. In other woods, the above-described detection of a basis of diagnosis from an image or acquisition of a diagnosis result by analyzing the image may be performed by machine-learned artificial intelligence.

The acquired image is not only used in diagnosis of cancer or tumor but may also be used in observing a cell organelle, predicting a disease with likelihood of development, and managing a disease that developed in the past.

The tissue diagnosis according to the present embodiment may include measuring an amount of target substance TS included in the tissue sample SA. The target substance TS may include a substance such as a target protein and a targetbase sequence which is a basis of diagnosis.

The measuring of the amount of target substance TS may be performed by measuring an amount of stained target substance TS in the substance sample SA.

Alternatively, the measuring of the amount of the target substance TS included in the tissue sample SA may be performed using an electrochemical method. In other words, in the measuring of the amount of target substance TS, the amount of substance provided from the patch PA to the reaction region may vary in accordance with the amount or target substance TS included in the tissue sample SA, in providing of the staining substance to the tissue samples SA or the reaction region by using the patch PA. In this case, the measuring of the amount of target substance TS included in the tissue sample SA may be performed by measuring a change in an electrical characteristic of the patch PA or the plate PL on which the reaction region is placed that occurs due to the providing of substance from the patch PA to the reaction region.

However, the obtaining of the amount of target substance TS is not necessarily performed independently from the above-described acquisition of the image of the tissue sample SA, and the acquiring of the image to diagnose the sample SA and the measuring of the amount of target substance TS included in the sample SA may also be simultaneously performed.

4.2.2 Performance of Fluorescence Diagnosis—Acquisition of Fluorescence Image

Performing tissue diagnosis according to the present application may include placing a tissue simple SA in a reaction region, providing a fluorescence substance to the tissue sample SA by using a patch PA, and acquiring a fluorescence image of the tissue simple SA placed in the reaction region.

The placing of the tissue sample SA in the reaction region may include placing the tissue sample SA on a plate PL. The placing of the tissue sample SA in the reaction region may include fixating the tissue sample SA on the reaction region or the plate PL. The fixating of the tissue sample SA may be performed by drying the tissue sample SA.

The providing of the fluorescent substance to the tissue sample SA by using the patch PA may include providing a fluorescent substance for determining the morphology of cells that constitute the tissue sample SA. The patch PA may contain a fluorescent substance for determining the morphology of cells that constitute the tissue sample SA and provide the fluorescent substance to the sample SA or the reaction region.

The fluorescent substance for determining the morphology of cells that constitute the tissue sample SA may be an immunological fluorescent substance. The fluorescent substance may include an antibody that binds specifically to a target protein by an antigen-antibody reaction. The antibody which binds specifically to the target protein may indicate a region in which the target protein is distributed. The morphological analysis of the tissue sample SA may be performed by analyzing the region in which the target protein is distributed.

The providing of the fluorescent substance to the tissue sample SA by using the patch PA may induct providing the fluorescent substance for detecting a target protein from the tissue sample SA. The fluorescent substance may be a fluorescent substance for labeling the target protein. The patch PA may contain a fluorescent substance for labeling the target protein and provide the fluorescent substance to the sample SA or the reaction region.

The fluorescent substance for labeling the target protein may be a fluorescent substance that uses an antigen-antibody reaction. The target protein may be an antigen related to a specific disease. The providing of the fluorescent substance may include providing an antibody, which binds specifically to the antigen and has an enzyme attached thereto, and a substrate SU, which is catalyzed by the enzyme and generates a precipitation which exhibits color.

The fluorescent substance for labeling the target protein may induce a color reaction in a region in which the target protein is located. In this case, the tissue diagnosis according to the present embodiment may be performed by performing colorimetric measurement according to the color reaction and obtaining information on a presence of target proteins, distribution of target proteins, and the like.

The providing of the fluorescent substance to the tissue sample SA by using the patch PA may include providing a fluorescent substance for detecting a DNA from the tissue sample SA. The fluorescent substance may be a fluorescent substance for labeling a DNA or a specific genetic included in the tissue sample SA. The patch PA may contain a fluorescent substance for labeling a DNA (or a specific base sequence) included in the tissue sample SA and provide the fluorescent substance to the tissue sample SA or the reaction region.

The fluorescent substance may be a substance for labeling a DNA included in the tissue sample SA. The fluorescent substance may bind to a DNA included in the tissue sample SA and facilitate obtaining of a distribution of DNA (that is, a distribution of nuclei) and the morphology of nuclei from the tissue sample SA. The fluorescent substance may be 4',6-diamidino-2-phenylindole (DAPI).

The fluorescent substance for labeling the target base sequence may be for detecting the target base sequence by in situ hybridization. The fluorescent substance for labeling the target sequence may use a nucleic acid probe to detect a target base sequence. Specifically, the fluorescent substance for labeling the target base sequence may include a probe that binds specifically (or complementarily) to the target base sequence and generates a color precipitation substance. The detecting of the target base sequence may be performed using fluorescence in situ hybridization (FISH).

The providing of the fluorescent substance to the reaction region may be performed by contacting a patch PA which contains the fluorescent substance with the reaction region and separating the patch PA from the reaction region. According to a fluorescence-labeling method according to the present application, in comparison to a conventional method in which fluorescent labeling is performed by applying a large amount of fluorescence staining reagent, a significantly smaller amount of staining reagent is required.

In this case, the providing of the fluorescent substance may be performed by contacting the patch PA with the reaction region so that the fluorescent substance becomes movable to the reaction region, and the fluorescent substance binding to a labeling target substance TS included in the reaction region. In this case, when the patch PA is separated from the reaction region, a fluorescent substance that has not bound to the labeling target substance TS of the fluorescent substance that has moved to the reaction region may be absorbed into the patch PA.

Specifically, the providing of the fluorescent substance may be performed by contacting the patch PA with the reaction region so that, through a water film WF formed in the vicinity of a contact region, the fluorescent substance becomes movable to the reaction region and binds to the labeling target substance TS included in the reaction region. In this case, when the patch PA is separated from the reaction region, a fluorescent substance that has not bound to the labeling target substance TS of the fluorescent substance that has moved to the reaction region may be captured in the water film WF and absorbed into the patch PA.

A conventional method of labeling fluorescence to a sample SA essentially requires a process in which a separate washing solution is poured to rinse the sample SA in order to remove a fluorescent substance that has not bound to a labeling target substance TS from a sample SA. In contrast, when the fluorescent substance is provided using the patch PA as in the present application, the fluorescent substance that has not bound to the labeling target substance TS may be removed from the sample SA just by separating the patch PA from the reaction region. Therefore, fluorescence may be labeled to a tissue sample SA by a more economical and convenient procedure in comparison to the conventional method.

The acquiring of the fluorescence image of the tissue sample SA may include acquiring an image in which target substances TS, which are bases of the tissue diagnosis, are fluorescence-labeled. The fluorescence image may be an image in which same elements which are a basis of the morphological analysis of cells that constitute the tissue sample SA are fluorescence-labeled. The fluorescence image may be an image in which a target protein included in the tissue sample SA is fluorescence-labeled. The fluorescence image may be an image in which a DNA or target base sequence included in the tissue sample SA is fluorescence-labeled.

The acquiring of the fluorescence image of the tissue sample SA may be performed using a fluorescent microscope. The acquiring of the fluorescence image may include making light which is in a specific wavelength band incident on the reaction region or the tissue sample SA and detecting the light in the specific wavelength band emitted from the reaction region or the tissue sample SA to acquire the fluorescence image. In this case, a filter that allows only light in a suitable wavelength band to peas therethrough may be used. The detecting of the fluorescence may be performed by a method in which light is made incident on the plate PL and fluorescence emitted horn the plate PL is measured.

The acquiring of the fluorescence image of the tissue sample SA may be performed using an imaging module such as a CMOS image senior and a CCD image sensor. The acquiring of the fluorescence image may include acquiring a single image including an entire region of the tissue sample SA, or acquiring a plurality of unit images for each unit region and combining the plurality of acquired unit images. In the measuring of the fluorescence, preferably, an opaque black plate or an opaque white plate may be used as the plate PL when measuring the fluorescence.

The tissue diagnosis according to the present embodiment may further include analyzing the acquired fluorescence image.

The analyzing of the acquired image may include performing morphological analysis.

For example, the analyzing of the acquired image may be performed to determine whether cancer has developed from the sample SA. Specifically, a presence of an irregular morphology of a nucleus may be determined from morphologies of nuclei included in the tissue sample SA, an adhesiveness between cells may be determined from a binding state between cells included in the time sample SA, or whether the arrangement of cells included in the tissue sample SA is uniform may be determined to determine whether cancer has developed from the tissue sample SA.

However, the above subjects of determination are merely examples, and various other morphological aspects may be applied to determine a presence of tumor cells in the tissue sample SA.

The determination of the presence of tumor cells may be similar to that described above with reference to FIG. 42 in the embodiment of staining diagnosis. In other words, as illustrated in FIG. 42, using the differences between characteristics of normal cells and tumor cells in terms of cytoplasm, nucleus, chromatin, and the like, the presence of tumor cells may be determined or a distribution of tumor cells may be obtained from an image of a tissue sample SA.

The analyzing of the obtained image may include obtaining a distribution of a target substance to be detected TS. For example, a distribution of target proteins may be obtained. In other words, a presence of a target antigen related to a disease to be diagnosed or positions at which the antigen is distributed in the tissue sample SA may be obtained. Alternatively, a distribution of a target base sequence may be obtained. For example, whether a target base sequence related to a disease to be disposed is included in the tissue sample SA and a distribution of the target base sequence in the tissue sample SA may be obtained from the tissue sample SA.

The above-described image analysis may be performed by artificial intelligence. In other words, the above-described detection of a basis of diagnosis from an image or acquisition of a diagnosis result by analyzing the image may be performed by machine-learned artificial intelligence.

The acquired image is not only used in diagnosis of cancer or tumor but may also be used in observing a cell organelle, predicting a disease with likelihood of development, and managing a disease that developed in the past.

The tissue diagnosis according to the present embodiment may include measuring an amount of target substance TS included in the tissue sample SA. The target substance TS may include a substance such aa a target protein and a target base sequence which is a basis of diagnosis.

The measuring of the amount of target substance TS may be performed by measuring an amount of fluorescence generated in accordance with the amount of target substance TS. Alternatively, the measuring of the amount of the target substance TS included in the tissue sample SA may be performed using an electrochemical method. In other words, in the measuring of the amount of target substance TS, the amount of substance provided from the patch PA to the reaction region may very in accordance with the amount of target substance TS included in the tissue sample SA in providing of the staining substance or fluorescence substance to the tissue sample SA or the reaction region by using the patch PA. In this case, the measuring of the amount of target substance TS included in the tissue sample SA may be performed by measuring a change in an electrical characteristic of the patch PA or the plate PL on which the reaction region is placed that occurs due to the providing of substance from the patch PA to the reaction region.

However, the measuring of the amount of target substance TS included in the tissue sample SA is not necessarily performed independently from the above-described acquisition of the fluorescence image, and the acquiring of the image to diagnose the sample SA and the measuring of the amount of target substance TS included in the sample SA may also be simultaneously performed.

4.2.3 Image Acquisition for Multiple Targets

Hereinafter, a tissue diagnosis method for detecting a plurality of target substances TS will be described with reference to FIGS. 39 to 41.

Figure 39:
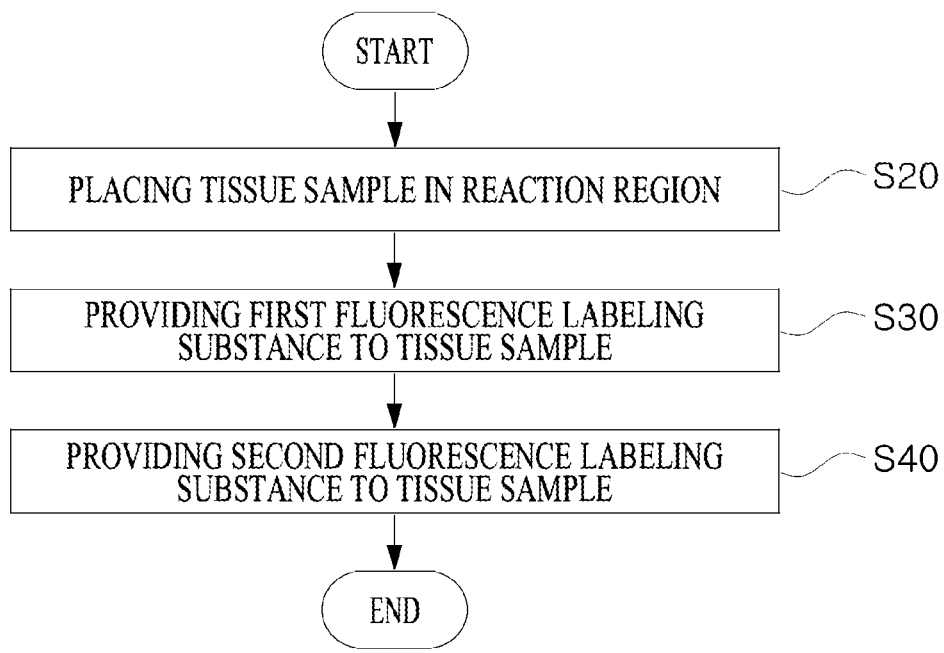
FIG. 39 illustrates a flowchart for describing a case in which a plurality of target substance are detected, as an example of a tissue diagnosis method according to the present application.

Referring to FIG. 39, a tissue diagnosis method for detecting a plurality of target substances TS, which is a tissue diagnosis method according to an embodiment of the present application, may include placing a tissue sample SA in a reaction region (S20), providing a first fluorescent substance to the tissue sample SA (S30), and providing a second fluorescent substance to the tissue sample SA (S40).

The placing of the tissue sample SA in the reaction region (S20) may be performed similarly as in the above-described embodiments.

The providing of the first fluorescent substance to the tissue sample SA (S30) may be performed using a patch PA that contains a first fluorescence labeling substance for specifically labeling a first target substance.

The providing of the second fluorescent substance to the tissue sample SA (S40) may be performed using a patch PA than contains a second fluorescence labeling substance for specifically landing a second target substance.

Figure 40:
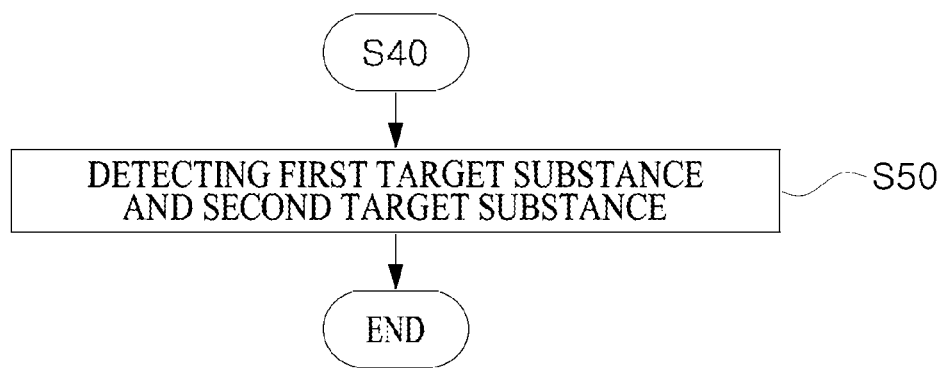
FIG. 40 illustrates a flowchart for describing a case in which a plurality of target substances are detected, as an example of a tissue diagnosis method according to the present application.

Referring to FIG. 40, the tissue diagnosis method for detecting a plurality of target substances TS according to the present embodiment may further include detecting a first target substance TS and a second target substance TS (S50). The detecting of the first target substance TS and the second target substance TS (S50) may be performed after the providing of the second fluorescence labeling substance to the tissue sample SA.

In this case, a wavelength band from which fluorescence emitted from the first fluorescence labeling substance is detected and a wavelength band front which fluorescence emitted from the second fluorescence labeling substance is detected may be different from each other, and the detecting of the first target substance TS and the second target substance TS (S50) may include detecting the first target substance TS and the second target substance TS which are included in the tissue ample SA (S50).

Figure 41:
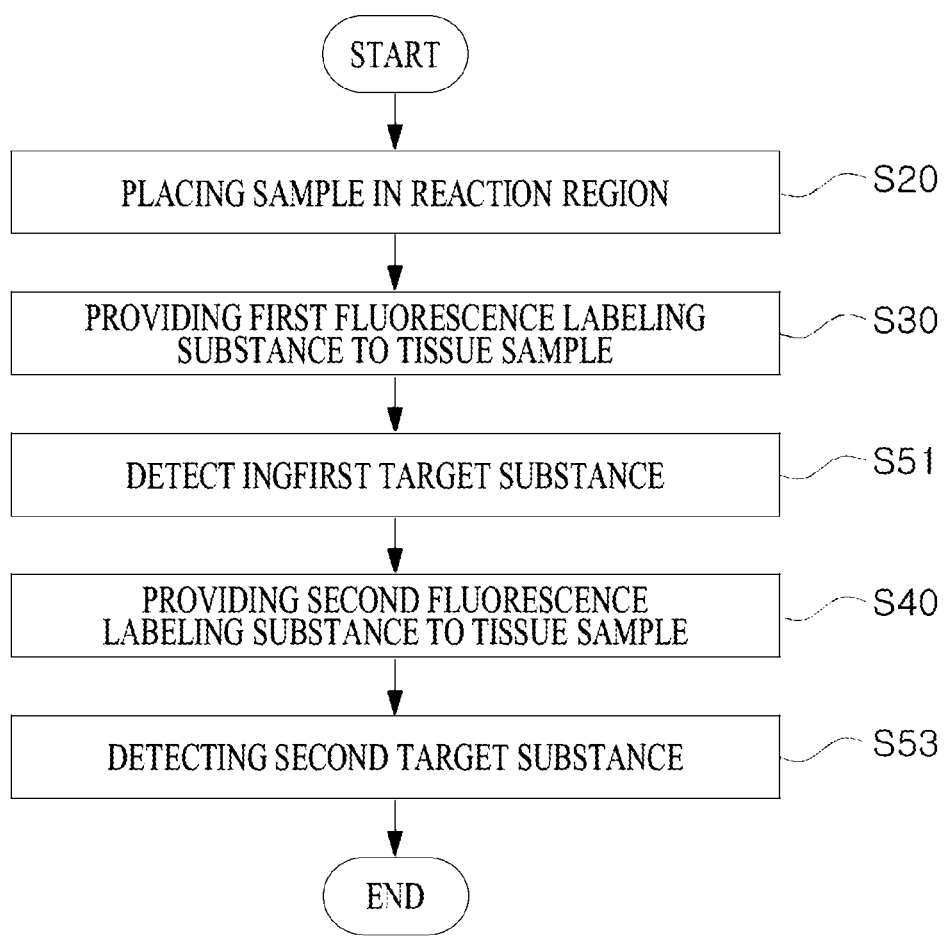
FIG. 41 illustrates a flowchart for describing a case in which a plurality of target substances are sequentially detected, as an example of a tissue diagnosis method according to the present application.

Referring to FIG. 41, the tissue diagnosis method for detecting a plurality of target substances TS according to the present embodiment may include placing a tissue sample SA in a reaction region (S20), providing a first fluorescent substance to the tissue sample SA (S30), detecting a first target substance TS (S51), providing a second fluorescent substance to the tissue sample SA (S40), and detecting a second target substance TS (S53).

The placing of the tissue sample SA in the reaction region (S20), the providing of the first fluorescent substance to the tissue sample SA (S30), and the providing of the second fluorescent substance to the tissue simple SA (S40) may be similarly performed as those in the above-described embodiments.

The detecting of the first target substance TS (S51) be performed after the providing of the first fluorescence labeling substance to the tissue sample SA, and may include detecting the first target substance TS included in the tissue sample SA by detecting fluorescence emitted from the first fluorescence labeling substance.

The detecting of the second target substance TS (S53) may be performed after the providing of the second fluorescence labeling substance to the tissue sample SA, and may include detecting the second target substance TS included in the tissue sample SA by detecting fluorescence emitted from the second fluorescence labeling substance.

In this ease, a wavelength hand from which fluorescence emitted from the first fluorescence labeling substance is detected and a wavelength band from which fluorescence emitted from the second fluorescence labeling substance is detected may at least partially overlap each other, and the detecting of the fluorescence emitted from the second fluorescence labeling substance may be performed by comparing fluorescence detected from the tissue sample SA after the second fluorescence labeling substance is provided to the tissue sample SA and fluorescence detected from the tissue sample SA before the second fluorescence labeling substance is provided to the tissue sample SA.

The tissue diagnosis according to the present application may be used to detect a plurality of targets. The tissue diagnosis method for detecting a plurality of targets may be performed using a plurality of patches PA.

A target to be detected may refer to a target substance TS that becomes a basis of tissue diagnosis. For example, the target may refer to a DNA included in the tissue sample SA, a specific base sequence, a specific protein, a cellular component, or the like. In the tissue diagnosis, a plurality of targets may be detained through a single process. The single process may refer to using a single plate PL. The single process may refer to using a single sample SA.

In the tissue diagnosis according to the present application, a plurality of targets may be detected from a process of acquiring a single bright-field image. In other words, according to the tissue diagnosis according to the present application, a plurality of targets may be detected from a single bright-field image. In this case, a single image may refer to an image of an entire region of the tissue sample SA placed on the plate PL, or an image formed by combining a plurality of unit images respectively acquired for a plurality of unit regions included to the plate PL.

The plurality of targets may be displayed in different colors in the bright-field image. For example, a nucleus included in the tissue sample SA may be displayed in blue color, and a cytoplasm may be displayed in red color.

In the tissue diagnosis according to the present application, a plurality of targets may be detected by a process of acquiring a single fluorescence image. The plurality of targets may be detected from a single fluorescence image. The plurality of targets may be detected from a plurality of fluorescence images acquired in a single process. Fluorescences detected from simmer wavelength bands may be labeled to the plurality of targets.

Fluorescences detected from different wavelength bands may be labeled to the plurality of targets. For example, a nucleus included in the tissue sample SA may be displayed with blue fluorescence, and a microtubule may be displayed with green fluorescence.

In the present embodiment, the plurality of targets may be a plurality of target proteins. In other words, according to an embodiment of the present application, a plurality of target proteins may be detected by a process of acquiring a mingle fluorescence image.

As an example of tissue diagnosis for detecting a plurality of targets according to the present application, tissue diagnosis in which a plurality of target proteins are detected using an immunological method will be described below.

As an example of tissue diagnosis according to the present application, a tissue diagnosis method for detecting a plurality of target proteins may include fixating a sample SA on a plate PL, providing multiple types of fluorescence labeling substances that bind specifically to the plurality of target proteins to the plate PL, and detecting the plurality of target proteins. In the present embodiment, the fluorescence labeling substance may refer to an antibody to which a fluorescence label as attached. The fluorescence labeling substance may refer to an antibody to which an enzyme, which reacts with a substrate SU and generates fluorescence, is attached.

The fixating of the sample SA as the plate PL may be similar as that in the above-described embodiments.

The providing of the multiple types of fluorescence labeling substances that bind specifically to the plurality of target proteins to the plate PL may include providing a first fluorescence labeling substance and a second fluorescence labeling substance. In other words, the plurality of target proteins may include a first target protein and a second target protein, and the multiple types of fluorescence labeling substances may include a first fluorescence labeling substance that binds specifically to the first target protein and a second fluorescence labeling substance that binds specifically to the second target protein. In this case, a wavelength band from which fluorescence emitted from the first fluorescence labeling substance is detected and a wavelength band from which the second fluorescence labeling substance is detected may be different from each other.

The detecting of the plurality of targets may include acquiring an image in which a region in which each target is distributed in the tissue sample SA is displayed. Alternatively, the detecting of the plurality of targets may include measuring an amount of the plurality of targets included in the tissue sample SA.

The detecting of the plurality of target proteins may include acquiring a fluorescence image of the tissue sample SA. The detecting of the plurality of target proteins may include performing quantitative analysis on the plurality of target proteins.

The above-described method of detecting the plurality of target proteins may be performed using a plurality of patches PA. For example, the plurality of patches PA may include a first patch PA that contains the first fluorescence labeling substance and a second patch PA that contains the second fluorescence labeling substance.

Specifically, the method of detecting targets using the plurality of patches PA may include fixating a sample SA on a plate PL, providing a first fluorescence labeling substance which reacts specifically with a first target protein to the plate PL by using the first patch PA that contains the first fluorescence labeling substance, and providing the second fluorescence labeling substance which reacts specifically with a second target protein to the plate PL by using the second patch PA that contains the second fluorescence labeling substance. A wavelength band from which fluorescence which labels the first fluorescence labeling stance is detected and a wavelength band from which fluorescence which labels the second fluorescence labeling substance is detected may be different from each ether.

According to an embodiment, the method of detecting targets using the plurality of patches PA may include, after the providing of the first fluorescence labeling substance to the plate PL or before the providing of the second fluorescence labeling substance to the plate PL, detecting the first target protein included in the tissue sample SA. Also, the method of detecting targets using the plurality of patches PA may include, after the providing of the second fluorescence labeling substance to the plate PL, detecting the second target protein included in the tissue sample SA. In other words, the first target protein may be detected when the first fluorescence labeling substance is provided to the plate PL, and the second target protein may be detected when the second fluorescence labeling substance is provided to the plate PL.

According to another embodiment, the method of detecting targets using the plurality of patches PA may further include, after the providing of the second fluorescence labeling substance to the plate PL, detecting the first target protein and the second target protein which are included in the tissue sample SA. In other words, the first target protein and the second target protein may be detected after the first fluorescence labeling substance and the second fluorescence labeling substance are provided to the plate PL.

When a plurality of target proteins are detected using a plurality of patches PA as in the present embodiment, a wavelength band from which fluorescence labeled to the first target protein is detected and a wavelength band from which fluorescence labeled to the second target protein is detected may be similar to each other. In this case, while the first target protein is detected when the first fluorescence labeling substance is provided to the plate PL and the second target protein is detected when the second labeling substance is provided to the plate PL, the detecting of the second target protein may be performed by comparing fluorescence acquired upon the detection of the first target protein and fluorescence obtained for the detection of the second target protein.

Figure 43:
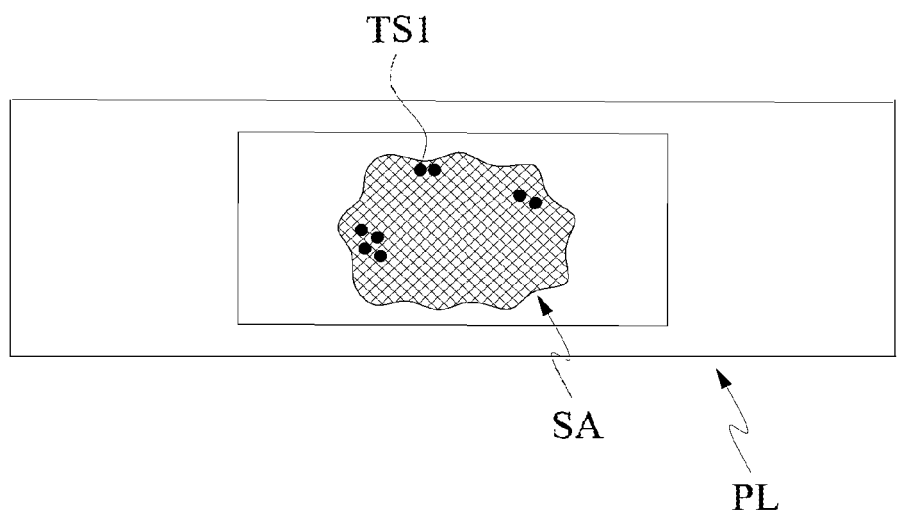
FIG. 43 schematically illustrates a part of a case in which it is desired to detect a plurality of target substances, as an example of a tissue diagnosis method according to the present application.
Figure 44:
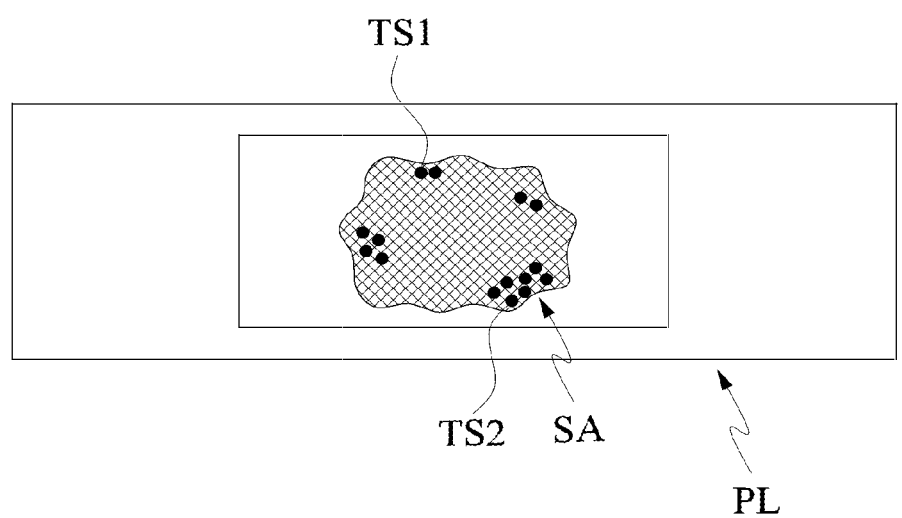
FIG. 44 schematically illustrates a part of a case in which it is desired to detect a plurality of target substances, as an example of a tissue diagnosis method according to the present application.

FIGS. 43 and 44 schematically illustrate a part of a method of detecting a plurality of target substances TS, as an example of a tissue diagnosis method according to the present application. Referring to FIGS. 43 and 44, the tissue diagnosis method according to the present application may be used when it is desired to detect a first target substance TS1 and a second target substance TS2 which are included in a tissue sample SA. Description with reference to FIG. 41 will be given below.

A tissue diagnosis method of the present application may include placing a sample SA in a reaction region (S20), providing a first fluorescence labeling substance to the tissue sample SA (S30), and detecting a first target substance TS1 (S51) (see FIG. 43). Also, after the detecting of the first target substance TS1 (S51), the tissue diagnosis method of the present application may include providing a second fluorescence labeling substance to the tissue sample SA (S40), and detecting a second target substance TS2 (S53) (see FIG. 44). In the present embodiment, when a wavelength band from which first fluorescence emitted from the first target substance TS, which is fluorescence-labeled by the first fluorescence labeling substance, overlaps with a wavelength band from which second fluorescence emitted from the second target substance TS, which is fluorescence-labeled by the second fluorescence labeling substance, during the detecting of the second target substance TS2 (S53), differentiation between the second target substance TS2 and the first target substance TS1 may be difficult due to the fluorescence labeled to the first target substance TS1. In this case, the detecting of the second target substance TS may be performed by comparing fluorescence detected font the tissue sample SA after the second fluorescence labeling substance is provided to the tissue sample SA and fluorescence detected from the tissue sample SA before the second fluorescence labeling substance is provided to the tissue sample SA. For example, when, as in FIGS. 43 and 44, the first target substance TS1 is detected together with the second target substance TS2 upon the detection of the second target substance TS2, the second target substance TS2 may be detected by comparing fluorescence labels detected before and after the providing of the second fluorescence labeling substance to the plate PL. By detecting each of the first target substance TS1 and the second target substance TS2 as described above, a position at which each target substance TS is distributed in the tissue sample SA and the amount of each target substance TS included in the tissue sample SA may be obtained.

FIGS. 43 to 47 schematically illustrate a peat of a method of detecting a plurality of target substances TS, as another example of the tissue diagnosis method according to the present application. Referring to FIGS. 43 to 47, the tissue diagnosis method according to the present application may be used when it is desired to detect a third target substance TS3 and a fourth target substance TS4 which are included in the tissue sample SA. Description with reference to FIG. 41 will be given below.

Figure 45:
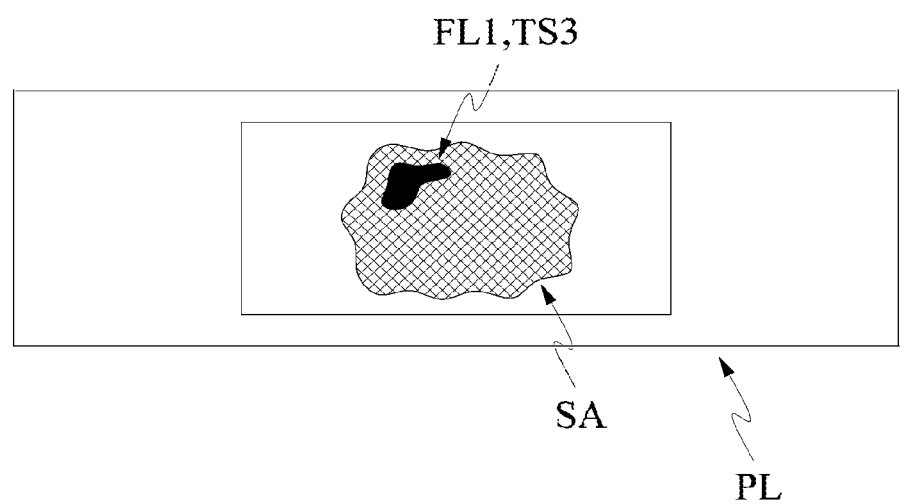
FIG. 45 schematically illustrates a part of a case in which it is desired to detect a plurality of target substances, as an example of a tissue diagnostic method according to the present application.
Figure 46:
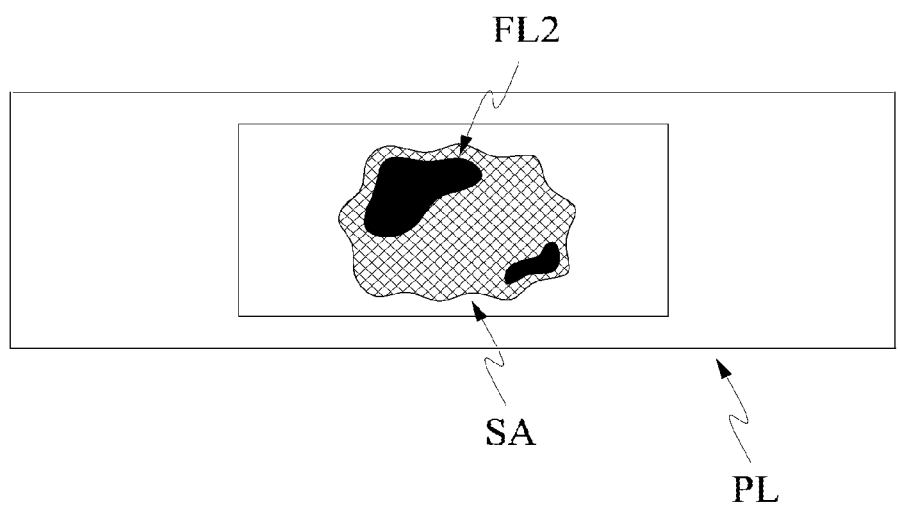
FIG. 46 schematically illustrates a part of a case in which it is desired to detect a plurality of target substances, as an example of a tissue diagnosis method according to the present application.
Figure 47:
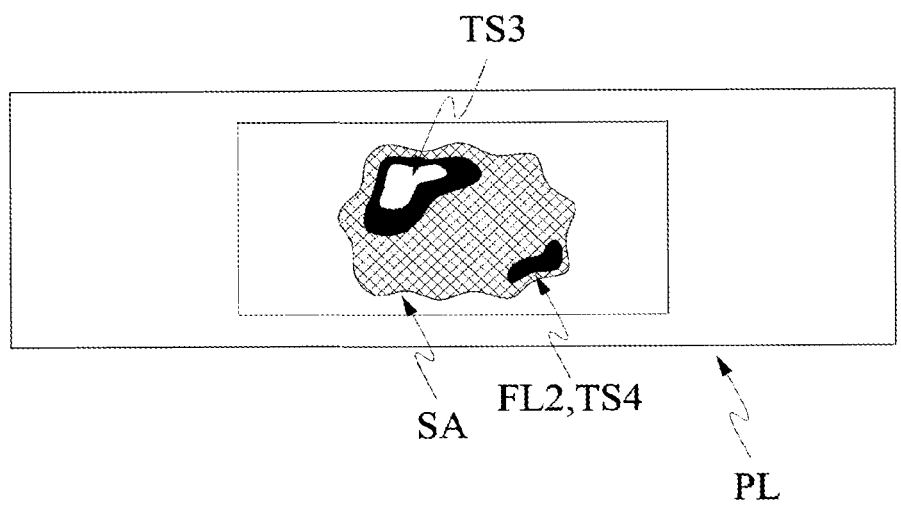
FIG. 47 schematically illustrates a part of a case in which it is desired to detect a plurality of target substances, as an example of a tissue diagnosis method according to the present application.

A tissue diagnosis method of the present application may include placing a sample SA in reaction region (S20), providing a first fluorescence labeling substance FL1 to the tissue sample SA (S30), and detecting a third target substance TS3 (S51) (see FIG. 45). Also, after the detecting of the third target substance TS3 (S51), the tissue diagnosis method of the present application may include providing a second fluorescence labeling substance FL2 to the tissue sample SA (S40), and detecting a fourth target substance TS4 (S53) (see FIG. 46). In the present embodiment, when a wavelength band from which first fluorescence emitted from the third target substance TS3, which is fluorescence-labeled by the first fluorescence labeling substance FL1, overlaps with a wavelength band from which second fluorescence emitted from the fourth target substance TS4, which is fluorescence-labeled by the second fluorescence labeling substance FL2, during the detecting of the fourth target substance TS4 (S53), identification of the fourth target substance TS4 may be difficult due to the fluorescence labeled to the third target substance TS3. In this case, the detecting of the fourth target substance TS4 may be performed by comparing fluorescence detected from the tissue sample SA after the second fluorescence labeling substance FL2 is provided to the tissue sample SA and fluorescence detected from the tissue sample SA before the second fluorescence labeling substance FL2 is provided to the tissue sample SA. For example, when, as in FIGS. 45 and 46, the third target substance TS3 is detected together with the fourth target substance TS4 upon the detection of the fourth target substance TS4, the fourth target substance TS4 may be detected by comparing fluorescence labels detected before and ales the providing of the second fluorescence labeling substance FL2 to the plate PL (see FIG. 47). By detecting each of the third target substance TS3 and the second target substance TS4 as described above, a position at which each target substance TS is distributed in the tissue sample SA and the amount of each target substance TS included in the tissue sample SA may be obtained.

The tissue diagnosis method in which the plurality of target substances TS are detected is not applicable only to the case in which fluorescence labels are used as in the above-described embodiments. The tissue diagnosis method in which the plurality of target substances TS are detected may be widely applied to cases in which identification labels for specifically identifying different target substances TS are the same type of labels. In other word, the method of detecting the plurality of target substances TS of the present application may be applied to various cases in which a first label which reacts specifically with a first target substance TS and a second label which reacts specifically with a second target substance TS generate similar signals.

4.3 Patches Used in Tissue Diagnosis

Embodiments of a patch PA that may be used in immunoassay according to the present embodiment will be described below. Each patch PA will be described as containing a few components, and each component may be understood as the above-describe base substance or additive substance. However, the components described below as being able to be contained in each patch PA may not be all components contained in each patch PA, and each patch PA may also contain other unspecified components.

According to an embodiment of present application, a patch PA may include a labeling substance for binding to a target substance TS included in a tissue sample SA and a mesh structural body which has a mesh structure forming micro-cavities in which the labeling substance is contained that is configured to come into contact with the tissue sample SA and provide the labeling substance to a reaction region in which the target substance TS is located. The labeling substance may be a fluorescence substance or color labeling substance (for example, staining substance).

When tissue diagnosis is performed using the patch, applying a large amount of reagent on a tissue sample to stain a tissue or label some substances of the tissue in conventional biopsy methods may be performed just by contacting a patch that contains a reagent with a tissue and separating the patch therefrom, and in this way, an amount of reagent being used may be saved.

When a reagent is provided using the patch, since, as described above, a reagent that has not bound to a target substance may easily be removed from a tissue in addition to being able to perform diagnosis economically, accuracy of diagnosis may be significantly improved. Also, by a method of applying a different patch for each diagnosis, an effect of preventing cross-contamination is also expected. Since the patch is easy to keep in comparison to a liquid specimen, it may be easier to prevent a specimen from being exposed to harmful substances.

4.3.1 Staining Patch (Hematoxylin&Eosin (H&E) Patch)

A staining patch PA which stains parts of a tissue sample SA in various colors and intensities to facilitate observation of the parts will be described below. The patch may contain a staining substance and provide the staining substance to the tissue sample. The staining substance may be a color labeling substance.

The staining substance contained in the staining patch PA may be an additive substance contained in the patch PA. The patch PA may contain a solution including the staining substance. Also, in addition to the staining substance, the patch PA may contain a separate base substance or additive substance that allows the staining substance to easily bind to an object to be stained.

The patch PA according to the present application may contain a staining substance that exhibits acidity or basicity. The staining substance which exhibits acidity or basicity may selectively bind to ionized parts present in the tissue sample SA so that the parts exhibit color.

For example, for the patch PA according to the present application, a method of staining the tissue sample SA by using hematoxylin and eosin may be used. Tissue staining using hematoxylin and eosin is one staining method that is widely used to observe a tissue. For example, to diagnose cancer, a section of tissue provided through pre-processing may be stained using hematoxylin and eosin, and the morphology of the section of tissue may be observed to determine whether cancer has developed.

The patch PA according to an embodiment of the present application may contain a staining substance for staining a nucleus included in the tissue sample SA. The patch PA may contain hematoxylin and provide hematoxylin to the tissue sample SA. Hematoxylin is a basic substance that binds to a basophilic (that is, acidic or anionic) substance to stain the basophilic substance blue, and may stain a basophilic DNA (or a nucleus including the same) dark blue or violet. However, embodiments are not limited thereto, and the patch PA for staining the nucleus according to the present embodiment may also contain methylene blue, toluidine blue, or the like and provide the same to the sample SA.

The patch PA according to another embodiment may contain a staining substance for staining a cytoplasm included in the tissue sample SA. The patch PA may contain eosin and provide eosin to the tissue sample SA. Eosin may bind to an acidophilic (that is, basic or cationic) substance to stain the acidophilic substance reddish. Therefore, eosin may stain proteins, muscle cells, and the like which exhibit basicity red or pink. Particularly, most cytoplasms are basic, i.e., eosinophilic. However, the patch PA for staining the cytoplasms may contain acid fuchsin, orange G, and the like instead of eosin.

The patch PA according to yet another embodiment may also contain a staining substance that exhibits neutrality. For example, the patch PA may contain a staining substance that simultaneously has a part exhibiting positivity and a peat exhibiting negativity. In this case, the past exhibiting positivity and the part exhibiting negativity of the tissue sample SA may be stained to exhibit different colors.

4.3.2 Antibody Patch

An antibody patch PA used in immunological tissue diagnosis will be described below.

The antibody may be an additive substance contained in the patch PA. The patch PA may contain a solution including the antibody. Also, in addition to the antibody, the patch PA may contain a separate base substance or additive substance that allows the antibody to easily bind specifically.

The antibody used in the immunological tissue diagnosis of the present application may be: 1) an antibody that has a property of binding specifically to a target protein and has an identification label attached thereto; or 2) a primary antibody having a property of binding specifically to a target protein and a secondary antibody having a property of binding specifically to the primary antibody and having an identification label attached thereto.

4.3.2.1 Immunostaining Patch

The patch PA according to the present application may contain an immunostaining substance that facilitates observation of parts of the tissue sample SA through an antigen-antibody reaction. The patch PA may contain the immunostaining substance and provide the immunostaining substance to the reaction region or the tissue sample SA. The tissue diagnosis according to the present application may include acquiring an image in which the target protein is labeled from the tissue sample SA by using the immunostaining patch PA.

The immunostaining substance may include an antibody that binds specifically to a target protein by an antigen-antibody reaction. The antibody that binds specifically to the target protein may indicate a region in which the target protein is distributed. The antibody may be a color labeling substance. The antibody may have an enzyme attached thereto. The antibody having the enzyme attached thereto may catalyze a chemical reaction of a substrate SU. A product PD generated due to the chemical reaction may color-label the target protein.

The target protein may be an antigen related to a specific disease, and the providing of the staining substance may include providing an antibody, which binds specifically to the antigen and has an enzyme attached thereto, and a substrate SU, which is catalyzed by the enzyme and generates a precipitation which exhibits color. The immunostaining substance may induct a color reaction in a region in which the target protein is located. In other words, the patch PA which contains the immunostaining substance may generate a precipitation which exhibits color in the region in which the target protein is located or induce a color reaction in the region to stain the region.

4.3.2.2 Immunofluorescence Patch/Immunochemical Fluorescence Patch

The patch PA according to the present application may contain a fluorescence labeling substance did allows fluorescence to be detected from a target protein through an antigen-antibody reaction, and provide the fluorescence labeling substance to the tissue sample SA. The tissue diagnosis according to the present application may include acquiring an image in which the target protein is fluorescence-labeled from the tissue sample SA by using the patch PA that contains the fluorescence labeling substance. Alternatively, the tissue diagnosis may include measuring an amount of fluorescence with which the target protein is labeled from the tissue sample SA.

The fluorescence labeling substance may include, as the antibody which binds specifically to the target protein, an antibody to which a fluorescence label is attached. The antibody to which the fluorescence label is attached may bind specifically to a target protein to be detected. The fluorescence labeling substance may include, as the antibody which binds specifically to the target protein, an antibody to which an enzyme for emitting fluorescence through a reaction of a substrate SU is attached.

In this case, in the present embodiment, for the fluorescence emission, a substrate patch that contains a substrate SU for forming fluorescence by a chemical reaction catalyzed by the enzyme attached to the antibody may be provided.

4.3.3 ISH Patch

An ISH patch PA that includes a probe which binds specifically to a target base sequence and is used in detecting the target base sequence will be described below. The tissue diagnosis according to the present application may include acquiring an image in which a distribution of the target base sequence is labeled from the tissue sample SA by using the ISH patch PA.

The probe may be an additive substance contained in the patch PA. The patch PA may contain a solution including the probe. Also, in addition to the probe, the patch PA may contain a separate base substance or additive substance that allows the probe to easily bind specifically.

4.3.3.1 FISH Patch

The patch PA according to the present application may contain a fluorescence labeling substance for labeling a target base sequence and provide the fluorescence labeling substance to the tissue sample SA. The tissue diagnosis according to the present application may include acquiring an image in which the target base sequence is fluorescence-labeled from the tissue sample SA by using the patch PA that contains the fluoresces-labeling substance for labeling the target base sequence. Alternatively, the tissue diagnosis may include measuring an amount of fluorescence labeled to the target base sequence from the tissue sample SA.

The fluorescence labeling substance according to the present embodiment may be a probe that binds specifically to the target base sequence. The fluorescence labeling substance may include, as the probe that binds specifically to the target base sequence, a probe to which a fluorescence label is attached. The fluorescence labeling substance may include, as the probe that binds specifically to the target base sequence, a probe to which an enzyme for emitting fluorescence through a reaction of a substrate SU is attached.

In this case, in the present embodiment, for the fluorescence emission, a substrate SU patch PA that contains a substrate SU far forming fluorescence by a chemical reaction catalyzed by the enzyme attached to be probe may be separately provided.

4.3.3.2 CISH Patch

The patch PA according to the present application may contain a staining substance for labeling a target base sequence and provide the staining substance to the tissue sample SA. The tissue diagnosis according to the present application may include acquiring at image in which the target base sequence is labeled first the tissue sample SA by using the patch PA that contains the staining substance for labeling the target base sequence.

The staining substance according to the present embedment may include a probe that binds specifically to the target base sequence. The staining substance may include, as the probe that binds specifically to the target base sequence, a probe to which a color substance is attached.

4.3.4 DAPI Staining Patch

The patch PA according to the present application may contain a fluorescence labeling substance for labeling a DNA and provide the fluorescence labeling substance to the tissue sample SA. The tissue diagnosis according to the present application may include obtaining the morphology and distribution of DNA included in the tissue sample SA by using the patch PA that contains the fluorescence labeling substance for labeling the DNA.

The fluorescence labeling substance according to the present embodiment may include a DAPI reagent that infiltrates into the DNA. The patch PA may provide the fluorescence labeling substance including the DAPI to the tissue sample SA, and the distribution of DNA included in the sample sample SA to which the DAPI is provided may be obtained by detecting blue fluorescence. Therefore, the distribution or morphology of a nucleus included in the tissue sample SA may be obtained by detecting blue fluorescence.

The identification of nucleus by DAPI may be solely used or used together with other techniques in observing the tissue sample SA. For example, when it is desired to observe an endothelial tissue, in addition to the patch PA that contains DAPI, a separate patch PA that contains an isothiocyanate derivative (TRITC) that labels a microfiber with red fluorescence, a fluorescein isothiocyanate (FITC) that labels a microtubule with green fluorescence, or the like may be used to label multiple parts included in the tissue sample SA and observe the parts.

The DAPI may be an additive substance contained in the patch PA, in addition to the DAPI, the patch PA may contain a separate base substance or additive substance that allows the DAPI to easily infiltrate into the DNA.

As the DAPI reagent is contained in the patch according to the present application and provided to a tissue, only an optimal animus of reagent required for staining a nucleus may be provided to a reaction region, and residual DAPI that has not bound to a nucleus may be re-absorbed into the patch just by separating the patch from the tissue. This may allow a fluorescence process to be more conveniently and promptly performed.

4.3.5 Buffer Patch

The patch PA of the present application may contain a substance that facilitates performance of the tissue diagnosis, come into contact with a reaction space, and provide a predetermined environment to the reaction space or the tissue sample SA.

The patch PA according to an embodiment of the present application may contain a buffer solution that allows a staining substance to easily bind to a staining target substance TS and provide an environment that facilitates the binding to the reaction region.

For example, according to an embodiment of the present application, the patch PA may contain a buffer solution at a pH of 7.4 and provide an environment suitable for binding between a DAPI stain and a DNA included in the sample SA. The providing of the environment to the reaction region may be performed by contacting the patch PA with the reaction region. Since the DAPI stain is sensitive to light. The patch PA may have a light shielding function.

4.3.6 Washing Patch

The tissue diagnosis according to the preset application may be performed using a washing patch PA that absorbs a residue. In other words, the tissue diagnosis method according to the present embodiment may include absorbing a residue by contacting the washing patch with the plate PL and separating the washing patch from the plate PL. The residue may include a fluorescence labeling substance (e.g., an antibody) that has not bound to a target protein.

The washing patch may contain a wasting solution. The washing solution may include a tris buffered saline (TBS) or phosphate buffered saline (PBS) with Tween 20. In accordance with a residue to be absorbed, the washing solution may be provided as a solution in which the residue may be dissolved.

According to the present embodiment, a washing patch may allow residual substance that is nonspecifically placed on the plate PL to be easily reproved. Accordingly, in comparison to a conventional method which essentially requires, before and after applying each reagent used in detecting a specific reaction, a process in which a large amount of washing solution is spayed onto the plate PL to wash off residual substance, a more precise detection result may be derived.

In addition to the washing solution, the washing patch may contain a separate base substance or additive substance that improves the washing efficiency.

Figure 59:
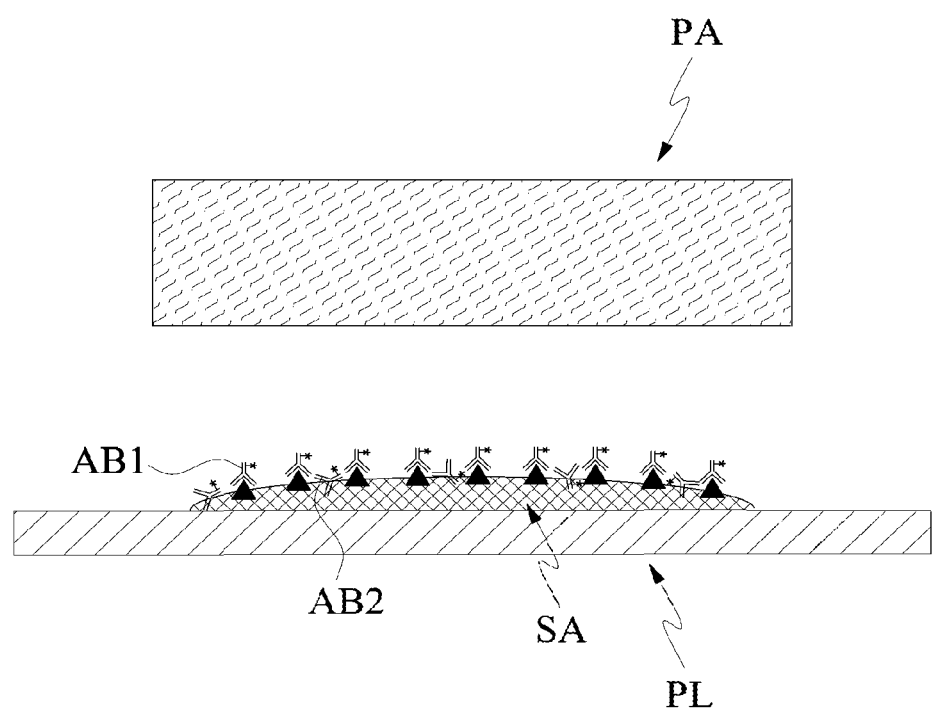
FIG. 59 illustrates a case in which a wasting patch is used, as an embodiment of tissue diagnosis method according to the present application.
Figure 60:
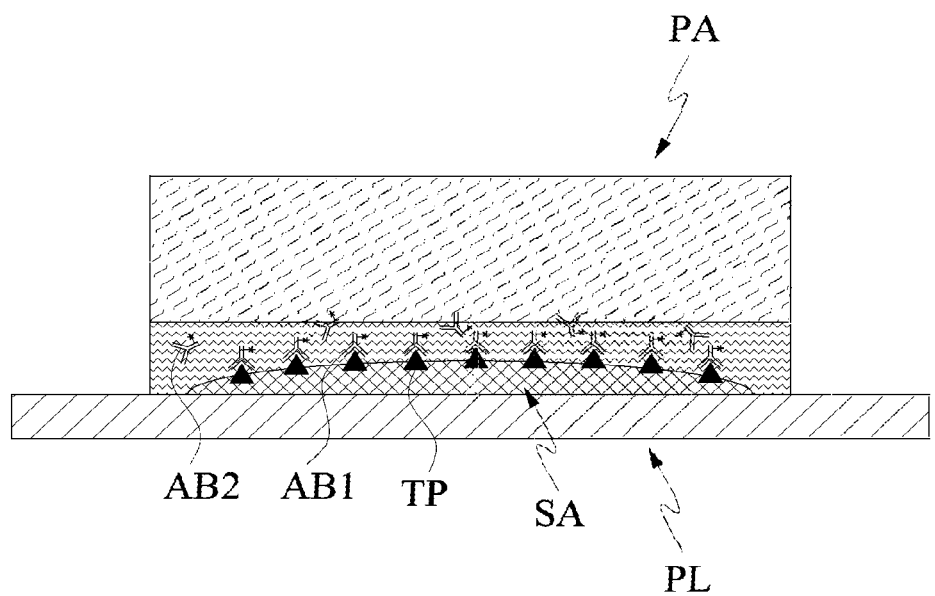
FIG. 60 illustrates a case in which a washing patch is used, as an embodiment of a tissue diagnosis method according to the present application.
Figure 61:
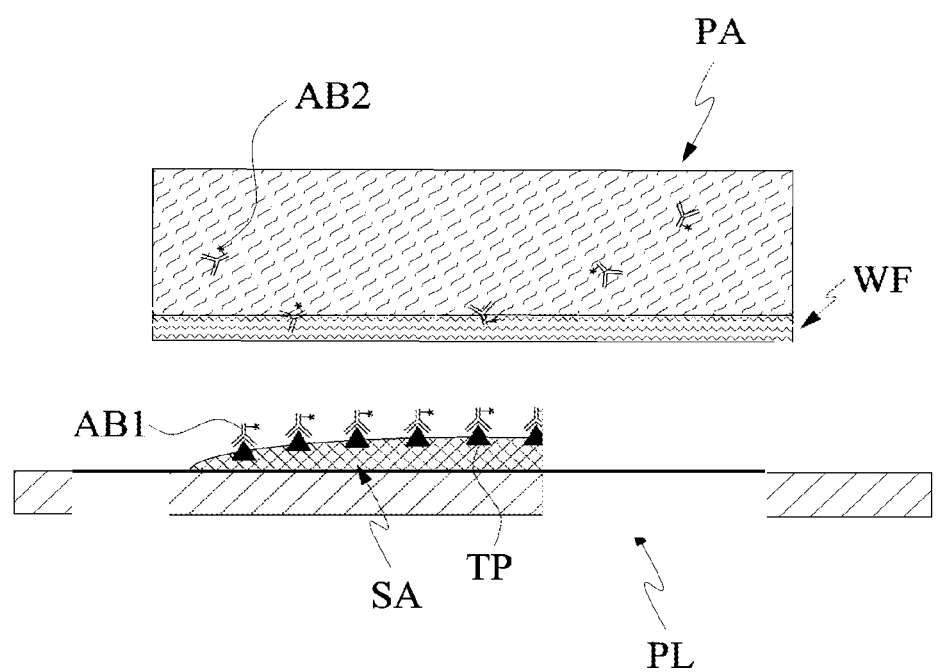
FIG. 61 illustrates a case in which a washing patch is used, as an embodiment of a tissue diagnosis method according to the present application.

FIGS. 59 to 61 briefly illustrate removing a residue from a reaction region using the washing patch PA, as an embodiment of a tissue diagnosis method according to the present application. Here, the residue may refer to a substance that has not participated in a reaction for detecting a target substance TS. The residue may be residual substance (e.g., residual labeling substance) the has not participated in a specific reaction for detecting the target substance TS.

Referring to FIGS. 59 to 61, the washing patch PA may absorb a residue from the plate PL. According to the present embodiment, by contacting the washing patch PA with the tissue sample SA and separating the washing patch PA from the tissue sample SA, the residue may be removed from the reaction region. When de washing patch PA is in contact with the tissue sample SA, a water film WF may be formed in the vicinity of a contact region, and the residue may be dissolved in the water film WF. When the wasting patch PA is separated from the tissue sample SA, the water film WF may move along with the patch PA, and an antibody AB2, with is the residue, may be captured in the water film WF and absorbed into the patch PA. In this case, an antibody AB1, which has bound to a target protein TP, may not be absorbed into the patch.

Although an antibody that has not bound to a target protein has been given as an example of a residue in the present embodiment, the residue is not limited thereto. The residue may include a probe that has not bound to a target base sequence, a staining substance that has not bound to a target substance TS, and the like.

By performing washing of a reaction region using the wanting patch as described above, a washing process used in conventional tissue diagnosis may be replaced. Conventionally, applying a large amount of washing solution on a sample to wash off a residue is essentially required to perform washing, and the large amount of washing solution is consumed in this process. When washing of a tissue is performed using the washing patch according to the present application instead of the above-described conventional method, an amount of washing solution being used may be significantly saved.

4.3.7 Plurality of Patches

The tissue diagnosis according to the present application may be performed using a plurality of patches PA.

The tissue diagnosis using the plurality of patches may be used to detect a plurality of target substances. For example, when detecting a plurality of target proteins, a plurality of patches PA may be used.

The plurality of target proteins may include a first target substance TS and a second target substance TS, and the plurality of patches PA may include a first patch PA that contains a first labeling substance and a second patch PA that contains a second labeling substance. In this case, the first labeling substance may bind specifically to the first target substance TS and provide an identification label thereto. The second labeling substance may bind specifically to the second target substance TS and provide an identification label thereto. In this case, the identification label provided from the first labeling substance and the identification label provided from the second substance may be different from each other.

For example, the plurality of target proteins may include a first target protein and a second target protein, and the plurality of patches PA may include a first patch PA that contains a first fluorescence labeling substance and a second patch PA that contains a second fluorescence labeling substance. In this case, the first fluorescence labeling substance may bind specifically to the first protein and emit fluorescence. The second fluorescence labeling substance may bind specifically to the second target protein and emit fluorescence. A wavelength band from which the fluorescence emitted from the first fluorescence labeling substance is detected and a wavelength band from which the fluorescence emitted from the second fluorescence labeling substance is detected may be different front each other. The wavelength band from which the fluorescence emitted from the first fluorescence labeling substance is detected and the wavelength band from which the fluorescence emitted from the second fluorescence labeling substance is detected may be similar to each other.

By using the plurality of patches as described above, a plurality of target substances may be simultaneously detected. Here, the simultaneous detection includes detection of a plurality of target substances in a single diagnostic process as well as detection of a plurality of target substances at the same point in time. In this case, the plurality of target substances which are simultaneously detected using the plurality of patches may include a mixture of proteins, base sequences, cellular components, and the like. Fluorescence detection, colorimetric detection, radiation detection, and the like may be used in combination as a method of detecting a plurality of target substances.

4.4 Tissue Culture

A tissue sample SA may be cultural using a patch PA according to the present application. Particularly, by culturing the tissue sample SA, whether the tissue sample SA is a malignant tumor may be determined. Specifically, properties of a tumor may be determine by observing the growth of cells.

Culturing a tissue sample SA by using the patch PA according to the present application may include placing a sample SA on a plate PL, contacting a culture patch which includes a nutrient substance for culturing the tissue sample SA, with the sample SA, and acquiring an image of the tissue sample SA. In this case, a living body may be used at the sample SA placed at the plate PL.

The culture patch for culturing the tissue sample SA may include a substance required for the growth of tissue. For example, the culture patch may include some of a caution source, an energy source, a nitrogen source, mineral salts, vitamins, microelements, growth factors, buffers, and serums.

The acquiring of the image of the tissue sample SA may be similar to the acquiring of the image of the reaction region, the plate PL, or the tissue sample SA in the above-described embodiments.

The acquired image. i.e., an image of the cultured tissue sample SA, may be used in morphological diagnosis. For example, morphological characteristics of tumor cells may be detected, and whether tumor cells are included in the tissue sample SA may be determined. In this case, the cultured tissue sample SA may be stained to facilitate identification of parts constituting the tissue sample SA.

4.5 Tissue Diagnosis Device

Figure 62:
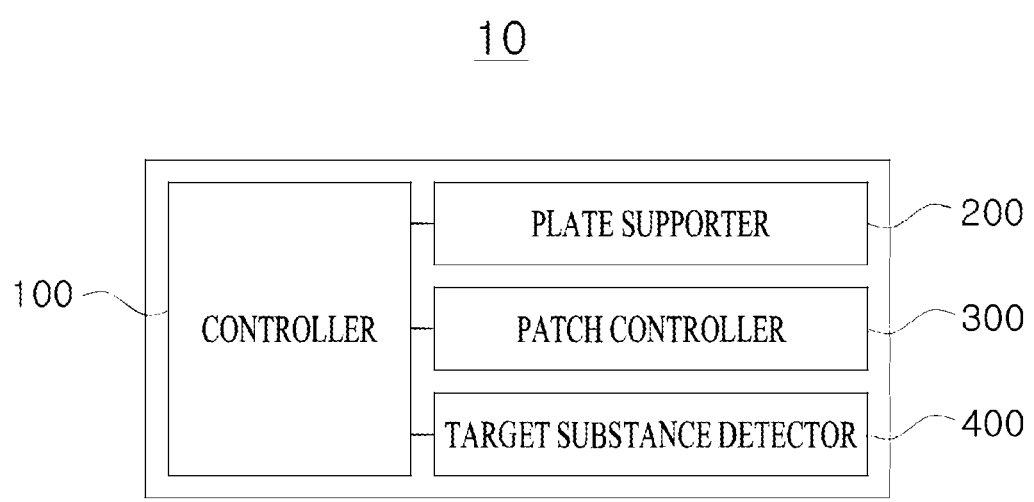
FIG. 62 illustrates an embodiment of a tissue diagnosis device according to the present application.

Refining to FIG. 62, a tissue diagnosis device 10 according to the present application may include a controller 100, a plate supporter 200, a patch controller 300, and a target substance detector 400. The tissue diagnosis device 10 may detect a target substance TS from a tissue sample SA by using a patch PA which includes a mesh structural body forming micro-cavities and is configured to contain a substance in the micro-cavities.

The controller 100 may performs tissue diagnosis in which a target substance is detected from a tissue sample by using the patch which includes the mesh structural body forming micro-cavities and is configured to contain a substance in the micro-cavities.

The controller 100 may place a tissue sample in a reaction region. The controller may provide a fluorescence labeling substance for specifically labeling a target substance to the tissue sample by using a patch that contains the fluorescence labeling substance. The controller 100 may detect a fluorescence-labeled target substance boss the tissue sample. The controller 100 may provide a staining substance to the tissue sample by using a patch that contains a color labeling substance for assigning color to the target substance. The controller 100 may detect a color-assigned target substance.

The plate supporter 200 may support a plate on which a reaction region is placed and the tissue sample SA is placed in the reaction region.

The patch controller 300 may support a patch PA that contains a labeling substance for specifically labeling the target substance TS, and control a position of the patch PA relative to the reaction region so that the patch PA is in contact with the reaction region and provides the labeling substance to the reaction region.

The target substance detector 400 may detect the labeling substance and detect the target substance TS included in the tissue sample SA.

Figure 63:
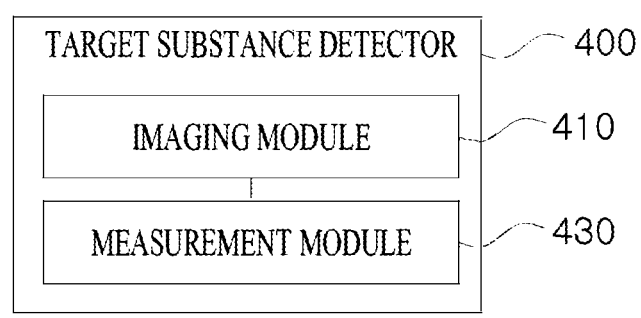
FIG. 63 illustrates a target substance detector in an embodiment of a tissue diagnosis device according to the present application in detail.

Referring to FIG. 63, in the tissue diagnosis device 10 according to the present application, the target substance TS detector 400 may include an imaging module 410 and a measurement module 430.

The imaging module 410 may acquire an image of the reaction region in which the tissue sample SA is located. The measurement module 430 may measure the amount of target substance TS included in the tissue SAMPLE SA.

The above description is merely illustrative of the technical spirit of the present disclosure, and those of ordinary skill in the art to which first present disclosure pertains should be able to make various modifications and changes within a scope not departing from essential characteristics of the present disclosure. Therefore, the above-described embodiment of the present disclosure may also be implemented separately or in combination.

The embodiments disclosed herein are for describing the technical spirit of the parent disclosure instead of limiting the same, and the scope of the technical spirit of the present disclosure is not limited by such embodiment. The scope of de present disclosure should be interpreted on the basis of the claims below, and all technical spirits within the equivalent scope should be interpreted as belonging to the scope of the present disclosure.

The invention claimed is:

1. A tissue diagnosis method for detecting a target substance from a tissue sample by using a patch which includes a mesh structural body forming micro-cavities and is configured to contain a substance in the micro-cavities, the tissue diagnosis method comprising:
    placing the tissue sample in a reaction region;
    providing a fluorescence labeling substance for specifically labeling the target substance to the tissue sample by using the patch which contains the fluorescence labeling substance; and
    detecting the fluorescence-labeled target substance from the tissue sample.

2. The tissue diagnosis method of claim 1, wherein the fluorescence labeling substance is a fluorescence labeling complex that includes a reaction derivative that reacts specifically with the target substance and a fluorescence marker for detecting the target substance.

3. The tissue diagnosis method of claim 1, wherein the detecting of the fluorescence-labeled target substance is performed by acquiring a fluorescence image of the tissue sample.

4. The tissue diagnosis method of claim 1, wherein:
    the target substance is a target base sequence included in the tissue sample; and
    the fluorescence labeling substance includes a fluorescence-labeled nucleic acid probe, the nucleic acid probe binding complementarily to the target base sequence.

5. The tissue diagnosis method of claim 1, wherein:
    the target substance is a target protein included in the tissue sample; and
    the fluorescence labeling substance include a fluorescence-labeled antibody, the antibody binds specifically to the target protein.

6. The tissue diagnosis method of claim 1, wherein the providing of the fluorescence labeling substance to the tissue sample includes:
    contacting the patch containing the fluorescence labeling substance with the tissue sample; and
    when the patch is in contact with the tissue sample, the fluorescence labeling substance is allowed to move to the reaction region.

7. The tissue diagnosis method of claim 6, wherein:
    the providing of the fluorescence labeling substances to the tissue sample further includes separating the patch containing the fluorescence labeling substances from the tissue sample; and when the patch is separated from the tissue sample, a residual fluorescence labeling substance that has not bound to the target substance of the fluorescence labeling substance is removed from the reaction region.

8. The tissue diagnosis method of claim 1, wherein the detecting of the fluorescence-labeled target substance is performed by measuring an amount of fluorescence emitted from the target substance included in the tissue sample.

9. The tissue diagnosis method of claim 1, wherein the detecting of the fluorescence-labeled target substance includes obtaining information on distribution of the target substance in the tissue sample.

10. A tissue diagnosis method for detecting a target substance from a tissue sample by using a patch which includes a mesh structural body forming micro-cavities and is configured to contain a substance in the micro-cavities, the tissue diagnosis method comprising:
 placing the tissue sample in a reaction region;
 providing a first fluorescence labeling substance for specifically labeling a first target substance to the tissue sample by using the patch which contains the first fluorescence labeling substance; and
 providing a second fluorescence labeling substance for specifically labeling a second target substance to the tissue sample by using a patch that contains the second fluorescence labeling substance.

11. The tissue diagnosis method of claim 10, wherein:
 a wavelength band from which fluorescence emitted from the first
 fluorescence labeling substance is detected and a wavelength band from which
 fluorescence emitted from the second fluorescence labeling substance is detected are different from each other; and
 the tissue diagnosis method further includes, after the providing of the second florescence labeling substance to the tissue sample, detecting the first target substance and the second target substance included in the tissue sample.

12. The tissue diagnosis method of claim 10, further comprising:
 after the providing of the first fluorescence labeling substance to the tissue sample, detecting the first target substance included in the tissue sample by detecting fluorescence emitted from the first fluorescence labeling substance; and
 after the providing of the second fluorescence labeling substance to the tissue sample, detecting the second target substance included in the tissue sample by detecting fluorescence emitted from the second fluorescence labeling substance.

13. The tissue diagnosis method of claim 12, wherein:
 a wavelength band from which the fluorescence emitted from the first fluorescence labeling substance is detected and a wavelength band from which the fluorescence is emitted from the second fluorescence labeling substance is detected at least partially overlap each other; and
 the detecting of the fluorescence emitted from the second fluorescence labeling substance is performed by comparing fluorescence detected from the tissue sample after the second fluorescence labeling substance is provided to the tissue sample and fluorescence detected from the tissue sample before the second fluorescence labeling substance is provided to the tissue sample.

\* \* \* \* \*